United States Patent [19]
Valenzuela et al.

[11] Patent Number: 5,814,478
[45] Date of Patent: Sep. 29, 1998

[54] TYROSINE KINASE RECEPTORS AND LIGANDS

[75] Inventors: David M. Valenzuela, Franklin Square; David J. Glass, White Plains; David C. Bowen, Yonkers; George D. Yancopoulos, Yorktown Heights, all of N.Y.

[73] Assignee: Regeneron Pharmaceuticals, Inc., Tarrytown, N.Y.

[21] Appl. No.: 644,271

[22] Filed: May 10, 1996

Related U.S. Application Data

[60] Provisional application No. 60/008,657, Dec. 15, 1995.
[51] Int. Cl.$^6$ ..................................................... C12P 21/06
[52] U.S. Cl. .................... 435/65.1; 435/69.7; 435/252.3; 435/320.1; 435/325; 530/300; 530/350; 536/23.1; 536/23.5
[58] Field of Search ..................................... 530/350, 300; 536/23.1, 23.5; 435/69.1, 69.7, 252.3, 320.1, 325

[56] References Cited

PUBLICATIONS

The Journal of Neuroscience, vol. 12, No. 9, Sep. 1992, pp. 3535–3544, Rupp, F., et al.: "Structure and Chromosomal Localization of the Mammalian Agrin Gene".
EMBL Database, Apr. 22, 1995, Heidelberg, Hillier, L., et al.: "The WashU–Merck EST project, AC R12830".
EMBL Database, Oct. 7, 1995, Heidelberg, Jay, P.: "Human cDNAs from HE6W library, AC H58758".
Neuron, vol. 8, No. 6, Jun. 1992, pp. 1079–1086, Ferns, M., et al.: "RNA Splicing Regulates Agrin–Mediated Acetylcholine Receptor Clustering Activity on Cultured Myotubes".
Neuron, vol. 15, No. 3, Sep. 1995, pp. 573–584, Valenzuela, D., et al., "Receptor Tyrosine Kinase Specific for the Skeletal Muscle Lineage: Expression in Embryonic Muscle, at the Neuromuscular Junction, and after Injury".
Neuron, vol. 16, Apr. 1996, pp. 755–767, Gesemann, et al.: "Alternative Splicing of Agrin Alters Its Binding to Heparin, Dystroglycan, and the Putative Agrin Receptor".

The EMBO Journal, vol. 13, No. 12, 1994, pp. 2814–2821, Hoch, W., et al.: "Structural domains of agrin required for clustering of nicotinic acetylcholine receptors".
The EMBO Journal, vol.15., No. 11, pp. 2625–2631, Meier, T., et al.: "AChR phosphorylation and aggregation induced by an agrin fragment that lacks the binding domain for α–dystroglycan".
The Journal of Cell Biology, vol. 128, No. 4, Feb. 1995, pp. 625–636, Gesemann, M., "Acetylcholine Receptor–aggregating Activity Of Agrin Isoforms and Mapping of the Active Site".
The Journal of Cell Biology, vol. 128, No. 6, Mar. 1995, pp. 1121–1129, Wallace B.: "Regulation of the interaction of nicotinic acetylcholine receptors with the cytoskeleton by agrin–activated protein tyrosine kinase".
Annual Reviews in Neuroscience, vol. 18, 1995, pp. 443–462, Bo3we, M. and Fallon, J.: "The Role Of Agrin In Synapse Formation".
Cell, vol. 80, No. 5, Mar. 10, 1995, pp. 675–679, Campbell, K.: "Three Muscular Dystroiphies: Loss of Cytoskeleton–Extracellular Matrix Linkage".
Cell, vol. 85, No. 4, May 17, 1996, pp. 513–523, Glass, D., et al.: "Agrin Acts via a MuSK Receptor Complex".
Ngo et al. The Protein Folding Problem and Tertiary Structure Prediction. Merz et al (Eds) Brikhause, Boston, 1994 pp. 491–495.

*Primary Examiner*—Stephen Walsh
*Assistant Examiner*—Kenneth A. Sorensen
*Attorney, Agent, or Firm*—Robert J. Cobert

[57] ABSTRACT

The present invention provides for a gene, designated as musk, that encodes a novel tyrosine kinase receptor expressed in high levels in denervated muscle. The invention also provides for an isolated and purified polypeptide which activates MuSK receptor. The invention further provides for a polypeptide which is functionally equivalent to the MuSK activating polypeptide. The invention also provides assay systems that may be used to detect and/or measure ligands that bind the musk gene product. The present invention also provides for diagnostic and therapeutic methods based on molecules that activate MuSK.

21 Claims, 23 Drawing Sheets

Fig. 1A

```
       *5        10        15        20        25        30        35        40        45        50        55        60        65        70
        *         *         *         *         *         *         *         *         *         *         *         *         *         *
       GAATTCGGCA CGAGCAAACA GTCATTAGTG GACGACTCTA TTGTAATAAA CTGTGCTTTA AAATGTAAAC 75        80        85        90        95       100       105       110       115       120       125       130       135
        *         *         *         *         *         *         *         *         *         *         *         *         *
       CAGGGAGCGT TTTTTTTCCT CACATTGTCC AGAAGCAACC TTTCTTCCTG AGCCTGGATT AATC ATG
                                                                              M>

140       145       150       155       160       165       170       175       180       185       190
          *         *         *         *         *         *         *         *         *         *         *
         AGA GAG CTC GTC AAC ATT CCA CTG TTA CAG ATG CTC ACC CTG GTT GCC TTC AGC GGG
          R   E   L   V   N   I   P   L   L   Q   M   L   T   L   V   A   F   S   G>

195       200       205       210       215       220       225       230       235       240       245       250
        *         *         *         *         *         *         *         *         *         *         *         *
       ACC GAG AAA CTT CCA AAA GCC CCT GTC ATC ACC ACG CCT CTT GAA ACT GTA GAT GCC
        T   E   K   L   P   K   A   P   V   I   T   T   P   L   E   T   V   D   A>

255       260       265       270       275       280       285       290       295       300       305
          *         *         *         *         *         *         *         *         *         *         *
         TTA GTT GAA GAA GTG GCG ACT TTC ATG TGC GCC GTG GAA TCC TAC CCT CAG CCT GAA
          L   V   E   E   V   A   T   F   M   C   A   V   E   S   Y   P   Q   P   E>

310       315       320       325       330       335       340       345       350       355       360       365
        *         *         *         *         *         *         *         *         *         *         *         *
       ATT TCT TGG ACC AGA AAT AAA ATT CTC ATC AAG CTG TTT GAC ACC CGC TAC AGC ATC
        I   S   W   T   R   N   K   I   L   I   K   L   F   D   T   R   Y   S   I>

370       375       380       385       390       395       400       405       410       415       420
          *         *         *         *         *         *         *         *         *         *         *
         CGA GAG AAC GGT CAG CTC CTC ACC ATC CTG AGT GTG GAG GAC AGT GAT GAT GGC ATC
          R   E   N   G   Q   L   L   T   I   L   S   V   E   D   S   D   D   G   I>

425       430       435       440       445       450       455       460       465       470       475
        *         *         *         *         *         *         *         *         *         *         *
       TAC TGC TGC ACA GCC AAC AAT GGA GTG GGA GGA GCG GTG GAA AGT TGT GGC GCC CTG
        Y   C   C   T   A   N   N   G   V   G   G   A   V   E   S   C   G   A   L>

480       485       490       495       500       505       510       515       520       525       530       535
        *         *         *         *         *         *         *         *         *         *         *         *
       CAA GTG AAG ATG AAG CCT AAA ATA ACT CGT CCT CCC ATC AAT GTA AAA ATA ATT GAG
        Q   V   K   M   K   P   K   I   T   R   P   P   I   N   V   K   I   I   E>

540       545       550       555       560       565       570       575       580       585       590
          *         *         *         *         *         *         *         *         *         *         *
         GGA TTG AAA GCA GTC CTA CCG TGC ACT ACG ATG GGT AAC CCC AAG CCA TCC GTG TCC
          G   L   K   A   V   L   P   C   T   T   M   G   N   P   K   P   S   V   S>

595       600       605       610       615       620       625       630       635       640       645       650
        *         *         *         *         *         *         *         *         *         *         *         *
       TGG ATT AAG GGG GAC AGT GCT CTC AGG GAA AAT TCC AGG ATT GCA GTT CTT GAA TCT
        W   I   K   G   D   S   A   L   R   E   N   S   R   I   A   V   L   E   S>

655       660       665       670       675       680       685       690       695       700       705
          *         *         *         *         *         *         *         *         *         *         *
         GGG AGT TTA AGG ATC CAT AAT GTG CAA AAG GAA GAC GCA GGA CAG TAC CGA TGT GTG
          G   S   L   R   I   H   N   V   Q   K   E   D   A   G   Q   Y   R   C   V>

710       715       720       725       730       735       740       745       750       755       760
        *         *         *         *         *         *         *         *         *         *         *
       GCA AAA AAC AGC CTG GGC ACA GCT TAC TCC AAA CTG GTG AAG CTG GAA GTG GAG GTT
        A   K   N   S   L   G   T   A   Y   S   K   L   V   K   L   E   V   E   V>

765       770       775       780       785       790       795       800       805       810       815       820
        *         *         *         *         *         *         *         *         *         *         *         *
       TTT GCA AGA ATC CTG CGT GCT CCT GAA TCC CAC AAT GTC ACC TTT GGT TCC TTT GTA
        F   A   R   I   L   R   A   P   E   S   H   N   V   T   F   G   S   F   V>
```

Fig. 1B

```
        825       830       835       840       845       850       855       860       865       870       875
         *                   *                   *                   *                   *
       ACC CTA CGC TGC ACA GCA ATA GGC ATG CCT GTC CCC ACC ATC AGC TGG ATT GAA AAC
        T   L   R   C   T   A   I   G   M   P   V   P   T   I   S   W   I   E   N>

880       885       890       895       900       905       910       915       920       925       930       935
         *                   *                   *                   *                   *                   *
       GGA AAT GCT GTT TCT TCA GGT TCC ATT CAA GAG AAT GTG AAA GAC CGA GTG ATT GAC
        G   N   A   V   S   S   G   S   I   Q   E   N   V   K   D   R   V   I   D>

940       945       950       955       960       965       970       975       980       985       990
                 *                   *                   *                   *                   *
               TCA AGA CTC CAG CTC TTT ATC ACA AAG CCA GGA CTC TAC ACA TGC ATA GCT ACC AAT
                S   R   L   Q   L   F   I   T   K   P   G   L   Y   T   C   I   A   T   N>

995      1000      1005      1010      1015      1020      1025      1030      1035      1040      1045
         *                   *                   *                   *                   *
       AAG CAT GGA GAG AAA TTC AGT ACC GCA AAG GCT GCA GCC ACT GTC AGT ATA GCA GAA
        K   H   G   E   K   F   S   T   A   K   A   A   A   T   V   S   I   A   E>

1050      1055      1060      1065      1070      1075      1080      1085      1090      1095      1100      1105
         *                   *                   *                   *                   *                   *
       TGG AGC AAA TCA CAG AAA GAA AGC AAA GGC TAC TGT GCC CAG TAC AGA GGG GAG GTG
        W   S   K   S   Q   K   E   S   K   G   Y   C   A   Q   Y   R   G   E   V>

1110      1115      1120      1125      1130      1135      1140      1145      1150      1155      1160
         *                   *                   *                   *                   *
       TGT GAT GCC GTC CTG GTG AAA GAC TCT CTT GTC TTC TTC AAC ACC TCC TAT CCC GAC
        C   D   A   V   L   V   K   D   S   L   V   F   F   N   T   S   Y   P   D>

1165      1170      1175      1180      1185      1190      1195      1200      1205      1210      1215      1220
         *                   *                   *                   *                   *                   *
       CCT GAG GAG GCC CAA GAG CTG CTG ATC CAC ACT GCG TGG AAT GAA CTC AAG GCT GTG
        P   E   E   A   Q   E   L   L   I   H   T   A   W   N   E   L   K   A   V>

1225      1230      1235      1240      1245      1250      1255      1260      1265      1270      1275
         *                   *                   *                   *                   *
       AGC CCA CTC TGC CGA CCA GCT GCC GAG GCT CTG CTG TGT AAT CAC CTC TTC CAG GAG
        S   P   L   C   R   P   A   A   E   A   L   L   C   N   H   L   F   Q   E>

1280      1285      1290      1295      1300      1305      1310      1315      1320      1325      1330
         *                   *                   *                   *                   *
       TGC AGC CCT GGA GTG CTA CCT ACT CCT ATG CCC ATT TGC AGA GAG TAC TGC TTG GCA
        C   S   P   G   V   L   P   T   P   M   P   I   C   R   E   Y   C   L   A>

1335      1340      1345      1350      1355      1360      1365      1370      1375      1380      1385      1390
         *                   *                   *                   *                   *                   *
       GTA AAG GAG CTC TTC TGT GCA AAG GAA TGG CTG GCA ATG GAA GGG AAG ACC CAC CGC
        V   K   E   L   F   C   A   K   E   W   L   A   M   E   G   K   T   H   R>

1395      1400      1405      1410      1415      1420      1425      1430      1435      1440      1445
                 *                   *                   *                   *                   *
               GGA CTC TAC AGA TCC GGG ATG CAT TTC CTC CCG GTC CCG GAG TGC AGC AAG CTT CCC
                G   L   Y   R   S   G   M   H   F   L   P   V   P   E   C   S   K   L   P>

1450      1455      1460      1465      1470      1475      1480      1485      1490      1495      1500      1505
         *                   *                   *                   *                   *                   *
       AGC ATG CAC CAG GAC CCC ACA GCC TGC ACA AGA CTG CCG TAT TTA GAT TAT AAA AAA
        S   M   H   Q   D   P   T   A   C   T   R   L   P   Y   L   D   Y   K   K>

1510      1515      1520      1525      1530      1535      1540      1545      1550      1555      1560
                 *                   *                   *                   *                   *
               GAA AAC ATA ACA ACA TTC CCG TCC ATA ACG TCC TCC AAG CCG AGC GTG GAC ATT CCA
                E   N   I   T   T   F   P   S   I   T   S   S   K   P   S   V   D   I   P>

1565      1570      1575      1580      1585      1590      1595      1600      1605      1610      1615
         *                   *                   *                   *                   *
       AAC CTG CCT GCC TCC ACG TCT TCC TTC GCC GTC TGG CCT GCG TAC TCC ATG ACT GTC
        N   L   P   A   S   T   S   S   F   A   V   S   P   A   Y   S   M   T   V>
```

Fig. 1C

```
1620  1625  1630  1635  1640  1645  1650  1655  1660  1665  1670  1675
 *           *           *           *           *           *
ATC ATC TCC ATC ATG TCC TGC TTT GCG GTG TTT GCT CTC CTC ACC ATC ACT ACT CTC
 I   I   S   I   M   S   C   F   A   V   F   A   L   L   T   I   T   T   L>

1680  1685  1690  1695  1700  1705  1710  1715  1720  1725  1730
 *           *           *           *           *           *
TAT TGC TGC CGA AGG AGG AGA GAG TGG AAA AAT AAG AAA AGA GAG TCG GCA GCG GTG
 Y   C   C   R   R   R   R   E   W   K   N   K   K   R   E   S   A   A   V>

1735  1740  1745  1750  1755  1760  1765  1770  1775  1780  1785  1790
 *           *           *           *           *           *
ACC CTC ACC ACA TTG CCT TCC GAG CTC CTG CTG GAC AGG CTG CAT CCC AAC CCC ATG
 T   L   T   T   L   P   S   E   L   L   L   D   R   L   H   P   N   P   M>

1795  1800  1805  1810  1815  1820  1825  1830  1835  1840  1845
 *           *           *           *           *
TAC CAG AGG ATG CCA CTC CTT CTG AAT CCC AAG TTG CTC AGC CTG GAG TAT CCG AGG
 Y   Q   R   M   P   L   L   L   N   P   K   L   L   S   L   E   Y   P   R>

1850  1855  1860  1865  1870  1875  1880  1885  1890  1895  1900
 *           *           *           *           *           *
AAT AAC ATC GAG TAT GTC AGA GAC ATC GGA GAG GGA GCG TTT GGA AGG GTC TTT CAA
 N   N   I   E   Y   V   R   D   I   G   E   G   A   F   G   R   V   F   Q>

1905  1910  1915  1920  1925  1930  1935  1940  1945  1950  1955  1960
 *           *           *           *           *           *
GCG AGG GCC CCA GGC TTG CTT CCT TAT GAA CCC TTC ACT ATG GTG GCT GTG AAG ATG
 A   R   A   P   G   L   L   P   Y   E   P   F   T   M   V   A   V   K   M>

1965  1970  1975  1980  1985  1990  1995  2000  2005  2010  2015
 *           *           *           *           *
CTG AAG GAG GAG GCC TCC GCA GAT ATG CAG GCA GAC TTT CAG AGG GAG GCA GCC CTC
 L   K   E   E   A   S   A   D   M   Q   A   D   F   Q   R   E   A   A   L>

2020  2025  2030  2035  2040  2045  2050  2055  2060  2065  2070  2075
 *           *           *           *           *           *
ATG GCG GAG TTT GAC AAC CCC AAC ATT GTG AAG CTC TTA GGT GTG TGT GCT GTT GGG
 M   A   E   F   D   N   P   N   I   V   K   L   L   G   V   C   A   V   G>

2080  2085  2090  2095  2100  2105  2110  2115  2120  2125  2130
 *           *           *           *           *
AAG CCA ATG TGC CTG CTC TTT GAA TAT ATG GCC TAT GGT GAC CTC AAT GAG TTC CTC
 K   P   M   C   L   L   F   E   Y   M   A   Y   G   D   L   N   E   F   L>

2135  2140  2145  2150  2155  2160  2165  2170  2175  2180  2185
 *           *           *           *           *
CGA AGC ATG TCC CCT CAC ACT GTG TGC AGC CTC AGC CAC AGT GAC CTG TCC ACG AGG
 R   S   M   S   P   H   T   V   C   S   L   S   H   S   D   L   S   T   R>

2190  2195  2200  2205  2210  2215  2220  2225  2230  2235  2240  2245
 *           *           *           *           *           *
GCT CGG GTG TCC AGC CCT GGT CCT CCA CCC CTG TCT TGT GCG GAA CAG CTC TGT ATT
 A   R   V   S   S   P   G   P   P   P   L   S   C   A   E   Q   L   C   I>

2250  2255  2260  2265  2270  2275  2280  2285  2290  2295  2300
 *           *           *           *           *
GCC AGG CAA GTG GCA GCT GGC ATG GCC TAC CTG TCG GAG CGC AAG TTT GTC CAT CGG
 A   R   Q   V   A   A   G   M   A   Y   L   S   E   R   K   F   V   H   R>

2305  2310  2315  2320  2325  2330  2335  2340  2345  2350  2355  2360
 *           *           *           *           *           *
GAC TTA GCT ACC AGG AAC TGC CTG GTT GGA GAG AAC ATG GTG GTG AAA ATT GCA GAC
 D   L   A   T   R   N   C   L   V   G   E   N   M   V   V   K   I   A   D>

2365  2370  2375  2380  2385  2390  2395  2400  2405  2410  2415
 *           *           *           *           *
TTT GGC CTC TCT AGG AAC ATC TAC TCC GCA GAC TAC TAC AAA GCT GAT GGA AAC GAT
 F   G   L   S   R   N   I   Y   S   A   D   Y   Y   K   A   D   G   N   D>
```

Fig. 1D

```
    2420  2425  2430  2435  2440  2445 2450  2455   2460 2465  2470
     *           *           *          *             *         *
    GCT ATA CCT ATC CGC TGG ATG CCA CCC GAG TCT ATC TTC TAC AAC CGC TAC ACC ACG
     A   I   P   I   R   W   M   P   P   E   S   I   F   Y   N   R   Y   T   T>

2475 2480  2485  2490 2495  2500  2505 2510   2515  2520 2525  2530
     *           *          *           *             *         *
    GAG TCA GAT GTG TGG GCT TAT GGC GTG GTC CTC TGG GAG ATC TTC TCC TAT GGA CTG
     E   S   D   V   W   A   Y   G   V   V   L   W   E   I   F   S   Y   G   L>

2535 2540  2545   2550 2555  2560  2565 2570   2575  2580 2585
       *           *          *           *             *
    CAG CCC TAC TAT GGA ATG GCC CAT GAG GAG GTC ATT TAC TAT GTG AGA GAT GGT AAC
     Q   P   Y   Y   G   M   A   H   E   E   V   I   Y   Y   V   R   D   G   N>

2590  2595 2600  2605  2610 2615  2620   2625 2630  2635   2640 2645
     *           *          *           *             *         *
    ATC CTT GCC TGC CCT GAG AAC TGT CCC TTG GAA CTG TAC AAC CTT ATG CGC CTA TGT
     I   L   A   C   P   E   N   C   P   L   E   L   Y   N   L   M   R   L   C>

2650  2655 2660  2665  2670 2675  2680   2685 2690  2695  2700
       *           *          *           *             *         *
    TGG AGC AAG CTG CCT GCA GAC AGA CCC AGC TTC TGC AGT ATC CAC CGG ATC CTG CAG
     W   S   K   L   P   A   D   R   P   S   F   C   S   I   H   R   I   L   Q>

2705  2710  2715 2720   2725  2730 2735   2740  2745 2750  2755 2760
            *           *            *            *           *         *
    CGC ATG TGC GAG AGA GCA GAG GGA ACG GTA GGC GTC TAA GGTTGACCA TGCTCAAACA
     R   M   C   E   R   A   E   G   T   V   G   V   *>

2765 2770  2775 2780   2785 2790   2795 2800   2805 2810   2815 2820  2825 2830
            *           *            *            *           *         *         *
    ACACCCAGGA GGATCTTTTC AGACTGCGAG CTGGAGGGAT CCTAAAGCAG AGGGCGNATA AGNNCAGATA 2835 2840  2845 2850   2855 2860  2865
            *           *          *
    GGAAGAGTTT ATCTCAGGCA GCACGTNCAG TTGGTTGTT
```

Fig. 4A

```
              10          20          30          40          50          60
              •           •           •           •           •           •
ATG AGA GAG CTC GTC AAC ATT CCA CTG GTA CAT ATT CTT ACT CTG GTT GCC TTC AGC GGA
 M   R   E   L   V   N   I   P   L   V   H   I   L   T   L   V   A   F   S   G 70          80          90         100         110         120
              •           •           •           •           •           •
ACT GAG AAA CTT CCA AAA GCT CCT GTC ATC ACC ACT CCT CTT GAA ACA GTG GAT GCC TTA
 T   E   K   L   P   K   A   P   V   I   T   T   P   L   E   T   V   D   A   L 130         140         150         160         170         180
              •           •           •           •           •           •
GTT GAA GAA GTG GCT ACT TTC ATG TGT GCA GTG GAA TCC TAC CCC CAG CCT GAG ATT TCC
 V   E   E   V   A   T   F   M   C   A   V   E   S   Y   P   Q   P   E   I   S 190         200         210         220         230         240
              •           •           •           •           •           •
TGG ACT AGA AAT AAA ATT CTC ATT AAA CTC TTT GAC ACC CGC TAC AGC ATC CGG GAG AAT
 W   T   R   N   K   I   L   I   K   L   F   D   T   R   Y   S   I   R   E   N 250         260         270         280         290         300
              •           •           •           •           •           •
GGG CAG CTC CTC ACC ATC CTG AGT GTG GAA GAC AGT GAT GAT GGC ATT TAC TGC TGC ACG
 G   Q   L   L   T   I   L   S   V   E   D   S   D   D   G   I   Y   C   C   T 310         320         330         340         350         360
              •           •           •           •           •           •
GCC AAC AAT GGT GTG GGA GGA GCT GTG GAG AGT TGT GGA GCC CTG CAA GTG AAG ATG AAA
 A   N   N   G   V   G   G   A   V   E   S   C   G   A   L   Q   V   K   M   K 370         380         390         400         410         420
              •           •           •           •           •           •
CCT AAA ATA ACT CGC CCT CCC ATA AAT GTG AAA ATA ATA GAG GGA TTA AAA GCA GTC CTA
 P   K   I   T   R   P   P   I   N   V   K   I   I   E   G   L   K   A   V   L 430         440         450         460         470         480
              •           •           •           •           •           •
CCA TGT ACT ACA ATG GGT AAT CCC AAA CCA TCA GTG TCT TGG ATA AAG GGA GAC AGC CCT
 P   C   T   T   M   G   N   P   K   P   S   V   S   W   I   K   G   D   S   P 490         500         510         520         530         540
              •           •           •           •           •           •
CTC AGG GAA AAT TCC CGA ATT GCA GTT CTT GAA TCT GGG AGC TTG AGG ATT CAT AAC GTA
 L   R   E   N   S   R   I   A   V   L   E   S   G   S   L   R   I   H   N   V 550         560         570         580         590         600
              •           •           •           •           •           •
CAA AAG GAA GAT GCA GGA CAG TAT CGA TGT GTG GCA AAA AAC AGC CTC GGG ACA GCA TAT
 Q   K   E   D   A   G   Q   Y   R   C   V   A   K   N   S   L   G   T   A   Y 610         620         630         640         650         660
              •           •           •           •           •           •
TCC AAA GTG GTG AAG CTG GAA GTT GAG GTT TTT GCC AGG ATC CTG CGG GCT CCT GAA TCC
 S   K   V   V   K   L   E   V   E   V   F   A   R   I   L   R   A   P   E   S 670         680         690         700         710         720
              •           •           •           •           •           •
CAC AAT GTC ACC TTT GGC TCC TTT GTG ACC CTG CAC TGT ACA GCA ACA GGC ATT CCT GTC
 H   N   V   T   F   G   S   F   V   T   L   H   C   T   A   T   G   I   P   V
```

Fig. 4B

```
         730           740           750           760           770           780
          •             •             •             •             •             •
CCC ACC ATC ACC TGG ATT GAA AAC GGA AAT GCT GTT TCT TCT GGG TCC ATT CAA GAG AGT
 P   T   I   T   W   I   E   N   G   N   A   V   S   S   G   S   I   Q   E   S 790           800           810           820           830           840
          •             •             •             •             •             •
GTG AAA GAC CGA GTG ATT GAC TCA AGA CTG CAG CTG TTT ATC ACC AAG CCA GGA CTC TAC
 V   K   D   R   V   I   D   S   R   L   Q   L   F   I   T   K   P   G   L   Y 850           860           870           880           890           900
          •             •             •             •             •             •
ACA TGC ATA GCT ACC AAT AAG CAT GGG GAG AAG TTC AGT ACT GCC AAG GCT GCA GCC ACC
 T   C   I   A   T   N   K   H   G   E   K   F   S   T   A   K   A   A   A   T 910           920           930           940           950           960
          •             •             •             •             •             •
ATC AGC ATA GCA GAA TGG AGT AAA CCA CAG AAA GAT AAC AAA GGC TAC TGC GCC CAG TAC
 I   S   I   A   E   W   S   K   P   Q   K   D   N   K   G   Y   C   A   Q   Y 970           980           990          1000          1010          1020
          •             •             •             •             •             •
AGA GGG GAG GTG TGT AAT GCA GTC CTG GCA AAA GAT GCT CTT GTT TTT CTC AAC ACC TCC
 R   G   E   V   C   N   A   V   L   A   K   D   A   L   V   F   L   N   T   S 1030          1040          1050          1060          1070          1080
          •             •             •             •             •             •
TAT GCG GAC CCT GAG GAG GCC CAA GAG CTA CTG GTC CAC ACG GCC TGG AAT GAA CTG AAA
 Y   A   D   P   E   E   A   Q   E   L   L   V   H   T   A   W   N   E   L   K 1090          1100          1110          1120          1130          1140
          •             •             •             •             •             •
GTA GTG AGC CCA GTC TGC CGG CCA GCT GCT GAG GCT TTG TTG TGT AAC CAC ATC TTC CAG
 V   V   S   P   V   C   R   P   A   A   E   A   L   L   C   N   H   I   F   Q 1150          1160          1170          1180          1190          1200
          •             •             •             •             •             •
GAG TGC AGT CCT GGA GTA GTG CCT ACT CCT ATT CCC ATT TGC AGA GAG TAC TGC TTG GCA
 E   C   S   P   G   V   V   P   T   P   I   P   I   C   R   E   Y   C   L   A 1210          1220          1230          1240          1250          1260
          •             •             •             •             •             •
GTA AAG GAG CTC TTC TGC GCA AAA GAA TGG CTG GTA ATG GAA GAG AAG ACC CAC AGA GGA
 V   K   E   L   F   C   A   K   E   W   L   V   M   E   E   K   T   H   R   G 1270          1280          1290          1300          1310          1320
          •             •             •             •             •             •
CTC TAC AGA TCC GAG ATG CAT TTG CTG TCC GTG CCA GAA TGC AGC AAG CTT CCC AGC ATG
 L   Y   R   S   E   M   H   L   L   S   V   P   E   C   S   K   L   P   S   M 1330          1340          1350          1360          1370          1380
          •             •             •             •             •             •
CAT TGG GAC CCC ACG GCC TGT GCC AGA CTG CCA CAT CTA GAT TAT AAC AAA GAA AAC CTA
 H   W   D   P   T   A   C   A   R   L   P   H   L   D   Y   N   K   E   N   L 1390          1400          1410          1420          1430          1440
          •             •             •             •             •             •
AAA ACA TTC CCA CCA ATG ACG TCC TCA AAG CCA AGT GTG GAC ATT CCA AAT CTG CCT TCC
 K   T   F   P   P   M   T   S   S   K   P   S   V   D   I   P   N   L   P   S
```

Fig. 4C

```
        1450         1460         1470         1480         1490         1500
         •           •           •           •           •           •
TCC TCC TCT TCT TCC TTC TCT GTC TCA CCT ACA TAC TCC ATG ACT GTA ATA ATC TCC ATC
 S   S   S   S   S   F   S   V   S   P   T   Y   S   M   T   V   I   I   S   I 1510         1520         1530         1540         1550         1560
         •           •           •           •           •           •
ATG TCC AGC TTT GCA ATA TTT GTG CTT CTT ACC ATA ACT ACT CTC TAT TGC TGC CGA AGA
 M   S   S   F   A   I   F   V   L   L   T   I   T   T   L   Y   C   C   R   R 1570         1580         1590         1600         1610         1620
         •           •           •           •           •           •
AGA AAA CAA TGG AAA AAT AAG AAA AGA GAA TCA GCA GCA GTA ACC CTC ACC ACA CTG CCT
 R   K   Q   W   K   N   K   K   R   E   S   A   A   V   T   L   T   T   L   P 1630         1640         1650         1660         1670         1680
         •           •           •           •           •           •
TCT GAG CTC TTA CTA GAT AGA CTT CAT CCC AAC CCC ATG TAC CAG AGG ATG CCG CTC CTT
 S   E   L   L   L   D   R   L   H   P   N   P   M   Y   Q   R   M   P   L   L 1690         1700         1710         1720         1730         1740
         •           •           •           •           •           •
CTG AAC CCC AAA TTG CTC AGC CTG GAG TAT CCA AGG AAT AAC ATT GAA TAT GTG AGA GAC
 L   N   P   K   L   L   S   L   E   Y   P   R   N   N   I   E   Y   V   R   D 1750         1760         1770         1780         1790         1800
         •           •           •           •           •           •
ATC GGA GAG GGA GCG TTT GGA AGG GTG TTT CAA GCA AGG GCA CCA GGC TTA CTT CCC TAT
 I   G   E   G   A   F   G   R   V   F   Q   A   R   A   P   G   L   L   P   Y 1810         1820         1830         1840         1850         1860
         •           •           •           •           •           •
GAA CCT TTC ACT ATG GTG GCA GTA AAG ATG CTC AAA GAA GAA GCC TCG GCA GAT ATG CAA
 E   P   F   T   M   V   A   V   K   M   L   K   E   E   A   S   A   D   M   Q 1870         1880         1890         1900         1910         1920
         •           •           •           •           •           •
GCG GAC TTT CAG AGG GAG GCA GCC CTC ATG GCA GAA TTT GAC AAC CCT AAC ATT GTG AAG
 A   D   F   Q   R   E   A   A   L   M   A   E   F   D   N   P   N   I   V   K 1930         1940         1950         1960         1970         1980
         •           •           •           •           •           •
CTA TTA GGA GTG TGT GCT GTC GGG AAG CCA ATG TGC CTG CTC TTT GAA TAC ATG GCC TAT
 L   L   G   V   C   A   V   G   K   P   M   C   L   L   F   E   Y   M   A   Y 1990         2000         2010         2020         2030         2040
         •           •           •           •           •           •
GGT GAC CTC AAT GAG TTC CTC CGC AGC ATG TCC CCT CAC ACC GTG TGC AGC CTC AGT CAC
 G   D   L   N   E   F   L   R   S   M   S   P   H   T   V   C   S   L   S   H 2050         2060         2070         2080         2090         2100
         •           •           •           •           •           •
AGT GAC TTG TCT ATG AGG GCT CAG GTC TCC AGC CCT GGG CCC CCA CCC CTC TCC TGT GCT
 S   D   L   S   M   R   A   Q   V   S   S   P   G   P   P   P   L   S   C   A 2110         2120         2130         2140         2150         2160
         •           •           •           •           •           •
GAG CAG CTT TGC ATT GCC AGG CAG GTG GCA GCT GGC ATG GCT TAC CTC TCA GAA CGT AAG
 E   Q   L   C   I   A   R   Q   V   A   A   G   M   A   Y   L   S   E   R   K
```

Fig. 4D

```
        2170          2180          2190          2200          2210          2220
TTT GTT CAC CGA GAT TTA GCC ACC AGG AAC TGC CTG GTG GGC GAG AAC ATG GTG GTG AAA
 F   V   H   R   D   L   A   T   R   N   C   L   V   G   E   N   M   V   V   K 2230          2240          2250          2260          2270          2280
ATT GCC GAC TTT GGC CTC TCC AGG AAC ATC TAC TCA GCA GAC TAC TAC AAA GCT AAT GAA
 I   A   D   F   G   L   S   R   N   I   Y   S   A   D   Y   Y   K   A   N   E 2290          2300          2310          2320          2330          2340
AAC GAC GCT ATC CCT ATC CGT TGG ATG CCA CCA GAG TCC ATT TTT TAT AAC CGC TAC ACT
 N   D   A   I   P   I   R   W   M   P   P   E   S   I   F   Y   N   R   Y   T 2350          2360          2370          2380          2390          2400
ACA GAG TCT GAT GTG TGG GCC TAT GGC GTG GTC CTC TGG GAG ATC TTC TCC TAT GGC CTG
 T   E   S   D   V   W   A   Y   G   V   V   L   W   E   I   F   S   Y   G   L 2410          2420          2430          2440          2450          2460
CAG CCC TAC TAT GGG ATG GCC CAT GAG GAG GTC ATT TAC TAC GTG CGA GAT GGC AAC ATC
 Q   P   Y   Y   G   M   A   H   E   E   V   I   Y   Y   V   R   D   G   N   I 2470          2480          2490          2500          2510          2520
CTC TCC TGC CCT GAG AAC TGC CCC GTG GAG CTG TAC AAT CTC ATG CGT CTA TGT TGG AGC
 L   S   C   P   E   N   C   P   V   E   L   Y   N   L   M   R   L   C   W   S 2530          2540          2550          2560          2570          2580
AAG CTG CCT GCA GAC AGA CCC AGT TTC ACC AGT ATT CAC CGA ATT CTG GAA CGC ATG TGT
 K   L   P   A   D   R   P   S   F   T   S   I   H   R   I   L   E   R   M   C 2590          2600          2610
GAG AGG GCA GAG GGA ACT GTG AGT GTC TAA
 E   R   A   E   G   T   V   S   V   *
```

MuSK -/-

CONTROL

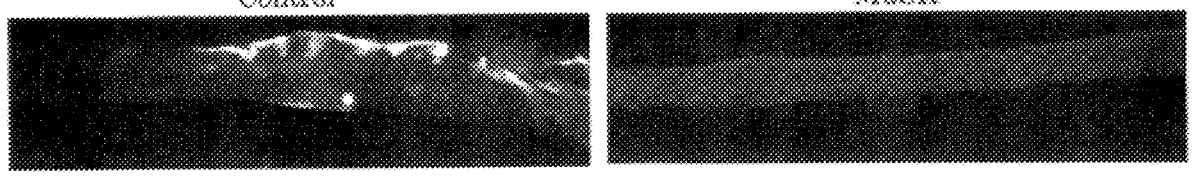
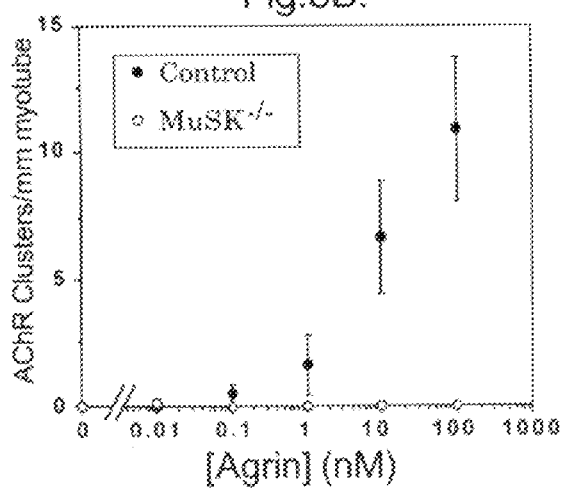
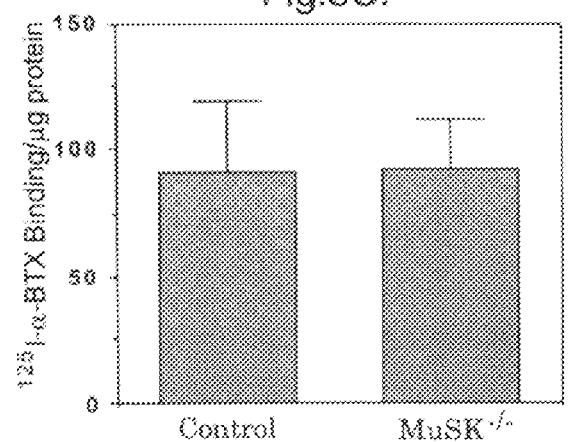

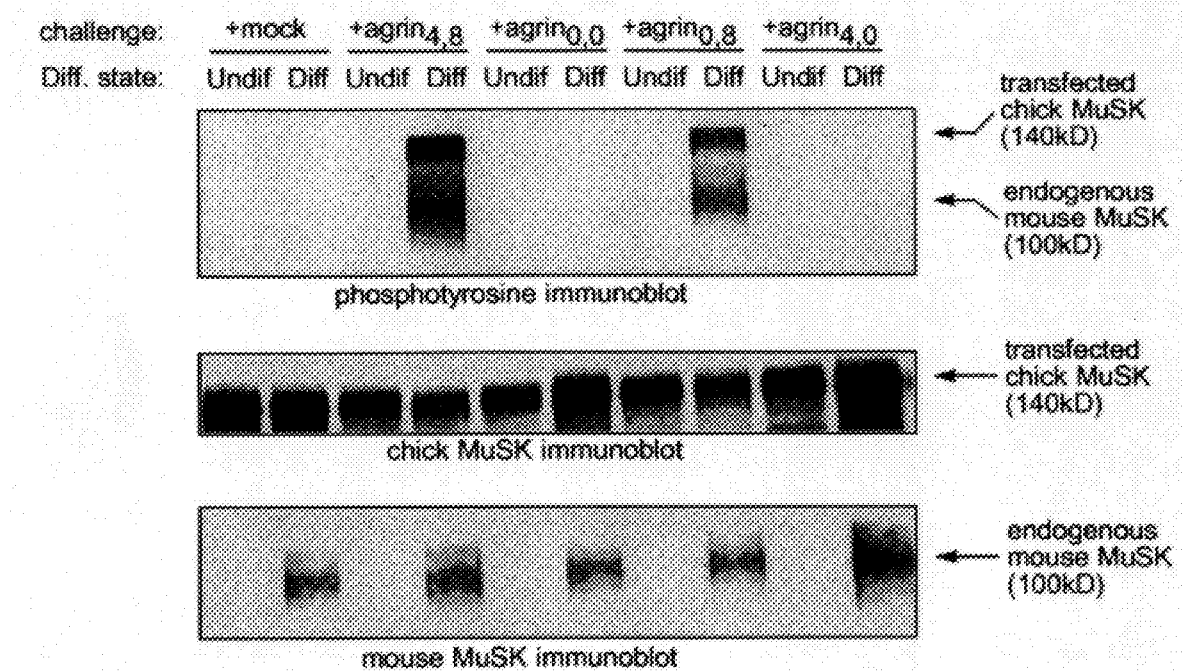

CNTF Receptor Complex
With Soluble β Components

Formation of CNTF Receptor Complex

Formation of Receptor Complex For Agrin

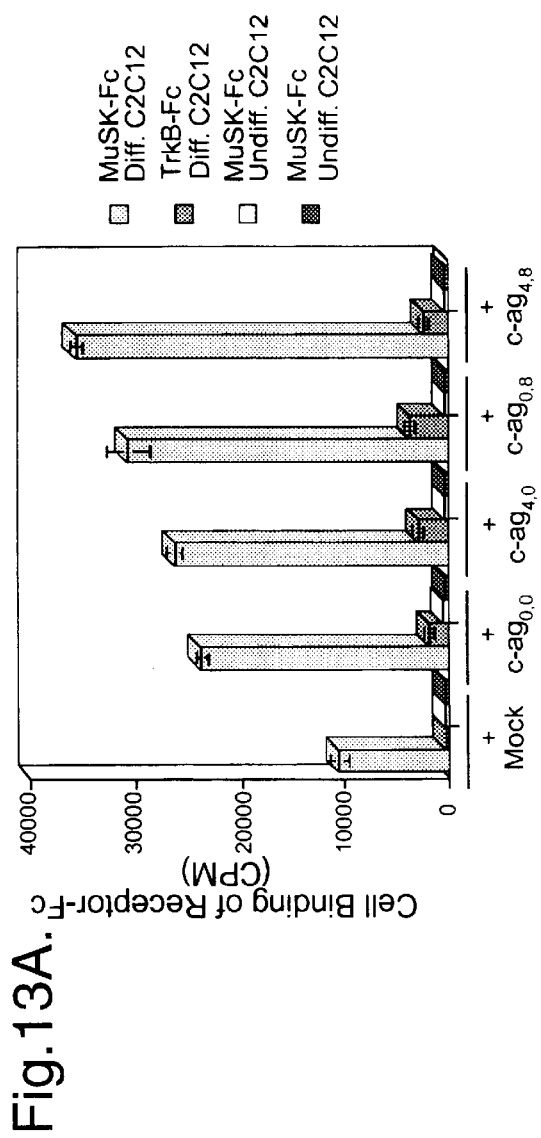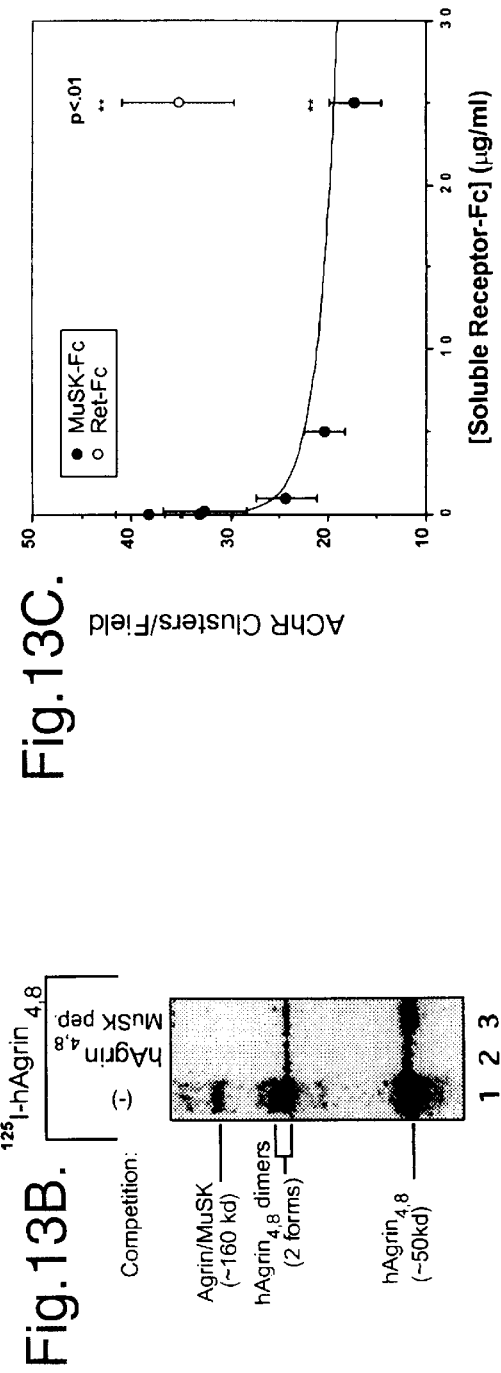

Fig. 14A

```
             10         20         30         40         50         60
              *          *          *          *          *          *
         MPPLPLEHRP RQEPGASMLV RYFMIPCNIC LILLATSTLG FAVLLFLSNY KPGIHFTPAP 70         80         90        100        110        120
              *          *          *          *          *          *
         PTPPDVCRGM LCGFGAVCEP SVEDPGRASC VCKKNACPAT VAPVCGSDAS TYSNECELQR 130        140        150        160        170        180
              *          *          *          *          *          *
         AQCNQQRRIR LLRQGPCGSR DPCANVTCSF GSTCVPSADG QTASCLCPTT CFGAPDGTVC 190        200        210        220        230        240
              *          *          *          *          *          *
         GSDGVDYPSE CQLLSHACAS QEHIFKKFNG PCDPCQGSMS DLNHICRVNP RTRHPEMLLR 250        260        270        280        290        300
              *          *          *          *          *          *
         PENCPAQHTP ICGDDGVTYE NDCVMSRIGA TRGLLLQKVR SGQCQTRDQC PETCQFNSVC 310        320        330        340        350        360
              *          *          *          *          *          *
         LSRRGRPHCS CDRVTCDGSY RPVCAQDGHT YNNDCWRQQA ECRQQRAIPP KHQGPCDQTP 370        380        390        400        410        420
              *          *          *          *          *          *
         SPCHGVQCAF GAVCTVKNGK AECECQRVCS GIYDPVCGSD GVTYGSVCEL ESMACTLGRE 430        440        450        460        470        480
              *          *          *          *          *          *
         IQVARRGPCD PCGQCRFGSL CEVETGRCVC PSECVESAQP VCGSDGHTYA SECELHVHAC 490        500        510        520        530        540
              *          *          *          *          *          *
         THQISLYVAS AGHCQTCGEK VCTFGAVCSA GQCVCPRCEH PPPGPVCGSD GVTYLSACEL 550        560        570        580        590        600
              *          *          *          *          *          *
         REAACQQQVQ IEEAHAGPCE PAECGSGGSG SGEDDECEQE LCRQRGGIWD EDSEDGPCVC 610        620        630        640        650        660
              *          *          *          *          *          *
         DFSCQSVPRS PVCGSDGVTY GTECDLKKAR CESQQELYVA AQGACRGPTL APLLPVAFPH 670        680        690        700        710        720
              *          *          *          *          *          *
         CAQTPYGCCQ DNFTAAQGVG LAGCPSTCHC NPHGSYSGTC DPATGQCSCR PGVGGLRCDR 730        740        750        760        770        780
              *          *          *          *          *          *
         CEPGFWNFRG IVTDGHSGCT PCSCDPRGAV RDDCEQMTGL CSCRPGVAGP KCGQCPDGQV 790        800        810        820        830        840
              *          *          *          *          *          *
         LGHLGCEADP MTPVTCVEIH CEFGASCVEK AGFAQCICPT LTCPEANSTK VCGSDGVTYG
```

Fig. 14B

```
              850        860        870        880        890        900
               *          *          *          *          *          *
         NECQLKAIAC RQRLDISTQS LGPCQESVTP GASPTSASMT TPRHILSKTL PFPHNSLPLS 910        920        930        940        950        960
               *          *          *          *          *          *
         PGSTTHDWPT PLPISPHTTV SIPRSTAWPV LTVPPTAAAS DVTSLATSIF SESGSANGSG 970        980        990       1000       1010       1020
               *          *          *          *          *          *
         DEELSGDEEA SGGGSGGLEP PVGSIVVTHG PPIERASCYN SPLGCCSDGK TPSLDSEGSN 1030       1040       1050       1060       1070       1080
               *          *          *          *          *          *
         CPATKAFQGV LELEGVEGQE LFYTPEMADP KSELFGETAR SIESTLDDLF RNSDVKKDFW 1090       1100       1110       1120       1130       1140
               *          *          *          *          *          *
         SVRLRELGPG KLVRAIVDVH FDPTTAFQAS DVGQALLRQI QVSRPWALAV RRPLQEHVRF 1150       1160       1170       1180       1190       1200
               *          *          *          *          *          *
         LDFDWFPTFF TGAATGTTAA MATARATTVS RLPASSVTPR VYPSHTSRPV GRTTAPPTTR 1210       1220       1230       1240       1250       1260
               *          *          *          *          *          *
         RPPTTATNMD RPRTPGHQQP SKSCDSQPCL HGGTCQDQDS GKGFTCSCTA GRGGSVCEKV 1270       1280       1290       1300       1310       1320
               *          *          *          *          *          *
         QPPSMPAFKG HSFLAFPTLR AYHTLRLALE FRALETEGLL LYNGNARGKD FLALALLDGR 1330       1340       1350       1360       1370       1380
               *          *          *          *          *          *
         VQFRFDTGSG PAVLTSLVPV EPGRWHRLEL SRHWRQGTLS VDGETPVVGE SPSGTDGLNL 1390       1400       1410       1420       1430       1440
               *          *          *          *          *          *
         DTNLYVGGIP EEQVAMVLDR TSVGVGLKGC IRMLDINNQQ LELSDWQRAA VQSSGVGECG 1450       1460       1470       1480       1490       1500
               *          *          *          *          *          *
         DHPCLPNPCH GGALCQALEA GMFLCQCPPG RFGPTCADEK SPCQPNPCHG AAPCRVLSSG 1510       1520       1530       1540       1550       1560
               *          *          *          *          *          *
         GAKCECPLGR SGTFCQTVLE TAGSRPFLAD FNGFSYLELK GLHTFERDLG EKMALEMVFL 1570       1580       1590       1600       1610       1620
               *          *          *          *          *          *
         ARGPSGLLLY NGQKTDGKGD FVSLALHNRH LEFCYDLGKG AAVIRSKEPI ALGTWVRVFL 1630       1640       1650       1660       1670       1680
               *          *          *          *          *          *
         ERNGRKGALQ VGDGPRVLGE SPKSRKVPHT MLNLKEPLYI GGAPDFSKLA RGAAVSSGFS
                              ▲
                            Y-site
```

Fig. 14C

```
          1690       1700       1710       1720       1730       1740
           *   *      *   *      *   *      *   *      *   *      *   *
      GVIQLVSLRG HQLLTQEHVL RAVDVSPFAD HPCTQALGNP CLNGGSCVPR EATYECLCPG 1750       1760       1770       1780       1790       1800
           *   *      *   *      *   *      *   *      *   *      *   *
      GFSGLHCEKG LVEKSVGDLE TLAFDGRTYI EYLNAVIESE KALQSNHFEL SLRTEATQGL
                                                 ▲Z-site
          1810       1820       1830       1840       1850       1860
           *   *      *   *      *   *      *   *      *   *      *   *
      VLWIGKAAER ADYMALAIVD GHLQLSYDLG SQPVVLRSTV KVNTNRWLRI RAHREHREGS 1870       1880       1890       1900       1910       1920
           *   *      *   *      *   *      *   *      *   *      *   *
      LQVGNEAPVT GSSPLGATQL DTDGALWLGG LQKLPVGQAL PKAYGTGFVG CLRDVVVGHR 1930       1940
           *   *      *   *
      QLHLLEDAVT KPELRPCPTP *
```

Fig. 15A

```
ATG TCT GCA CTT CTG ATC CTA GCT CTT GTT GGA GCT GCA GTT GCT GAC
 M   S   A   L   L   I   L   A   L   V   G   A   A   V   A   D

┌─start
TAC AAA GAC GAT GAC GAC AAG │AAG│ AGC CCC TGC CAG CCC AAC CCC TGC
 Y   K   D   D   D   D   K │ K │  S   P   C   Q   P   N   P   C CAT GGG GCG GCG CCC TGC CGT GTG CTG CCC GAG GGT GGT GCT CAG TGC
 H   G   A   A   P   C   R   V   L   P   E   G   G   A   Q   C GAG TGC CCC CTG GGG CGT GAG GGC ACC TTC TGC CAG ACA GCC TCG GGG
 E   C   P   L   G   R   E   G   T   F   C   Q   T   A   S   G CAG GAC GGC TCT GGG CCC TTC CTG GCT GAC TTC AAC GGC TTC TCC CAC
 Q   D   G   S   G   P   F   L   A   D   F   N   G   F   S   H CTG GAG CTG AGA GGC CTG CAC ACC TTT GCA CGG GAC CTG GGG GAG AAG
 L   E   L   R   G   L   H   T   F   A   R   D   L   G   E   K ATG GCG CTG GAG GTC GTG TTC CTG GCA CGA GGC CCC AGC GGC CTC CTG
 M   A   L   E   V   V   F   L   A   R   G   P   S   G   L   L CTC TAC AAC GGG CAG AAG ACG GAC GGC AAG GGG GAC TTC GTG TCG CTG
 L   Y   N   G   Q   K   T   D   G   K   G   D   F   V   S   L GCA CTG CGG GAC CGC CGC CTG GAG TTC CGC TAC GAC CTG GGC AAG GGG
 A   L   R   D   R   R   L   E   F   R   Y   D   L   G   K   G GCA GCG GTC ATC AGG AGC AGG GAG CCA GTC ACC CTG GGA GCC TGG ACC
 A   A   V   I   R   S   R   E   P   V   T   L   G   A   W   T AGG GTC TCA CTG GAG CGA AAC GGC CGC AAG GGT GCC CTG CGT GTG GGC
 R   V   S   L   E   R   N   G   R   K   G   A   L   R   V   G ┌────────────────Y-insert
GAC GGC CCC CGT GTG TTG GGG GAG TCC CCG │AAA TCC CGC AAG│ GTT CCG
 D   G   P   R   V   L   G   E   S   P │ K   S   R   K │ V   P CAC ACC GTC CTC AAC CTG AAG GAG CCG CTC TAC GTA GGG GGC GCT CCC
 H   T   V   L   N   L   K   E   P   L   Y   V   G   G   A   P GAC TTC AGC AAG CTG GCC CGT GCT GCT GCC GTG TCC TCT GGC TTC GAC
 D   F   S   K   L   A   R   A   A   A   V   S   S   G   F   D GGC GCC ATC CAG CTG GTC TCC CTC GGA GGC CGC CAG CTG CTG ACC CCG
 G   A   I   Q   L   V   S   L   G   G   R   Q   L   L   T   P GAG CAC GTG CTG CGG CAG GTG GAC GTC ACG TCC TTT GCA GGT CAC CCC
 E   H   V   L   R   Q   V   D   V   T   S   F   A   G   H   P TGC ACC CGG GCC TCA GGC CAC CCC TGC CTC AAT GGG GCC TCC TGC GTC
 C   T   R   A   S   G   H   P   C   L   N   G   A   S   C   V CCG AGG GAG GCT GCC TAT GTG TGC CTG TGT CCC GGG GGA TTC TCA GGA
 P   R   E   A   A   Y   V   C   L   C   P   G   G   F   S   G CCG CAC TGC GAG AAG GGG CTG GTG GAG AAG TCA GCG GGG GAC GTG GAT
 P   H   C   E   K   G   L   V   E   K   S   A   G   D   V   D
```

Fig. 15B

| | | | | | | | | | | | | | |
|---|---|---|---|---|---|---|---|---|---|---|---|---|---|
| ACC | TTG | GCC | TTT | GAC | GGG | CGG | ACC | TTT | GTC | GAG | TAC | CTC | AAC | GCT | GTG |
| T | L | A | F | D | G | R | T | F | V | E | Y | L | N | A | V |

─Z-insert

ACC GAG AGC | GAA CTG GCC AAT GAG ATC CCC GTC | GAG AAG GCA CTG CAG
 T   E   S  |  E   L   A   N   E   I   P   V  |  E   K   A   L   Q

AGC AAC CAC TTT GAA CTG AGC CTG CGC ACT GAG GCC ACG CAG GGG CTG
 S   N   H   F   E   L   S   L   R   T   E   A   T   Q   G   L

GTG CTC TGG AGT GGC AAG GCC ACG GAG CGG GCA GAC TAT GTG GCA CTG
 V   L   W   S   G   K   A   T   E   R   A   D   Y   V   A   L

GCC ATT GTG GAC GGG CAC CTG CAA CTG AGC TAC AAC CTG GGC TCC CAG
 A   I   V   D   G   H   L   Q   L   S   Y   N   L   G   S   Q

CCC GTG GTG CTG CGT TCC ACC GTG CCC GTC AAC ACC AAC CGC TGG TTG
 P   V   V   L   R   S   T   V   P   V   N   T   N   R   W   L

CGG GTC GTG GCA CAT AGG GAG CAG AGG GAA GGT TCC CTG CAG GTG GGC
 R   V   V   A   H   R   E   Q   R   E   G   S   L   Q   V   G

AAT GAG GCC CCT GTG ACC GGC TCC TCC CCG CTG GGC GCC ACG CAG CTG
 N   E   A   P   V   T   G   S   S   P   L   G   A   T   Q   L

GAC ACT GAT GGA GCC CTG TGG CTT GGG GGC CTG CCG GAG CTG CCC GTG
 D   T   D   G   A   L   W   L   G   G   L   P   E   L   P   V

GGC CCA GCA CTG CCC AAG GCC TAC GGC ACA GGC TTT GTG GGC TGC TTG
 G   P   A   L   P   K   A   Y   G   T   G   F   V   G   C   L

CGG GAC GTG GTG GTG GGC CGG CAC CCG CTG CAC CTG CTG GAG GAC GCC
 R   D   V   V   V   G   R   H   P   L   H   L   L   E   D   A

GTC ACC AAG CCA GAG CTG CGG CCC TGC CCC ACC CCA TGA
 V   T   K   P   E   L   R   P   C   P   T   P   *

5,814,478

TYROSINE KINASE RECEPTORS AND LIGANDS

This application claims priority of United States Provisional Application No. 60/008,657 filed Dec. 15, 1995 which is incorporated by reference herein.

Throughout this application various publications are referenced. The disclosures of these publications in their entireties are hereby incorporated by reference into this application.

INTRODUCTION

The present invention provides for a novel receptor molecule, a novel molecule capable of activating the receptor, and methods of making and use thereof.

BACKGROUND OF THE INVENTION

The ability of polypeptide ligands to bind cells and thereby elicit a phenotypic response such as cell growth, survival or differentiation in such cells is often mediated through receptor tyrosine kinases. The extracellular portion of each receptor tyrosine kinase (RTK) is generally the most distinctive portion of the molecule, as it provides the protein with its ligand-recognizing characteristic. Binding of a ligand to the extracellular domain results in signal transduction via an intracellular tyrosine kinase catalytic domain which transmits a biological signal to intracellular target proteins. The particular array of sequence motifs of this cytoplasmic, catalytic domain determines its access to potential kinase substrates (Mohammadi, et al., 1990, Mol. Cell. Biol., 11: 5068–5078; Fantl, et al., 1992, Cell, 69:413–413).

The tissue distribution of a particular tyrosine kinase receptor within higher organisms provides relevant data as to the biological function of the receptor.

For example, the localization of a Trk family receptor, TrkB, in tissue provided some insight into the potential biological role of this receptor, as well as the ligands that bind this receptor (referred to herein as cognates). Thus, for example, in adult mice, trkB was found to be preferentially expressed in brain tissue, although significant levels of trkB mRNAs were also observed in lung, muscle, and ovaries. Further, trkB transcripts were detected in mid and late gestation embryos. In situ hybridization analysis of 14 and 18 day old mouse embryos indicated that trkB transcripts were localized in the central and peripheral nervous systems, including brain, spinal cord, spinal and cranial ganglia, paravertebral trunk of the sympathetic nervous system and various innervation pathways, suggesting that the trkB gene product may be a receptor involved in neurogenesis and early neural development as well as play a role in the adult nervous system.

The cellular environment in which an RTK is expressed may influence the biological response exhibited upon binding of a ligand to the receptor. Thus, for example, when a neuronal cell expressing a Trk receptor is exposed to a neurotrophin which binds that receptor, neuronal survival and differentiation results. When the same receptor is expressed by a fibroblast, exposure to the neurotrophin results in proliferation of the fibroblast (Glass, et al., 1991, Cell 66:405–413). Thus, it appears that the extracellular domain provides the determining factor as to the ligand specificity, and once signal transduction is initiated the cellular environment will determine the phenotypic outcome of that signal transduction.

A number of RTK families have been identified based on sequence homologies of their intracellular domains. For example, two members of the TIE (tyrosine kinase with immunoglobulin and EGF homology domains) family, known as TIE-1 and TIE-2, have 79% sequence homology in their intracellular region (Maisonpierre, et al., 1993, Oncogene 8:1631–1637).

Although these receptors share similar motifs in their extracellular domain, only 32% of the sequences are identical.

A receptor having a kinase domain that is related to the Trk family has been identified in the electric ray *Torpedo californica* and may play a role in motor neuron induced synapses on muscle fibers. Jennings, et al. Proc. Natl. Acad. Sci. USA 90: 2895–2899 (1993). This kinase was isolated from the electric organ, a tissue which is a specialized form of skeletal muscle. The tyrosine kinase domain of this protein is related to the Trk family, while the extracellular domain is somewhat divergent from the Trks. The protein was found to be expressed at high levels in Torpedo skeletal muscle, and at much lower levels in adult Torpedo brain, spinal cord, heart, liver and testis.

Often such novel RTKs are identified and isolated by searching for additional members of known families of tyrosine kinase receptors using, for example, PCR-based screens involving known regions of homology among Trk family members. (See, for example, Maisonpierre, et al., 1993, Oncogene 8: 1631–1637). Isolation of such so called "orphan" tyrosine kinase receptors, for which no ligand is known, and subsequent determination of the tissues in which such receptors are expressed, provides insight into the regulation of the growth, proliferation and regeneration of cells in target tissues. The identification and isolation of novel RTKs may be used as a means of identifying new ligands or activating molecules that may then be used to regulate the survival, growth, differentiation and/or regeneration of cells expressing the receptors. Further, because RTKs appear to mediate a number of important functions during development, the identification and isolation of such receptors, ligands and activating molecules enhances our understanding of developmental processes and may improve our ability to diagnose or treat abnormal conditions.

For example, the above described methods may be used to study an event that occurs during development of the neuromuscular junction (NMJ)—the localization of acetylcholine receptors at the synapse. It has long been known that important signals are exchanged across the NMJ (Nitkin et al., 1987, J.Cell.Biol. 105: 2471–2478; Hall, Z. W. and Sanes, J. R., 1993, Cell/Neuron (Suppl.) 72/10: 99–121; Bowe, M. A. and Fallon, J. R., 1995, Ann. Rev. Neurosci. 18: 443–462; Sanes, J. R., 1995, Devel. Biol. 6: 163–173; Burden, S. J., et al., 1995, Devel. Biol. 6: 59–65). These signals include the chemical transmitter, acetylcholine, which is released from vesicles in the nerve terminal, recognized by acetylcholine receptors (AChRs) on the muscle, and ultimately results in electrical activation and contraction of the muscle.

Muscle also provides neurotrophic factors that support survival of motor neurons (DeChiara, T. et al., 1995, Cell 83: 313–322), and the nerve may in turn provide myotrophic factors that maintain muscle mass (Helgren, M. E., et al., 1994, Cell 76: 493–504). Reciprocal signaling interactions are also critical both for the formation and maintenance of the neuromuscular junction itself. Such signals regulate recognition of nerve-to-muscle contact, arrest the growth of the incoming nerve ending, and induce formation of a highly specialized nerve terminal marked by a polarized arrangement of synaptic vesicles and active zones. Simultaneously, precisely juxtaposed with respect to the nerve terminal, a complex molecular apparatus forms on the muscle membrane. This specialized postsynaptic structure, termed the motor endplate, comprises a tiny patch on the muscle membrane which is characterized by a dense clustering of particular proteins; some of these may receive nerve-derived signals, as AChRs are known to do, while others may be involved in creating the molecular scaffold for this postsynaptic specialization.

Signals produced by the nerve induce postsynaptic clusters by at least two mechanisms. First, these signals can induce redistribution of pre-existing molecules that are initially expressed throughout the myofiber, and second, they can induce localized transcription of specific genes only by subsynaptic nuclei underlying the NMJ. Between the nerve terminal and the motor endplate is a narrow synaptic cleft containing a complex basal lamina. This basal lamina is distinguished from the adjacent extracellular matrix by the accumulation of a number of proteins, such as acetylcholinesterase and s-laminin. The synaptic basal lamina also serves as a reservoir for signaling molecules exchanged between nerve and muscle.

While the reciprocal interactions between nerve and muscle have been intensively explored for decades, many questions still remain concerning the precise nature of the signals involved in formation of the NMJ. The realization that empty sheaths of the synaptic basal lamina could induce formation of both nerve terminal specializations and motor endplates suggested that key signaling molecules might be embedded in the extracellular matrix (Sanes, J. R. et al., 1978, J.Cell. Biol. 78: 176–198; Burden, S. J., et al., 1979, J.Cell. Biol. 82: 412–425; McMahan, U. J. and Slater, C. R., 1984, J.Cell. Biol. 98: 1453–1473; Kuffler, D. P., 1986, J.Comp. Neurol. 250: 228–235). Indeed, recent findings indicate that a protein discovered for its AChR-inducing activity and thus termed ARIA (Jessell, T. M., et al., 1979, PNAS (USA) 76: 5397–5401; Falls, D. L., et al., 1990, Cold Spring Harbor Symp. Quant. Biol. 55: 397–406; Falls, D. L., et al., 1993, Cell 72: 801–815) which can increase the expression of several of the AChR subunit genes (Harris, D. A., 1989, et al., Nature 337:173–176; Martinou, J.-C., et al., 1991, PNAS (USA) 88: 7669–7673; Jo, S. A., et al., 1995, Nature 373: 158–161; Chu, G. C., et al., 1995, Neuron 14: 329–339), is localized to the synaptic basal lamina (Jo, S. A., et al., 1995, Nature 373: 158–161; Goodearl, A. D., et al., 1995, J.Cell. Biol. 130: 1423–1434). Molecular cloning has revealed that ARIA corresponds to a factor alternatively referred to as neuregulin, NDF, heregulin or glia growth factor, and binds to the erbB family of RTKs (Carraway, K. L. and Burden, S. J., 1995, Curr. Opin. Neurobiol. 5: 606–612). Interestingly, neuregulin production has been demonstrated in motor neurons and neuregulin receptors, erbB3 and erbB4, have recently been localized to the motor endplate, supporting the idea that nerve-derived neuregulin provides an important signal to muscle that regulates transcription from subsynaptic nuclei (Altiok, N., et al., 1995, EMBO J. 14: 4258–4266; Moscoso, L. M., et al., 1995, Dev. Biol. 172: 158–169; Zhu, X., et al., 1995, EMBO J. 14: 5842–5848).

Another protein, known as agrin, was isolated from the synaptic basal lamina based on its ability to cause redistribution of pre-existing AChRs into clusters on the surface of cultured myotubes (Godfrey, E. W., et al., 1984, J.Cell. Biol. 99: 615–627; Rupp, F., et al., 1991, Neuron 6: 811–823; Tsim, K. W., et al., 1992, Neuron 8: 677–689). In contrast to neuregulin, agrin does not appear to regulate AChR expression. However, agrin causes the clustering of a number of synaptic components, along with AChRs, in cultured myotubes (Wallace, B. G., 1989, J.Neurosci. 9: 1294–1302).

A variety of data are consistent with the notion that agrin also acts in vivo to induce and maintain the postsynaptic membrane specialization. Most important among these are the findings that the most active forms of agrin are exclusively made by neurons and are deposited in the synaptic basal lamina (Ruegg, M. A., et al., 1992, Neuron 8: 691–699; Ferns, M., et al., 1993, Neuron 11: 491–502; Hoch, W., et al., 1993, Neuron 11: 479–490), and that antibodies to agrin block nerve-induced clustering of AChRs on cultured myotubes (Reist, N. E., et al., 1992, Neuron 8: 865–868).

The precise mechanism of action of agrin remains a mystery (Sealock, R. and Froehner, S. C., 1994, Cell 77: 617–619). Agrin is known to induce tyrosine phosphorylation of AChRs, and inhibitors of tyrosine phosphorylation block agrin-mediated clustering (Wallace, B. G., et al., 1991, Neuron 6: 869–878; Wallace, B. G., 1994, J.Cell. Biol. 125: 661–668; Qu, Z. and Huganir, R. L., 1994, J.Neurosci. 14: 6834–6841; Wallace, B. G., 1995, J.Cell. Biol. 128: 1121–1129).

Intriguing recent findings have revealed that agrin can directly bind to α-dystroglycan, an extrinsic peripheral membrane protein that is attached to the cell surface by covalent linkage to β-dystroglycan, which in turn couples to the intracellular cytoskeletal scaffold via an associated protein complex (Bowe, M. A., et al., 1994, Neuron 12: 1173–1180; Campanelli, J. T., et al., 1994, Cell 77: 673–674; Gee, S. H., et al., 1994, Cell 77: 675–686; Sugiyama, J., et al., 1994, Neuron 13: 103–115; Sealock, R. and Froehner, S. C., 1994, Cell 77: 617–619).

Extrasynaptically, the dystroglycan complex binds laminin on its extracellular face, and couples to the actin scaffold via a spectrin-like molecule known as dystrophin. At the synapse however, agrin (via its own laminin-like domains) may be able to substitute for laminin, whereas utrophin (a dystrophin related protein) replaces dystrophin as the link to actin (reviewed in (Bowe, M. A. and Fallon, J. R., 1995, Ann. Rev. Neurosci. 18: 443–462)). The dystroglycan complex co-clusters with AChRs in response to agrin in vitro, and components of this complex are concentrated at the endplate in vivo (reviewed in (Bowe, M. A. and Fallon, J. R., 1995, Ann. Rev. Neurosci. 18: 443–462)).

Recent evidence suggests that a 43 kD cytoplasmic protein, known as rapsyn, anchors AChRs to a sub-synaptic cytoskeleton complex, probably via interactions with the dystroglycan complex (Cartaud, J. and Changeux, J. P., 1993, Eur. J. Neurosci. 5: 191–202; Apel, E. D., et al., 1995, Neuron 15: 115–126). Gene disruption studies reveal that rapsyn is absolutely necessary for clustering of AChRs, as well as of the dystroglycan complex. However, other aspects of NMJ formation, involving presynaptic differentiation and synapsespecific transcription, are seen in mice lacking rapsyn (Gautam, M., et al., 1995, Nature 377: 232–236).

Despite the findings that agrin can bind directly to α-dystroglycan, and that AChRs and the dystroglycan complex are linked and co-cluster in response to agrin, the role of dystroglycan as an agrin receptor remains unclear (Sealock, R. and Froehner, S. C., 1994, Cell 77: 617–619; Ferns, M., et al., 1996, J. Cell Biol. 132: 937–944). It has recently been reported that a 21 kD fragment of chick agrin is sufficient to induce AChR aggregation (Gesemann, M., et al., 1995, J. Cell. Biol. 128: 625–636). Dystroglycan could be directly involved in activating signaling pathways that appear to be required for clustering, such as those involving tyrosine phosphorylation, by an unknown mechanism (for example, via association with a cytoplasmic tyrosine kinase).

Alternatively, dystroglycan could be involved in couplings of agrin not only to AChRs but to a novel signaling receptor. It also remains possible that dystroglycan does not play an active or required role in initiating clustering, and is merely among an assortment of post-synaptic molecules that undergo clustering. Recent evidence indicates that the agrin fragment that is active in inducing AChR aggregation does not bind to α-dystroglycan and a structural role in aggregation, rather than a signal transfer role, has been proposed for the binding of agrin to α-dystroglycan (Gesemann, M., et al., 1996, Neuron 16: 755–767).

SUMMARY OF THE INVENTION

The present invention provides for a novel tyrosine kinase, termed "MuSK" for "muscle specific kinase," that is expressed in normal and denervated muscle, as well as other tissues including heart, spleen, ovary or retina (See Valenzuela, D., et al., 1995, Neuron 15: 573–584). The novel tyrosine kinase has alternatively been referred to as "Dmk" for "denervated muscle kinase." Thus, the terms MuSK and Dmk may be used interchangeably. The protein appears to be related to the Trk family of tyrosine kinases.

The present invention further provides for an isolated nucleic acid molecule encoding MuSK.

The present invention also provides for a protein or peptide that comprises the extracellular domain of MuSK and the nucleic acid which encodes such extracellular domain. The invention further provides for vectors comprising an isolated nucleic acid molecule encoding MuSK or its extracellular domain, which can be used to express MuSK in bacteria, yeast and mammalian cells.

The present invention also provides for use of the MuSK receptor or its extracellular or intracellular domain to screen for drugs that interact with or activate MuSK. Novel agents that bind to and/or activate the receptor described herein may mediate survival, proliferation and differentiation in cells naturally expressing the receptor, but also may mediate survival, proliferation or differentiation when used to treat cells engineered to express the receptor.

In particular embodiments, the extracellular domain (soluble receptor) of MuSK is utilized in screens for cognate ligands and activating molecules. For example, the MuSK receptor activating molecule described herein may be used in a competition assay to identify agents capable of acting as receptor agonists or antagonists by competing the agents with MuSK activating molecule for phosphorylation of the MuSK receptor. Specifically, the active portion of human agrin described herein may be used as the MuSK activating molecule in a competition assay to screen for agents capable of acting as receptor agonists or antagonists.

The term "MuSK activating molecule" as used herein refers to a molecule which is capable of inducing phosphorylation of the MuSK receptor in the context of a differentiated muscle cell. One such activating molecule is agrin as described in the Examples set forth herein.

The present invention also provides for nucleic acid probes, capable of hybridizing with a sequence included within the nucleotide sequence encoding human MuSK or its activating molecule, useful for the detection of MuSK expressing tissue or MuSK activating molecule-expressing tissue in humans and animals. The invention further provides for antibodies capable of specifically binding MuSK or MuSK activating molecule. The antibodies may be polyclonal or monoclonal.

The present invention also has diagnostic and therapeutic utilities. In particular embodiments of the invention, methods of detecting aberrancies in the function or expression of the receptor described herein may be used in the diagnosis of muscular or other disorders. In other embodiments, manipulation of the receptor, agonists which bind this receptor, or receptor activating molecules may be used in the treatment of neurological diseases or diseases of muscle or neuromuscular unit disorders, including, but not limited to, muscular dystrophy and muscle atrophy. In further embodiments, the extracellular domain of the receptor is utilized as a blocking agent.

The present invention also provides for an isolated and purified polypeptide which activates MuSK receptor. In one embodiment, the polypeptide of the invention is encoded by a nucleotide sequence comprising the coding region of the active portion of human agrin contained in the vector designated as pBluescript human Agrin-1 (pBL-hAgrin1) that was deposited with the American Type Culture Collection on Dec. 12, 1995 under ATCC Accession No. 97378. The present invention further provides for an isolated polypeptide which is functionally equivalent to this polypeptide.

The invention further provides for an isolated and purified nucleic acid molecule comprising a nucleotide sequence encoding the active portion of human agrin, wherein the nucleotide sequence is selected from the group consisting of:

(a) the nucleotide sequence comprising the coding region of the active portion of human agrin contained in the vector designated as pBL-hAgrin 1 (ATCC Accession No. 97378);

(b) a nucleotide sequence that hybridizes under stringent conditions to the nucleotide sequence of (a) and which encodes the active portion of human agrin; and (c) a nucleotide sequence that, as a result of the degeneracy of the genetic code, differs from the nucleotide sequence of (a) or (b) and which encodes the active portion of human agrin.

The invention also provides for the above-described nucleic acid molecule which additionally contains a nucleotide sequence so that the encoded polypeptide contains the eight amino acids ELANEIPV at the position corresponding to amino acid position 1780 as shown in FIGS. 14A–14C (SEQ ID. NO. 30)

The invention also provides for a method of promoting the growth, survival or differentiation of a MuSK receptor expressing cell in culture comprising administering to the MuSK receptor expressing cell an effective amount of agrin or a derivative of agrin. In one embodiment of this method, the agrin is human agrin. In another embodiment of this method, the MuSK receptor expressing cell is a cell which is normally found in the heart, spleen, ovary, retina or skeletal muscle. In another embodiment, the MuSK receptor expressing cell is a cell which has been genetically engineered to express the MuSK receptor.

The present invention also includes a method of treating a patient suffering from a muscle disease or neuromuscular disorder comprising administering to the patient an effective amount of agrin or a derivative thereof. By way of non-limiting example, the agrin may be human agrin and the derivative may be the active portion of the human agrin molecule.

The present invention also includes an antibody capable of specifically binding human agrin. More specifically, the invention includes an antibody capable of specifically binding the active portion of human agrin. The antibody may be monoclonal or polyclonal. The invention further provides a method of detecting the presence of human agrin in a sample comprising:

a) reacting the sample with an antibody capable of specifically binding human agrin under conditions whereby the antibody binds to human agrin present in the sample; and b) detecting the bound antibody, thereby detecting the presence of human agrin in the sample.

The antibody used may be monoclonal or polyclonal. The sample may be biological tissue or body fluid. The biological tissue may be brain, muscle, or spinal cord. The body fluid may be cerebrospinal fluid, urine, saliva, blood, or a blood fraction such as serum or plasma.

The invention further provides for an isolated and purified nucleic acid molecule comprising a nucleotide sequence encoding human muscle specific kinase (MuSK) receptor, wherein the nucleotide sequence is selected from the group consisting of:

(a) the nucleotide sequence comprising the coding region of the human MuSK receptor as set forth in FIGS. 4A–4B (SEQ. ID. NOS. 28 and 29);

(b) a nucleotide sequence that hybridizes under stringent conditions to the nucleotide sequence of (a) and which encodes a human MuSK receptor; and (c) a nucleotide sequence that, as a result of the degeneracy of the genetic code, differs from the nucleotide sequence of (a) or (b) and which encodes a human MuSK receptor.

BRIEF DESCRIPTION OF THE FIGURES

FIGS. 1A–1D (SEQ. ID. NOS. 1 and 2) Nucleotide and deduced amino acid (single letter code) sequences of rat musk. The nucleotide sequence encoding mature MuSK begins around nucleotide 192.

FIGS. 4A–4D (SEQ. ID. NOS. 28 and 29) Nucleotide and deduced amino acid (single letter code) sequences of human MuSK receptor.

FIGS. 8A–8C Agrin induces AChR clustering in myotubes from control but not MuSK$^{-/-}$ mice. Myotubes derived from control and MuSK$^{-/-}$ mice were treated overnight with varying concentrations of agrin$_{4,8}$, stained with rhodamine-conjugated α-bungarotoxin (α-BGT) to label surface AChRs, and then either photographed at 64× magnification under rhodamine optics (FIG. 8A, challenge with 100 nM agrin depicted) or subjected to AChR cluster quantitation (FIG. 8B, each point represents the mean±SEM of forty myotube segments). Total AChRs on the myotubes before agrin treatment was determined by binding with $^{125}$I-α-BGT (FIG. 8C, each bar represents the mean±SEM CPM bound per μg of total cell protein (control: N=6; MuSK-/-: N=5).

FIG. 11 Agrin can only induce MuSK phosphorylation in the context of a differentiated myotube: evidence for a myotube-specific accessory component. Agrin-inducible phosphorylation of an introduced chick MuSK receptor was evaluated in a clone of C2C12 myoblasts stably transfected with a chick MuSK expression vector. The introduced chick MuSK is expressed regardless of whether this C2C12 clone is undifferentiated ("Undif") or differentiated into myotubes ("Dif") (middle panel), in contrast to the endogenous mouse MuSK, which is only expressed in differentiated cells (bottom panel). However, the chick MuSK can only be inducibly phosphorylated in response to agrin when it is assayed in differentiated myotubes (top panel). The chick MuSK displays the same specificity for activation by the various agrin isoforms (each at 10 nM for ten minutes) as does the endogenous mouse MuSK (compare transfected chick MuSK and endogenous mouse MuSK in upper panel).

FIG. 12A—Schematic representation depicting the step-wise assembly of the multi-component receptor complex for ciliary neurotrophic factor (CNTF); b1, gp130; b2, LIFRb. FIG. 12B—Schematic depiction of the use of soluble b receptor components (Fc-tagged) to build a CNTF receptor complex attached to the cell surface via only one of its components, the non-signaling a component; surface binding of the soluble b components can be detected using antibodies recognizing the Fc tag. FIG. 12C—Schematic representation of one of several possible models of the MuSK receptor complex for agrin, depicting requirement for a myotube-associated specificity component (M.A.S.C.) and possible interactions to additional components that may be required for signaling or coupling to various effectors or substrates; these couplings may be mediated extracellularly (for example via agrin binding to the dystroglycan complex) or intracellularly (for example via interactions of SH2 domain-containing proteins to phosphorylated tyrosines on MuSK).

FIGS. 13A–13C. Evidence for an agrin/MuSK receptor complex utilizing a myotube-specific accessory component. FIG. 13A—Formation of agrin/MuSK complexes on the surface of myotubes: undifferentiated (Undiff.) or myotube-differentiated (Diff) C2C12 cells were assayed for their ability to bind either MuSK-Fc or a control receptor-Fc fusion (TrkB-Fc), in the absence or presence of various agrin isoforms (provided in conditioned media from transient COS transfections); specific binding of MuSK-Fc to the myotube surface, which is enhanced by exogenously provided agrin, is suggested to involve complexes analogous to those depicted in FIG. 12B. FIG. 13B—Direct binding of agrin to MuSK is demonstrated by cross-linking analysis. Radiolabelled agrin (a recombinant c-terminal fragment of human agrin, termed hAgrin$_{4,8}$) at 1 nM was chemically cross-linked to the surface of myotubes. Following cross-linking, lysates were immunoprecipitated with a MuSK-specific antibody (lane 1). The cross-linking was also done in the presence of excess (150 nM) unlabelled agrin (lane 2), while the immunoprecipitation was also done in the presence of excess peptide (corresponding to that used to generate the antibody) to block the MuSK precipitation; positions of the agrin/MuSK complex, as well as of various forms of unbound monomeric and dimeric agrin (see text), are indicated. FIG. 13C—Inhibition of agrin-induced AChR clustering by MuSK-Fc: agrin-induced AChR-clustering (using 10 nM c-agrin$_{4,8}$) was performed on C2C12 myotube cultures in the presence of varying concentrations of soluble MuSK-Fc or a control receptor-Fc fusion (Ret-Fc); the soluble MuSK-Fc specifically inhibits, presumably by forming inactive complexes on the cell surface with agrin and the myotube-specific accessory component.

FIGS. 14A–14C (SEQ. ID. NO. 30) Amino acid (single letter code) sequence of rat agrin indicating Y and Z sites of amino acid inserts found in splice variants.

FIGS. 15A–15B (SEQ. ID. NOS. 31 and 32) Nucleotide and amino acid (single letter code) sequences of human agrin expression construct including the signal peptide and flg tag. The start of the coding region for the active C-terminal fragment of human agrin 4–8 is indicated. Also indicated are the position Y and position Z insert sites at which the 4 and 8 amino acid inserts are located.

DETAILED DESCRIPTION OF THE INVENTION

Figure 2:
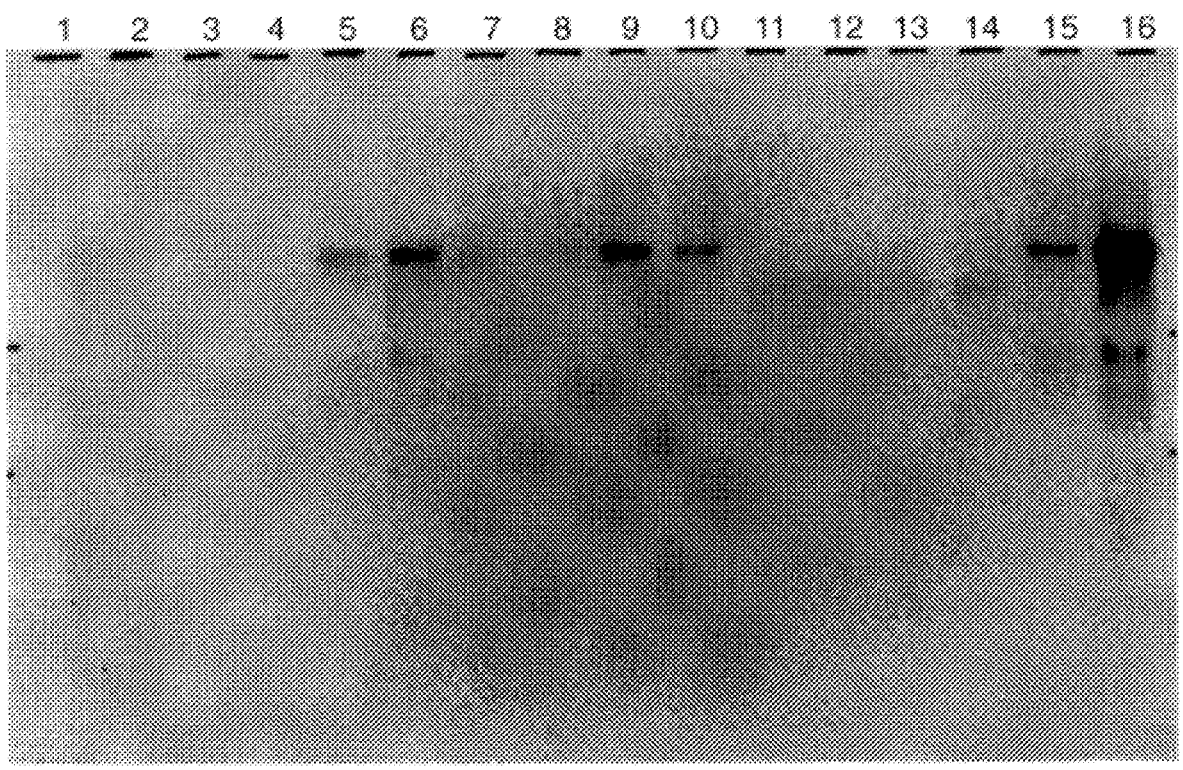
FIG. 2 Northern blot showing distribution of musk in the rat during early development. Lane 1: Total embryo E9; Lane 2: Total embryo E11; Lane 3: Placenta E11; Lane 4: Embryo head E12; Lane 5: Embryo body E12; Lane 6: Embryo spinal cord E12; Lane 7: Placenta E12; Lane 8: Embryo head E13; Lane 9: Embryo body E13; Lane 10: Embryo brain E17; Lane 11: Embryo brain P1; Lane 12: Embryo brain P10; Lane 13: Embryo brain P19; Lane 14: Adult brain; Lane 15: Adult muscle; Lane 16: Adult denervated muscle; where day of sperm positivity is designated as day E1, and day of birth is designated as day P1.

The present invention provides for a novel tyrosine kinase molecule that is related to the trk family of tyrosine kinases. The sequence of the protein is set forth in FIGS. 1A–1D as SEQ. ID NO: 1. The coding region of the mature protein is believed to begin on or around the serine-glycine-threonine on or around position 20 of the coded region.

The novel tyrosine kinase described herein has been found to be induced in denervated skeletal muscle. Accordingly, it has been designated as MuSK (muscle specific kinase). It has also been referred to previously as Dmk (denervated muscle kinase). In addition to being found in skeletal muscle, both normal and denervated, MuSK has also been found to be present in, but not be limited to, the spleen, ovary and retina. It appears to be present during early development, but is also found in adult tissue.

MuSK may be related to the Torpedo RTK identified by Jennings, et al. supra. However, MuSK differs in that it appears to be induced in denervated muscle, whereas no such induction has been reported with regard to the Torpedo RTK. Furthermore, the Torpedo RTK has an extracellular kringle domain, whereas MuSK does not. However, these kinases may be members of the same or related families.

The gene encoding rat MuSK has been cloned and the DNA sequence determined (FIGS. 1A–1D; SEQ ID NO: 2). The extracellular domain of the mature protein is believed to be encoded by the nucleotide sequence beginning on or around position 192 and ending on or around position 1610. The transmembrane portion of the protein is believed to be encoded by the nucleotide sequence beginning on or around position 1611 and ending on or around position 1697. The intracellular domain is believed to be encoded by the nucleotide sequence beginning on or around position 1698 and ending on or around position 2738. A cDNA clone encoding Dmk (MuSK) was deposited with the American Type Culture Collection on Jul. 13, 1993 and accorded an accession number of ATCC No. 75498.

The present invention also provides for a protein or peptide that comprises the extracellular domain of MuSK as well as the sequence of nucleotides which encode this extracellular domain. The extracellular domain of the protein is believed to be comprised of the amino acids at or around positions 20 through 492 of the coding region set forth as SEQ ID NO: 1.

The similarity between MuSK and the Torpedo RTK suggests the utilization of regions of sequence homologies within these genes to develop primers useful for searching for additional, related RTKs.

Accordingly, the invention provides for nucleic acids, or oligonucleotides greater than about 10 bases in length, that hybridize to the nucleic acid sequences described herein and that remain stably bound under stringent conditions. Stringent conditions as used herein are those which (1) employ low ionic strength and high temperature for washing, for example, 0.15M NaCl/0.015M sodium citrate/0.1% NaDodSO$_4$ at 50° C., or (2) use during hybridization of a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.

The present invention further provides for an isolated and purified nucleic acid molecule comprising a nucleotide sequence encoding human muscle specific kinase (MuSK) receptor, wherein the nucleotide sequence is selected from the group consisting of:

(a) the nucleotide sequence comprising the coding region of the human MuSK receptor as set forth in FIGS. 4A–4D (SEQ. ID. NOS. 28 and 29);

(b) a nucleotide sequence that hybridizes under stringent conditions to the nucleotide sequence of (a) and which encodes a human MuSK receptor; and (c) a nucleotide sequence that, as a result of the degeneracy of the genetic code, differs from the nucleotide sequence of (a) or (b) and which encodes a human MuSK receptor.

The invention further provides for isolated and purified human MuSK receptor encoded by the coding region of the human MuSK receptor nucleotide sequence as set forth above. The invention also provides for a vector which comprises the isolated nucleic acid molecule described. In one embodiment, the vector is an expression vector wherein the DNA molecule is operatively linked to an expression control sequence. In a further embodiment, the expression vector comprises an immediate early gene promoter. In a still further embodiment, the expression vector of the invention comprises the fos promoter or the jun promoter as the early gene promoter.

The invention further contemplates a host-vector system for the production of a polypeptide having the biological activity of a human MuSK receptor which comprises the vector described above in a suitable host cell. By way of nonlimiting example, a suitable host cell may be a C2C12 cell or an NIH3T3 cell. The invention further provides for a method of producing a polypeptide having the biological activity of human MuSK receptor which comprises growing cells of the above-described host-vector system under conditions permitting production of the polypeptide and recovering the polypeptide so produced.

In addition, the invention provides for a therapeutic composition comprising the MuSK receptor activating molecule in a pharmaceutically acceptable vehicle.

The invention also provides for an antibody which specifically binds the above-described MuSK receptor. The antibody of the invention may be a polyclonal or monoclonal antibody.

The invention further provides for a MuSK receptorbody comprising the extracellular portion of the above-described MuSK receptor, fused to an immunoglobulin constant region. In a preferred embodiment, the constant region of the receptorbody is the human immunoglobulin gamma-1 constant region (MuSK-IgG1 receptorbody).

The invention further provides a method of detecting the presence of MuSK ligand in a sample comprising:

a) reacting the sample with a MuSK receptorbody capable of specifically binding MuSK ligand under conditions whereby the MuSK receptorbody binds to MuSK ligand present in the sample; and b) detecting the bound MuSK receptorbody, thereby detecting the presence of MuSK ligand in the sample.

The MuSK receptorbody used is most preferably MuSK-IgG1 receptorbody. The sample may be biological tissue or body fluid. The biological tissue may be muscle, heart, spleen or ovary. The body fluid may be cerebrospinal fluid, urine, saliva, blood, or a blood fraction such as serum or plasma.

The invention also provides for a fibroblast cell line that is growth factor dependent in serum-free medium and that comprises a nucleic acid molecule encoding the human MuSK receptor as described above.

When using nucleotide sequences coding for part or all of MuSK in accordance with this invention to isolate new family members or MuSK from other species, the length of the sequence should be at least sufficient to be capable of hybridizing with endogenous mRNA from the vertebrate's own musk. Typically, sufficient sequence size will be about 15 consecutive bases (DNA or RNA).

Strategies for identifying novel RTKs using degenerate oligodeoxyribonucleotide primers corresponding to protein regions surrounding amino acids conserved in tyrosine kinases have been previously described (Wilks, et al., 1989, Proc. Natl. Acad. Sci. U.S.A., 86:1603–1607, Partanen, J. et al., 1990, Proc. Natl. Acad. Sci. U.S.A. 87: 8913–8917; Lai and Lemke, 1991, Neuron 6: 691–704; Masiakowski and Carroll, 1992, J. Biol. Chem. 267: 26181–26190). The discovery by applicants of the relationship between MuSK and the Torpedo RTK has led to the identification of heretofore unknown homology regions which may be used in screening strategies.

The following primer, based on the amino acid homology domain Asp-Val-Trp-Ala-Tyr-Gly (SEQ ID NO: 3) between MuSK and the Torpedo RTK, may be used in combination with additional primers that correspond to known homology regions characteristic of RTKs, to isolate related tyrosine kinases, e.g. other family members [all codes used herein representing amino acids and nucleotides are as set forth in 37 C.F.R. §1.822(b)]:

5'-GAATTCGAGCTCCCRWANGCCCANACRTC-3' (SEQ ID NO:4)

The additional primers that correspond to known homology regions characteristic of RTKs include the following:

5'
1) Asp-Leu-Ala-Thr-Arg-Asn (SEQ ID NO: 5)
 5'-TCTTGACTCGAGAYYTNGCNACNMGNAA-3' (SEQ ID NO: 6)
2) Asp-Leu-Ala-Ala-Arg-Asn (SEQ ID NO: 7)
 5'-TCTTGACTCGAGAYYTNGCNGCNMGNAA-3' (SEQ ID NO: 8)

3'
1) Asp-Val-Trp-Ser-Leu-Gly (SEQ ID NO: 9)
 3'-CTRCANACCWSNATRCCCTCGAGCTTAAG-5' (SEQ ID NO: 10)
2) Asp-Val-Trp-Ser-Phe-Gly (SEQ ID NO: 11)
 3'-CTRCANACCWSNAARCCCTCGAGCTTAAG-5' (SEQ ID NO: 12)
3) Asp-Val-Trp-Ser-Tyr-Gly (SEQ ID NO: 13)
 3'-CTRCANACCWSNRANCCCTCGAGCTTAAG-5' (SEQ ID NO:14)

Alternatively, regions of homology shared by MuSK and members of related families, such as the Trk family, may be used in strategies designed to isolate novel RTKs.

The present invention further provides for substantially purified protein molecules comprising the amino acid sequence substantially as set forth in FIGS. 1A–1D for MuSK (SEQ ID NO: 1) or functionally equivalent molecules. Functionally equivalent molecules include derivatives in which amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the invention are proteins or fragments or derivatives thereof which are differentially modified during or after translation, e.g., by glycosylation, proteolytic cleavage, linkage to an antibody molecule or other cellular ligand, etc.

The invention further contemplates the isolation of proteins that have substantial similarity to the MuSK protein described herein. Substantial similarity, as used herein, refers to proteins that are from different species or are family members within a species and are identical in at least 40% of positions. Substantial similarity at the protein level includes the ability of a subject protein to compete with MuSK for binding to monoclonal antibodies raised against MuSK epitopes.

The MuSK protein described herein is useful in 1) screening strategies, 2) purification strategies and 3) diagnostic uses. With respect to screening strategies, expression cloning strategies based on cell survival and proliferation assays provide a method of screening for cognate ligands (Glass, et al. (1991) Cell 66:405–413). Since ligands that bind MuSK may be membrane bound, other strategies for identification of such receptors may be more well suited (Armitage, et al. 1992, Nature 357:80–82; Smith, et al. 1993, Cell 73:1349–1360). In preferred embodiments, the extracellular domain of MuSK is fused to a marker to create a chimeric protein which enables identification and purification of the extracellular domain when bound to a cognate.

If, for example, the cognate ligand is membrane bound, as described in Smith, et al. supra, the extracellular portion of MuSK may be fused to truncated immunoglobulin heavy chains (Fc). The fusion product may then be used to identify cells expressing surface ligand that binds the receptor by, for example, flow cytometry. Alternatively, other tags, such as myc used to tag the extracellular domain of MuSK, may also be useful for the screening and purification of MuSK-binding ligands (Davis, et al. 1991, Science 253:59–63; Squinto, et al., 1990, Neuron 5:757–766).

In other embodiments, the extracellular portion of RTKs that bind known ligands are replaced with the extracellular portion of MuSK. Measurable effects, such as changes in phenotype or induction of early response genes, normally associated with binding of the known ligand to the receptor, can be used to screen for cognate ligands that induce comparable effects.

For example, a cell line bearing the introduced MuSK receptor or a chimeric protein comprising the extracellular domain of MuSK fused to the transmembrane domain and intracellular domain of another RTK (MuSK-chimeric receptor), as well as the parental cell line without the receptor can be exposed to any potential source of an agent that might work through the receptor. Any specific effects (e.g. on cell survival or proliferation) on the cell line bearing the receptor or chimera can be used to identify and eventually purify agents acting on that receptor. Once a particular receptor/ligand system is defined, a variety of additional specific assay systems can be utilized, for example, to search for additional agonists or antagonists of MuSK.

According to the invention, MuSK or a MuSK-RTK chimeric receptor, when introduced into cells that do not normally express this receptor, can be used to identify ligands that bind the receptor based on the distinguishable response of the cell. The present invention contemplates that the type of response elicited depends on the cell utilized, and not the specific receptor introduced into the cell. Thus, for example, expression of the MuSK receptor in PC12 pheochromocytoma cells may result in the differentiation of the PC12 cells upon exposure to a ligand that binds the receptor, whereas the same receptor in fibroblasts may mediate both survival and proliferation in response to a MuSK binding ligand. Appropriate cell lines can be chosen to yield a response of the greatest utility for the assay, as well as discovery of agents that can act on tyrosine kinase receptors. "Agents" refers to any molecule(s), including but not limited to peptide and non-peptide molecules, that will act in systems to be described in a receptor dependent manner.

One of the more useful systems to be exploited involves the introduction of the desired receptor into a growth factor dependent fibroblast cell line. Such a receptor which does not normally mediate proliferative responses may, following introduction into fibroblasts, nonetheless be assayed by a variety of well established methods used to quantitate effects of fibroblast growth factors (e.g. thymidine incorporation or other types of proliferation assays; see van Zoelen, 1990, "The Use of Biological Assays For Detection Of Polypeptide Growth Factors" in Progress in Factor Research, Vol. 2, pp. 131–152; Zhan and M. Goldfarb, 1986, Mol. Cell. Biol., Vol. 6, pp. 3541–3544). These assays have the added advantage that any preparation can be assayed both on the cell line having the introduced receptor as well as the parental cell line lacking the receptor. Only specific effects on the cell line with the receptor would be judged as being mediated through the introduced receptor.

A cell that expresses a receptor described herein may either naturally express the receptor or be genetically engineered to do so. For example, nucleotide sequences obtained as described herein may be introduced into a cell by transfection, transduction, microinjection, electroporation, via a transgenic animal, etc., using any method known in the art.

The specific binding of test agent to the receptor may be measured in a number of ways. For example, the binding of test agent to cells may be detected or measured, by detecting or measuring (i) test agent bound to the surface of intact cells; (ii) test agent cross-linked to receptor protein in cell lysates; or (iii) test agent bound to receptor in vitro. The specific interaction between test agent and the receptor may be evaluated by using reagents that demonstrate the unique properties of that interaction.

Alternatively, the specific activity of test agent on the receptor may be measured by evaluating the secondary biological effects of that activity, including, but not limited to, the induction of neurite sprouting, immediate early gene expression or phosphorylation of the receptor. For example, the ability of the test agent to induce neurite sprouting can be tested in cells that lack the receptor and in comparable cells that express, for example, a chimeric receptor comprising the MuSK extracellular domain and the intracellular domain of a member of the Trk family; neurite sprouting in receptor expressing cells but not in comparable cells that lack the receptor would be indicative of a specific test agent/receptor interaction. A similar analysis could be performed by detecting immediate early gene (e.g. fos and jun) induction in receptor-minus and receptor-plus cells, or by detecting phosphorylation of the receptor protein using standard phosphorylation assays known in the art.

Similarly, the present invention provides for a method of identifying an agent that has signal transducing activity comprising (i) exposing a cell that expresses a tyrosine kinase receptor as described herein to a test agent and (ii) detecting the activity of the test agent to the receptor, in which activity positively correlates with signal transducing activity. Activity may be detected by either assaying for direct binding or the secondary biological effects of binding, as discussed supra. Such a method may be particularly useful in identifying new neurotrophic factors or factors having other pharmaceutical activity such as cardioprotective activity, or may be useful in screening a large array of peptide and non-peptide agents (e.g., peptidomimetics) for such activities.

In a preferred, specific, nonlimiting embodiment of the invention, a large grid of culture wells may be prepared that contain, in alternate rows, PC12 (or fibroblasts, see infra) cells that are either receptor-minus or engineered to be receptor-plus. A variety of test agents may then be added such that each column of the grid, or a portion thereof, contains a different test agent. Each well could then be scored for the presence or absence of neurite sprouting. An extremely large number of test agents could be screened for signal transducing activity in this manner.

The present invention also provides for assay systems that may be used according to the methods described supra. Such assay systems may comprise in vitro preparations of receptor, e.g. affixed to a solid support, or may preferably comprise cells that express receptor proteins described herein.

The present invention further provides for host cells and microorganisms and vectors that carry the recombinant nucleic acid molecules described supra. Cells that express receptor protein may be genetically engineered to produce receptor as described supra, by transfection, transduction, electroporation, or microinjection of nucleic acid encoding MuSK in a suitable expression vector. In one embodiment, the host cell carrying the recombinant nucleic acid is an animal cell, such as COS. In another embodiment, the host cell is a bacterium, preferably *Escherichia coli*.

Any of the methods known to one skilled in the art for the insertion of DNA fragments into a vector may be used to construct expression vectors encoding receptor. These methods may include in vitro recombinant DNA and synthetic techniques and in vivo recombinations (genetic recombination). Expression of nucleotide sequence encoding the receptor protein or peptide fragment may be regulated by a second nucleotide sequence so that the receptor protein or peptide is expressed in a host transformed with the recombinant DNA molecule. For example, expression of receptor may be controlled by any promoter/enhancer element known in the art. Promoters which can be used to control receptor expression include, but are not limited to the long terminal repeat as described in Squinto et al., (1991, Cell 65:1–20); the SV40 early promoter region (Bernoist and Chambon, 1981, Nature 290:304–310), the CMV promoter, the M-MuLV 5' terminal repeat the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:144–1445), the regulatory sequences of the metallothioein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25). See also "Useful proteins from recombinant bacteria" in Scientific American, 1980, 242:74–94; promoter elements from yeast or other fungi such as the Gal 4 promoter, the ADH (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58); alpha 1-antitrypsin gene control region which is active in the liver (Kelsey et al, 1987, Genes and Devel. 1:161–171), beta-globin gene control region which is active in myeloid cells (Mogram et al., 1985, Nature 315:338–340; Kollias et al., 1986, Cell 46:89–94); myelin basic protein gene control region which is active in oligodendrocyte cells in the brain (Readhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

Expression vectors containing receptor-encoding gene inserts can be identified by three general approaches: (a) DNA-DNA hybridization, (b) presence or absence of "marker" gene functions, and (c) expression of inserted sequences. In the first approach, the presence of a foreign gene inserted in an expression vector can be detected by DNA-DNA hybridization using probes comprising sequences that are homologous to an inserted gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if the receptor-encoding gene is inserted within the marker gene sequence of the vector, recombinants containing the gene insert can be identified by the absence of the marker gene function. In the third approach, recombinant expression vectors can be identified by assaying the foreign gene product expressed by the recombinant vector. Such assays can be based, for example, on the physical or functional properties of the receptor-encoding gene product, for example, by binding of the receptor to neurotrophic factor or to an antibody which directly recognizes the receptor. Cells of the present invention may transiently or, preferably, constitutively and permanently express receptors or portions thereof.

In preferred embodiments, the present invention provides for cells that express receptors described herein or portions thereof and that also contain recombinant nucleic acid comprising an immediate early gene promoter [e.g. the fos or jun promoters (Gilman et al., 1986, Mol. Cell. Biol. 6:4305–4316)]. When such a cell is exposed to a ligand that binds to the receptor, the binding secondarily induces transcription off the immediate early promoter. Such a cell may be used to detect receptor/ligand binding by measuring the transcriptional activity of the immediate early gene promoter, for example, by nuclear run-off analysis, Northern blot analysis, or by measuring levels of a gene controlled by the promoter. The immediate early promoter may be used to control the expression of fos or jun or any detectable gene product, including, but not limited to, any of the known reporter genes, such as a gene that confers hygromycin resistance (Murphy and Efstratiadis, 1987, Proc. Natl. Acad. Sci. U.S.A. 84:8277–8281) chloramphenicol acetyltransferase (CAT), neomycin phosphotransferase (neo), beta-galactosidase beta-glucuronidase, beta-galactosidase, etc. of detecting or measuring neurotrophin activity.

Furthermore, the cells used in the assay systems of the invention may or may not be cells of the nervous system. For example, in a specific, nonlimiting embodiment of the invention, growth-factor dependent fibroblasts may be used as the basis for a signal transducing assay system. A fibroblast cell line that is growth factor dependent in serum-free media (e.g. as described in Zham and Goldfarb, 1986, Mol. Cell. Biol. 6:3541–3544) may be transfected with a receptor-encoding gene, for instance by using a $CaPO_4$ transfection protocol with 5 micrograms of DNA of CMV-promoter-based expression vector comprising the musk gene and one microgram of hygromycin-resistance gene-containing expression vector. After about 48 hours, the cells may then be selected for hygromycin resistance to identify positive transfectants. The cells may then be cultured for about three weeks in the presence of hygromycin,and then resistant colonies may be pooled. These cells may then be plated on tissue culture plates coated with poly-D-lysine and human fibronectin, and allowed to grow in DMEM plus 10% bovine calf serum for about four hours to allow the cells to bind to the plates. The serum-containing media may then be aspirated and the cells may be washed about three times with PBS to remove any residual serum. The cells may then be taken up with either serum free defined media (a 3:1 mixture of DMEM and Hams F12, supplemented with 8 mM sodium bicarbonate, 15 mM HEPES, $4\times10^{-6}$M $MnCl_2$, 3 mM histidine, $10^{-5}$M ethanolamine, $10^{-7}$M sodium selenite, 5 mg transferrin per liter, 200 mg bovine serum albumin-linoleic acid complex per liter gentamicin, penicillin, and streptomycin, 20 mM L-glutamine). Cells produced in this manner, then incubated with a factor capable of binding to MuSK may, after about 5 days in culture (replacing media and growth factors every 48 hours), be expected to be growing and proliferating; cells treated with an unrelated ligand at 100 ng/ml or in serum free-medium should not, however, proliferate.

Further insight into the physiological role of MuSK will come from the further definition of the activating molecule of the present invention. The kinase domain of the MuSK receptor appears to be related to other receptor tyrosine kinases, thus it is likely that the MuSK receptor is involved in signal transduction in cells in which it is expressed. Accordingly, the MuSK activating molecule of the present invention may be used to induce signal transduction not only in naturally occurring MuSK-expressing cells, which include cells found in the muscle tissue, heart, spleen, ovaries and retina, but also in cells engineered to express the MuSK receptor. The MuSK activating molecule of the present invention may be used to promote the growth or survival of such cells.

The term "MuSK activating molecule" as used herein refers to a molecule which is capable of inducing phosphorylation of the MuSK receptor in the context of a differentiated muscle cell. One such activating molecule is agrin as described in the Examples set forth herein.

As used herein, the term "MuSK activating molecule" includes the isolated and purified MuSK receptor activating polypeptides described herein, as well as functionally equivalent molecules in which amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the invention are proteins or fragments or derivatives thereof which exhibit the same or similar biological activity and derivatives which are differentially modified during or after translation, e.g., by glycosylation, proteolytic cleavage, linkage to an antibody molecule or other cellular ligand, etc.

The present invention also provides for use of the MuSK receptor or its extracellular or intracellular domain to screen for drugs that interact with or activate MuSK. Novel agents that bind to and/or activate the receptor described herein may mediate survival, proliferation and differentiation in cells naturally expressing the receptor, but also may mediate survival, proliferation or differentiation when used to treat cells engineered to express the receptor.

In particular embodiments, the extracellular domain (soluble receptor) of MuSK is utilized in screens for cognate ligands and activating molecules. For example, the MuSK receptor activating molecule described herein may be used in a competition assay to identify agents capable of acting as receptor agonists or antagonists by competing the agents with MuSK activating molecule for phosphorylation of the MuSK receptor. Specifically, the active portion of human agrin described herein may be used as the MuSK activating molecule in a competition assay to screen for agents capable of acting as receptor agonists or antagonists.

The present invention also provides for nucleic acid probes, capable of hybridizing with a sequence included within the nucleotide sequence encoding human MuSK or its activating molecule, useful for the detection of MuSK expressing tissue or MuSK activating molecule-expressing tissue in humans and animals. The invention further provides for antibodies capable of specifically binding MuSK or MuSK activating molecule. The antibodies may be polyclonal or monoclonal.

The present invention also has diagnostic and therapeutic utilities. In particular embodiments of the invention, methods of detecting aberrancies in the function or expression of the receptor described herein may be used in the diagnosis of muscular or other disorders. In other embodiments, manipulation of the receptor, agonists which bind this receptor, or receptor activating molecules may be used in the treatment of neurological diseases or diseases of muscle or neuromuscular unit disorders, including, but not limited to, muscular dystrophy and muscle atrophy. In further embodiments, the extracellular domain of the receptor is utilized as a blocking agent.

The present invention also provides for an isolated and purified polypeptide which activates MuSK receptor. In one embodiment, the polypeptide of the invention is encoded by a nucleotide sequence comprising the coding region of the active portion of human agrin contained in the vector designated as pBluescript human Agrin-1 (pBL-hAgrin1) that was deposited with the American Type Culture Collection on Dec. 12, 1995 under ATCC Accession No. 97378. The present invention further provides for an isolated polypeptide which is functionally equivalent to this polypeptide.

The invention further provides for an isolated and purified nucleic acid molecule comprising a nucleotide sequence encoding the active portion of human agrin, wherein the nucleotide sequence is selected from the group consisting of:

(a) the nucleotide sequence comprising the coding region of the active portion of human agrin contained in the vector designated as pBL-hAgrin 1 (ATCC Accession No. 97378);

(b) a nucleotide sequence that hybridizes under stringent conditions to the nucleotide sequence of (a) and which encodes the active portion of human agrin; and (c) a nucleotide sequence that, as a result of the degeneracy of the genetic code, differs from the nucleotide sequence of (a) or (b) and which encodes the active portion of human agrin.

The invention also provides for the above-described nucleic acid molecule which additionally contains a nucleotide sequence so that the encoded polypeptide contains the eight amino acids ELANEIPV at the position corresponding to amino acid position 1780 as shown in FIGS. 14A–14C (SEQ ID. NO. 30).

The invention further provides for an isolated and purified nucleic acid molecule comprising a nucleotide sequence encoding the active portion of human agrin, wherein the nucleotide sequence is selected from the group consisting of:

(a) the nucleotide sequence comprising the coding region of the active portion of human agrin as set forth in FIGS. 15A–15B (SEQ. ID. NOS. 31 and 32);

(b) a nucleotide sequence that hybridizes under stringent conditions to the nucleotide sequence of (a) and which encodes the active portion of human agrin; and (c) a nucleotide sequence that, as a result of the degeneracy of the genetic code, differs from the nucleotide sequence of (a) or (b) and which encodes the active portion of human agrin.

A further embodiment of the invention is an isolated and purified nucleic acid molecule encoding agrin 0-8 comprising a nucleotide sequence encoding the active portion of human agrin, wherein the nucleotide sequence is as set forth in FIGS. 15A–15B (SEQ. ID. NOS. 31 and 32) with the exception that there is no insert at position Y. Another embodiment of the invention is an isolated and purified nucleic acid molecule encoding agrin 4-0 comprising a nucleotide sequence encoding the active portion of human agrin, wherein the nucleotide sequence is as set forth in FIGS. 15A–15B (SEQ. ID. NOS. 31 and 32) with the exception that there is no insert at position Z.

The invention also provides for a method of promoting the growth or survival of a MuSK receptor expressing cell in culture comprising administering to the MuSK receptor expressing cell an effective amount of agrin or a derivative of agrin. In one embodiment of this method, the agrin is human agrin. In another embodiment of this method, the MuSK receptor expressing cell is a cell which is normally found in the heart, spleen, ovary or retina. In another embodiment, the MuSK receptor expressing cell is a cell which has been genetically engineered to express the MuSK receptor.

The present invention also includes a method of treating a patient suffering from a muscle disease or neuromuscular disorder comprising administering to the patient an effective amount of agrin or a derivative thereof. By way of non-limiting example, the agrin may be human agrin and the derivative may be the active portion of the human agrin molecule.

The present invention also includes an antibody capable of specifically binding human agrin. More specifically, the invention includes an antibody capable of specifically binding the active portion of human agrin. The antibody may be monoclonal or polyclonal. The invention further provides a method of detecting the presence of human agrin in a sample comprising:

a) reacting the sample with an antibody capable of specifically binding human agrin under conditions whereby the antibody binds to human agrin present in the sample; and b) detecting the bound antibody, thereby detecting the presence of human agrin in the sample.

The antibody used may be monoclonal or polyclonal. The sample may be biological tissue or body fluid. The biological tissue may be brain, muscle, or spinal cord. The body fluid may be cerebrospinal fluid, urine, saliva, blood, or a blood fraction such as serum or plasma.

The cDNA clone encoding the active portion of human agrin described herein will facilitate screening of cDNA and genomic libraries in order to clone the full length sequence coding for the entire human agrin molecule. Cells may be genetically engineered to produce the active portion or the full length agrin molecule by, e.g., transfection, transduction, electroporation, microinjection, via a transgenic animal, of a nucleotide sequence encoding the active portion or the full length agrin molecule in a suitable expression vector. The invention also provides for a vector comprising an isolated nucleic acid molecule encoding an active portion or the full length human agrin molecule.

The invention further provides for a host-vector system for the production in a suitable host cell of a polypeptide having the biological activity of human agrin. The suitable host cell may be a bacterial cell such as *E. coli.*, a yeast cell such as *Pichia pastoris*, an insect cell such as *Spodoptera frugiperda* or a mammalian cell such as a COS or CHO cell. The invention also provides for a method of producing a polypeptide having the biological activity of human agrin which comprises growing cells of the host-vector system under conditions permitting production of the polypeptide and recovering the polypeptide so produced.

The invention further provides for an expression vector comprising a nucleic acid molecule encoding human agrin, wherein the nucleic acid molecule is operatively linked to an expression control sequence. The invention also provides a host-vector system for the production of a polypeptide having the biological activity of human agrin which comprises the expression vector of the invention in a suitable host cell. The suitable host cell may be a bacterial cell such as *E. coli.*, a yeast cell such as *Pichia pastoris*, an insect cell such as *Spodoptera frugiperda* or a mammalian cell such as a COS or CHO cell. The invention further provides for a method of producing a polypeptide having the biological activity of human agrin which comprises growing cells of the host-vector system of the invention, under conditions permitting production of the polypeptide and recovering the polypeptide so produced.

As described above, the present invention relates to a tyrosine kinase receptor that appears to be expressed in denervated muscle. According to the present invention, probes capable of recognizing these receptors may be used to identify diseases or disorders by measuring altered levels of the receptor in cells and tissues. Such diseases or disorders may, in turn, be treatable using the activating molecule disclosed herein. Such disorders include but are not limited to those in which atrophic or dystrophic change of muscle is the fundamental pathological finding. For example, muscle atrophy can result from denervation (loss of contact by the muscle with its nerve) due to nerve trauma; degenerative, metabolic or inflammatory neuropathy (e.g. GuillianBarre syndrome), peripheral neuropathy, or damage to nerves caused by environmental toxins or drugs. In another embodiment, the muscle atrophy results from denervation due to a motor neuronopathy. Such motor neuronopathies include, but are not limited to: adult motor neuron disease, including Amyotrophic Lateral Sclerosis (ALS or Lou Gehrig's disease); infantile and juvenile spinal muscular atrophies, and autoimmune motor neuropathy with multifocal conduction block. In another embodiment, the muscle atrophy results from chronic disuse. Such disuse atrophy may stem from conditions including, but not limited to: paralysis due to stroke, spinal cord injury; skeletal immobilization due to trauma (such as fracture, sprain or dislocation) or prolonged bed rest. In yet another embodiment, the muscle atrophy results from metabolic stress or nutritional insufficiency, including, but not limited to, the cachexia of cancer and other chronic illnesses, fasting or rhabdomyolysis, endocrine disorders such as, but not limited to, disorders of the thyroid gland and diabetes. The muscle atrophy can also be due to a muscular dystrophy syndrome, including but not limited to the Duchenne, Becker, myotonic, Fascioscapulohumeral, Emery-Dreifuss, oculopharyngeal, scapulohumeral, limb girdle, and congenital types, and the dystrophy known as Hereditary Distal Myopathy. In a further embodiment, the muscle atrophy is due to a congenital myopathy, including, but not limited to Benign Congenital Hypotonia, Central Core disease, Nemaline Myopathy, and Myotubular (centronuclear) myopathy. In addition, MuSK and its associated ligand may be of use in the treatment of acquired (toxic or inflammatory) myopathies. Myopathies which occur as a consequence of an inflammatory disease of muscle, include, but not limited to polymyositis and dermatomyositis. Toxic myopathies may be due to agents, including, but are not limited to adiodarone, chloroquine, clofibrate, colchicine, doxorubicin, ethanol, hydroxychloroquine, organophosphates, perihexiline, and vincristine.

Although not wishing to be bound by theory, preliminary mapping of musk in the mouse has revealed that the gene is localized to mouse chromosome 4 in a region of homology with human chromosome 9q. Mutations in mice that are associated with this region of chromosome 4 include the "wi" mutation (whirler), which results in symptoms of the shaker syndrome, including deafness, head-tossing, circling and hyperactivity (Lane, P. W., 963, J. Hered. 54:263–266). Another mutation in mice that is associated with this region of chromosome 4 is the "vc" mutation (vacillans) which is associated with the symptoms of violent tremor when walking and with swaying of the hindquarters (Sirlin, J. L., 1956, J. Genet. 54:42–48).

In humans, the disease known as idiopathic torsion dystonia (ITD) is associated with a gene that has been mapped, through linkage analysis to human chromosome 9q band 34. This disease is characterized by sustained, involuntary muscle contractions, frequently causing twisting and repetitive movements or abnormal postures.

Should a defect in musk be found to be associated with these diseases, the present invention may prove useful in gene therapy for the replacement of such gene in situ. Alternatively, probes utilizing a unique segment of the musk gene may prove useful as a diagnostic for such disorders.

The present invention provides for a method of diagnosing a neurological or other disorder in a patient comprising comparing the levels of expression of MuSK in a patient sample with the levels of expression of MuSK in a comparable sample from a healthy person, in which a difference in the levels of expression of MuSK in the patient compared to the healthy person indicates that a disorder in the patient may be primarily or secondarily related to MuSK metabolism. A patient sample may be any cell, tissue, or body fluid but is preferably muscle tissue, cerebrospinal fluid, blood, or a blood fraction such as serum or plasma.

One variety of probe which may be used is anti-MuSK antibody or fragments thereof containing the binding domain of the antibody.

According to the invention, MuSK protein, or fragments or derivatives thereof, may be used as an immunogen to generate anti-MuSK antibodies. By providing for the production of relatively abundant amounts of MuSK protein using recombinant techniques for protein synthesis (based upon the MuSK nucleotide sequences of the invention), the problem of limited quantities of MuSK has been obviated.

To further improve the likelihood of producing an anti-MuSK immune response, the amino acid sequence of MuSK may be analyzed in order to identify portions of the molecule which may be associated with increased immunogenicity. For example, the amino acid sequence may be subjected to computer analysis to identify surface epitopes which present computer-generated plots of hydrophilicity, surface probability, flexibility, antigenic index, amphiphilic helix, amphiphilic sheet, and secondary structure of MuSK. Alternatively, the deduced amino acid sequences of MuSK from different species could be compared, and relatively non-homologous regions identified; these non-homologous regions would be more likely to be immunogenic across various species.

For preparation of monoclonal antibodies directed toward MuSK, or its activating molecule, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in "Monoclonal Antibodies and Cancer Therapy," Alan R. Liss, Inc. pp. 77–96) and the like are within the scope of the present invention.

The monoclonal antibodies for therapeutic use may be human monoclonal antibodies or chimeric human-mouse (or other species) monoclonal antibodies. Human monoclonal antibodies may be made by any of numerous techniques known in the art (e.g., Teng et al., 1983, Proc. Natl. Acad.

Sci. U.S.A. 80:7308–7312; Kozbor et al., 1983, Immunology Today 4:72–79; Olsson et al., 1982, Meth. Enzymol. 92:3–16). Chimeric antibody molecules may be prepared containing a mouse antigen-binding domain with human constant regions (Morrison et al., 1984, Proc. Natl. Acad. Sci. U.S.A. 81:6851, Takeda et al., 1985, Nature 314:452).

Various procedures known in the art may be used for the production of polyclonal antibodies to epitopes of MuSK. For the production of antibody, various host animals can be immunized by injection with MuSK protein, or a fragment or derivative thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

A molecular clone of an antibody to a MuSK epitope can be prepared by known techniques. Recombinant DNA methodology (see e.g., Maniatis et al., 1982, Molecular Cloning, A Laboratory Manual, Cold Spring Harbor Laboratory, Cold Spring Harbor, N.Y.) may be used to construct nucleotide sequences which encode a monoclonal antibody molecule, or antigen binding region thereof.

Antibody molecules may be purified by known techniques, e.g., immunoabsorption or immunoaffinity chromatography, chromatographic methods such as HPLC (high performance liquid chromatography), or a combination thereof, etc.

The present invention provides for antibody molecules as well as fragments of such antibody molecules. Antibody fragments which contain the idiotype of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

The above mentioned probes may be used experimentally to identify cells or tissues which hitherto had not been shown to express musk. Furthermore, these methods may be used to identify the expression of musk by aberrant tissues, such as malignancies. In additional embodiments, these methods may be used diagnostically to compare the expression of musk in cells, fluids, or tissue from a patient suffering from a disorder with comparable cells, fluid, or tissue from a healthy person. Fluid is construed to refer to any body fluid, but particularly blood, including blood fractions such as serum or plasma, or cerebrospinal fluid. A difference in the levels of expression of musk in the patient compared to a healthy person may indicate that the patient's disorder may be primarily or secondarily related to MuSK metabolism. An increase in levels of MuSK, for example, could either indicate that the patient's disorder is associated with an increased sensitivity to normal levels of MuSK-binding ligand or, alternatively, may suggest that the patient's MuSK-binding ligand levels are low such that the number of receptors is increased by way of compensation.

The present invention further provides for the use of soluble receptor (the extracellular domain) to counter the effect of ligand on MuSK expressing cells.

EXAMPLE 1

CLONING OF THE cDNA ENCODING MuSK

Tyrosine kinase homology domains were identified based on the alignments by Hanks et al. (1988) Science 241, 42–52. Highly conserved regions Asp-Leu-Ala-Ala-Arg-Asn (SEQ ID NO: 7) AND Asp-Val-Trp-Ser-Tyr-Gly (SEQ ID NO: 13) were used in designing the following degenerate oligonucleotide primers:

5'-TCTTGACTCGAGAYYTNGCNGCNMGNAA-3' (SEQ ID NO: 8)

5'-GAATTCGAGCTCCCRTANSWCCANACRTC-3' (SEQ ID NO: 15)

with which to prime PCR reactions using denervated muscle cDNAs. Resulting amplified DNA fragments were cloned by insertion into plasmids, sequenced and the DNA sequences were compared with those of all known tyrosine kinases. cDNA templates were generated by reverse transcription of denervated muscle tissue RNAs using oligo d(T) primers. PCR reactions were done at primer annealing temperatures of 40° C. Aliquots of the PCR reactions were subjected to electrophoresis on an agarose gel.

Size-selected amplified DNA fragments from these PCR reactions were cloned into plasmids as follows: Each PCR reaction was reamplified as described above, digested with XhoI and SacI to cleave sites in the termini of the primers (see below). XhoI/SacI-cut DNAs were purified by Magic PCR kit (from Promega) and cloned into compatible XhoI/SacI sites in the Bluescript II SK(+) plasmid, introduced into DH10B *E. coli* by electroporation, followed by plating of transformants on selective agar. Ampicillin-resistant bacterial colonies from PCR transformation were inoculated into 96-well microtiter plates and used for PCR using vector primers (T3 and T7) flanking the tyrosine kinase insert and these PCR fragments were analyzed by sequencing.

One of the cloned fragment sequences contained a segment of a novel tyrosine kinase domain, which was designated as MuSK. The sequence of the PCR-derived fragment corresponding to MuSK was used to generate PCR primers to obtain longer MuSK specific fragments by the RACE procedure. These longer MuSK probes were used as a hybridization probe to obtain full length MuSK cDNA clones from a rat denervated skeletal muscle cDNA library. DNA was sequenced by using the ABI 373A DNA sequencer and Taq Dyedeoxy Terminator Cycle Sequencing Kit (Applied Biosystems, Inc., Foster City, Calif.). The sequence of MuSK (FIGS. 1A–1D; SEQ ID NO:1) has a high degree of homology to members of the trk family of proteins. It was also found to be similar to the Jennings, et al. Torpedo RTK found in muscle.

Oligonucleotide primers corresponding to conserved regions of known tyrosine kinase molecules were used to amplify and clone DNA sequences encoding novel orphan tyrosine kinase receptor molecules. The amino acid sequences of representatives from branches of the tyrosine kinase family and regions of homology within the catalytic domain of these proteins were used to design degenerate oligonucleotide primers. These primers were then used to prime PCR reactions using as template a rat denervated muscle cDNA library. Resulting amplified DNA fragments were then cloned into Bluescript II SK(+) plasmid, sequenced, and the DNA sequences compared with those of known tyrosine kinases. The sequence of a PCR fragment encoding a novel tyrosine kinase named MuSK was used to obtain more adjoining DNA sequence. A DNA fragment containing MuSK sequences was used as a probe to obtain a cDNA clone from a denervated skeletal muscle library. This clone encodes a novel tyrosine kinase receptor with a high degree of homology to members of the trk family of proteins. It was also found to be homologous to the Jennings, et al. Torpedo RTK. FIGS. 1A–1D presents the nucleotide sequence (SEQ ID NO: 2) of the musk clone.

EXAMPLE 2

IDENTIFICATION OF ADDITIONAL TYROSINE KINASES

The novel MuSK sequence is used to obtain homology segments among receptor tyrosine kinases which can be used in combination with other homology segments. For example, an alignment of the Torpedo trk-related kinase with MuSK shows the following conserved protein segment:

Asp-Val-Trp-Ala-Tyr-Gly (SEQ ID NO: 3)

This homology "box" is not present in any other mammalian tyrosine kinase receptor. Degenerated oligonucleotides essentially based on this "box" in combination with either previously known or novel tyrosine kinase homology segments can be used to identify new tyrosine kinase receptors.

The highly conserved regions between MuSK and Torpedo TRK Asp-Val-Trp-Ala-Tyr-Gly (SEQ ID NO: 3) as well as additional primers based on known regions of homology, such as SEQ ID NOS. 5, 7, 9 OR 11, are used in designing degenerate oligonucleotide primers with which to prime PCR reactions using cDNAs. cDNA templates are generated by reverse transcription of tissue RNAs using oligo d(T) or other appropriate primers. Aliquots of the PCR reactions are subjected to electrophoresis on an agarose gel. Resulting amplified DNA fragments are cloned by insertion into plasmids, sequenced and the DNA sequences are compared with those of all known tyrosine kinases. Size-selected amplified DNA fragments from these PCR reactions are cloned into plasmids as follows. Each PCR reaction is reamplified as described above in Example 1, digested with XhoI and SacI to cleave sites in the termini of the primers (see below). XhoI/SacI-cut DNAs are cloned into compatible XhoI/SacI sites in a plasmid, introduced into E. coli by electroporation, followed by plating of transformants on selective agar. Ampicillin-resistant bacterial colonies from PCR transformation are inoculated into 96-well microtiter plates and individual colonies from these PCR clones are analyzed by sequencing of plasmid DNAs that are purified by standard plasmid miniprep procedures.

Cloned fragments containing a segment of a novel tyrosine kinase domain are used as hybridization probes to obtain full length cDNA clones from a cDNA library.

EXAMPLE 3

TISSUE SPECIFIC EXPRESSION OF MuSK

A 680 nts fragment, containing the tyrosine kinase domain of MuSK, was radiolabeled and utilized in Northern analysis of various rat tissue specific RNAs. The rat tissue specific RNAs were fractionated by electrophoresis through a 1% agarose-formaldehyde gel followed by capillary transfer to a nylon membrane with 10× SSC. The RNAs were cross-linked to the membranes by exposure to ultraviolet light and hybridized at 65° C. to the radiolabeled MuSK probe in the presence of 0.5M NaPO4 (pH 7), 1% bovine serum albumin (Fraction V, Sigma), 7% SDS, 1 mM EDTA and 100 ng/ml sonicated, denatured salmon sperm DNA. The filter was washed at 65° C. with 2× SSC, 0.1% SDS and subjected to autoradiography for 5 days with one intensifying screen and X-ray film at −70° C. Ethidium bromide staining of the gel demonstrated that equivalent levels of total RNA were being assayed for the different samples.

Figure 3:
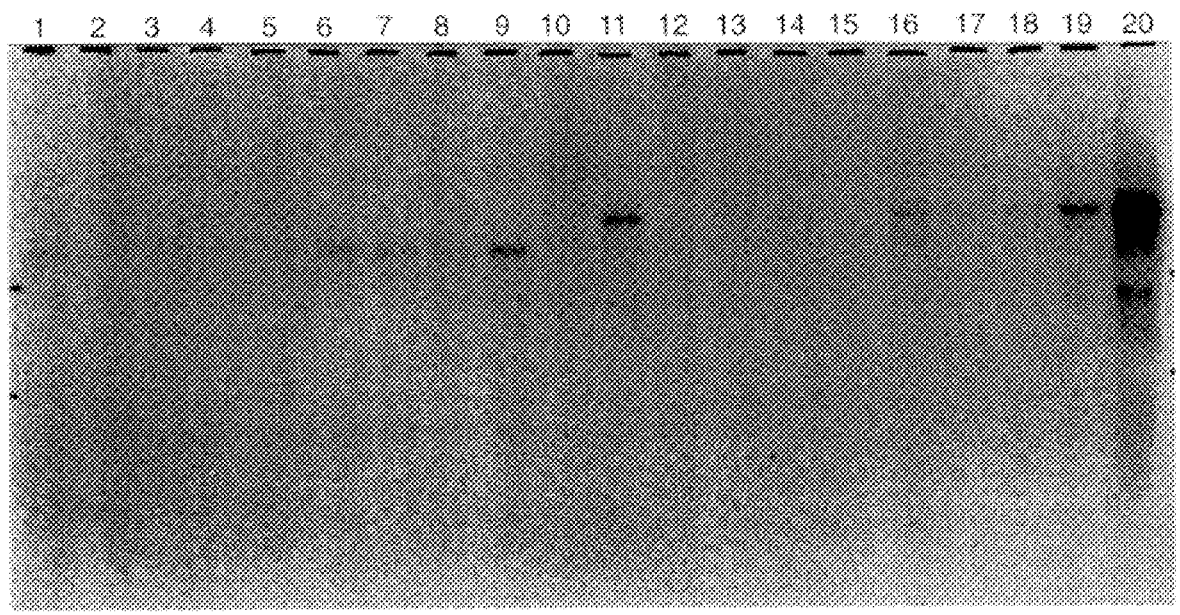
FIG. 3 Northern blot showing distribution of musk in adult rat tissues. Lane 1: Brain; Lane 2: Olfactory bulb; Lane 3: Cortex; Lane 4: Hippocampus; Lane 5: Thalamus/hypothalamus; Lane 6: Midbrain; Lane 7: Hindbrain; Lane 8: Cerebellum; Lane 9: Spinal Cord; Lane 10: Thymus; Lane 11: Spleen; Lane 12: Liver; Lane 13: Kidney; Lane 14: Lung; Lane 15: Sciatic Nerve; Lane 16: Retina; Lane 17: Heart; Lane 18: Ovary; Lane 19: Muscle; Lane 20: Denervated muscle.

The MuSK probe hybridized strongly in adult rat tissue (FIG. 3) to a 7 kb transcript from denervated skeletal muscle, and weakly to normal muscle, retina, ovary, heart and spleen. Weaker levels of expression could also be found in liver, kidney and lung. It also hybridizes weakly to a shorter MuSK transcript of about 6 kb in brain, spinal cord and cerebellum.

In embryonic tissue (FIG. 2), MuSK transcripts can be found in body, spinal cord, placenta and head at E12 and E 13.

The high expression of MuSK in muscle and neural tissue suggests that the present invention may be utilized to treat disorders of the nervous system, specifically the wide array of neurological disorders affecting motor neurons (see discussion, supra) and the neuromuscular junction. Additionally, high expression of MuSK in heart tissue suggests that the present invention may be utilized to treat heart disease, and may, for example, have prophylactic use in preventing muscle loss during or following a cardiac event. (see discussion, supra). Expression of MuSK in retinal tissue suggests that the present invention may be utilized to treat retina related disorders, including but not limited to retinitis pigmentosa. Expression of MuSK in ovaries suggests that MuSK or the ligand associated with MuSK may be useful in the treatment of diseases or disorders involving the ovaries. Finally, expression of MuSK in spleen suggests that MuSK or the ligand associated with MuSK may be useful in the treatment of diseases or disorders involving the spleen.

EXAMPLE 4

CLONING AND EXPRESSION OF MuSK RECEPTORBODY FOR AFFINITY-BASED STUDY OF MuSK LIGAND INTERACTIONS

An expression construct was created that would yield a secreted protein consisting of the entire extracellular portion of the rat MuSK receptor fused to the human immunoglobulin gamma-1 constant region (IgG1 Fc). This fusion protein is called a Dmk or MuSK "receptorbody" (RB), and would be normally expected to exist as a dimer in solution based on formation of disulfide linkages between individual IgG1 Fc tails. The Fc portion of the MuSK RB was prepared as follows. A DNA fragment encoding the Fc portion of human IgG1 that spans from the hinge region to the carboxy-terminus of the protein, was amplified from human placental cDNA by PCR with oligonucleotides corresponding to the published sequence of human IgG1; the resulting DNA fragment was cloned in a plasmid vector. Appropriate DNA restriction fragments from a plasmid encoding MuSK receptor and from the human IgG1 Fc plasmid were ligated on either side of a short PCR-derived fragment that was designed so as to fuse, in-frame, the MuSK and human IgG1 Fc protein-coding sequences. Thus, the resulting MuSK ectodomain-Fc fusion protein precisely substituted the IgG1 Fc in place of the region spanning the MuSK transmembrane and cytoplasmic domains. An alternative method of preparing receptorbodies is described in Goodwin, et. al. Cell 73: 447–456 (1993).

Milligram quantities of MuSK RB were obtained by cloning the MuSK RB DNA fragment into the pVL1393 baculovirus vector and subsequently infecting the Spodoptera frugiperda SF-21AE insect cell line. Alternatively, the cell line SF-9 (ATCC Accession No. CRL-1711) or the cell line BTI-TN-5b1-4 may be used. DNA encoding the MuSK RB was cloned as an Eco RI-NotI fragment into the baculovirus transfer plasmid pVL1393. Plasmid DNA purified by cesium chloride density gradient centrifugation was recombined into viral DNA by mixing 3 mg of plasmid DNA with 0.5 mg of Baculo-Gold DNA (Pharminigen), followed by introduction into liposomes using 30 mg Lipofectin (GIBCO-BRL). DNA-liposome mixtures were added to SF-21AE cells (2×106 cells/60 mm dish) in TMN-FH medium (Modified Grace's Insect Cell Medium (GIBCO-BRL) for 5 hours at 27° C., followed by incubation at 27° C. for 5 days in TMN-FH medium supplemented with 5% fetal calf serum. Tissue culture medium was harvested for plaque purification of recombinant viruses, which was carried out using methods previously described (O'Reilly, D. R., L. K. Miller, and V. A. Luckow, Baculovirus Expression Vectors- A Laboratory Manual. 1992, New York: W. H. Freeman) except that the agarose overlay contained 125 mg/mL X-gal (5-bromo-4-chloro-3-indolyl-b-D-galactopyranoside; GIBCO-BRL). After 5 days of incubation at 27° C., non-recombinant plaques were scored by positive chromagenic reaction to the X-gal substrate, and their positions marked. Recombinant plaques were then visualized by addition of a second overlay containing 100 mg/mL MTT (3-[4,5-dimethylthiazol-2-yl] 2,5,diphenyltetrazolium bromide; Sigma). Putative recombinant virus plaques were picked by plug aspiration, and purified by multiple rounds of plaque isolation to assure homogeneity. Virus stocks were generated by serial, low-multiplicity passage of plaque-purified virus. Low passage stocks of one virus clone (vMuSK receptor body) were produced.

SF-21AE cells were cultured in serum free medium (SF-900 II, Gibco BRL) containing 1× antibiotic/antimycotic solution (Gibco BRL) and 25 mg/L Gentamycin (Gibco BRL). Pluronic F-68 was added as a surfactant to a final concentration of 1 g/L. Cultures (4 L) were raised in a bioreactor (Artisan Cell Station System) for at least three days prior to infection. Cells were grown at 27° C., with gassing to 50% dissolved oxygen, at a gas flow rate of 80 mL/min (aeration at a sparge ring). Agitation was by means of a marine impeller at a rate of 100 rpm. Cells were harvested in mid-logarithmic growth phase (~2×10$^6$ cells per mL), concentrated by centrifugation, and infected with 5 plaque forming units of vMuSK Receptor Body per cell. Cells and inoculum were brought to 400 mL with fresh medium, and virus was adsorbed for 2 hours at 27° C. in a spinner flask. The culture was then resuspended in a final volume of 8 L with fresh serum-free medium, and the cells incubated in the bioreactor using the previously described conditions.

Culture medium from vMuSK Receptor Body-infected SF21AE cells were collected by centrifugation (500× g, 10 minutes) at 72 hours post-infection. Cell supernatants were brought to pH 8 with NaOH. EDTA was added to a final concentration of 10 mM and the supernatant pH was readjusted to 8. Supernatants were filtered (0.45 mm, Millipore) and loaded on a protein A column (protein A sepharose 4 fast flow or HiTrap protein A, both from Pharmacia). The column was washed with PBS containing 0.5M NaCl until the absorbance at 280 nm decreased to baseline. The column was washed in PBS and eluted with 0.5M acetic acid. Column fractions were immediately neutralized by eluting into tubes containing 1M Tris pH 9. The peak fractions containing the MuSK RB were pooled and dialyzed versus PBS. Recombinant *Autographa californica* baculovirus encoding the Dmk (MuSK) RB was designated "vDmk receptorbody" and deposited with the American Type Culture Collection, 12301 Parklawn Drive, Rockville, Md. 20852 on May 16, 1995 under ATCC Accession No. VR-2507.

EXAMPLE 5

SEQUENCING OF HUMAN MuSK RECEPTOR

In order to obtain the full coding sequence of the human MuSK receptor, oligonucleotides based on the rat sequence were utilized as PCR primers to amplify cDNA from a human muscle biopsy. The PCR fragment so produced was then sequenced and the resulting new sequence corresponded to a partial sequence of the human MuSK receptor. The novel partial human MuSK receptor sequence was then used to obtain further sequence through successive rounds of the RACE procedure. (Frohman, M. A. (1990), RACE: Rapid amplification of cDNA ends. in PCR Protocols, Innis, M. A. Gelfand, D. H., Snincky, J. J., and White, T. J. eds. Academic Press. San Diego ).

This process was complemented by obtaining human genomic clones of MuSK and using the coding sequence of the genomic MuSK to design oligonuclotide primers used to amplify the biopsy cDNA. Stretches of the human MuSK cDNA sequence which were difficult to sequence, absent or presenting some ambiguity were confirmed, corrected or added from the human genomic MuSK sequence. MuSK cDNA variants produced by alternative splicing of MuSK transcripts may be obtained by using this sequence to obtain MuSK cDNA from human sources. The deduced amino acid sequence of the human MuSK receptor and the nucleotide sequence encoding it is set forth in FIGS. 4A–4D (SEQ. ID. NOS. 28 and 29). One of skill in the art will readily recognize that this sequence may be used to clone full length, naturally occurring cDNA sequences encoding the human MuSK receptor, which may vary slightly from the sequence set forth in FIGS. 4A–4D (SEQ. ID. NOS. 28 and 29).

EXAMPLE 6

HOMOLOGOUS RECOMBINATION TO DISRUPT THE MuSK GENE

Figure 5:
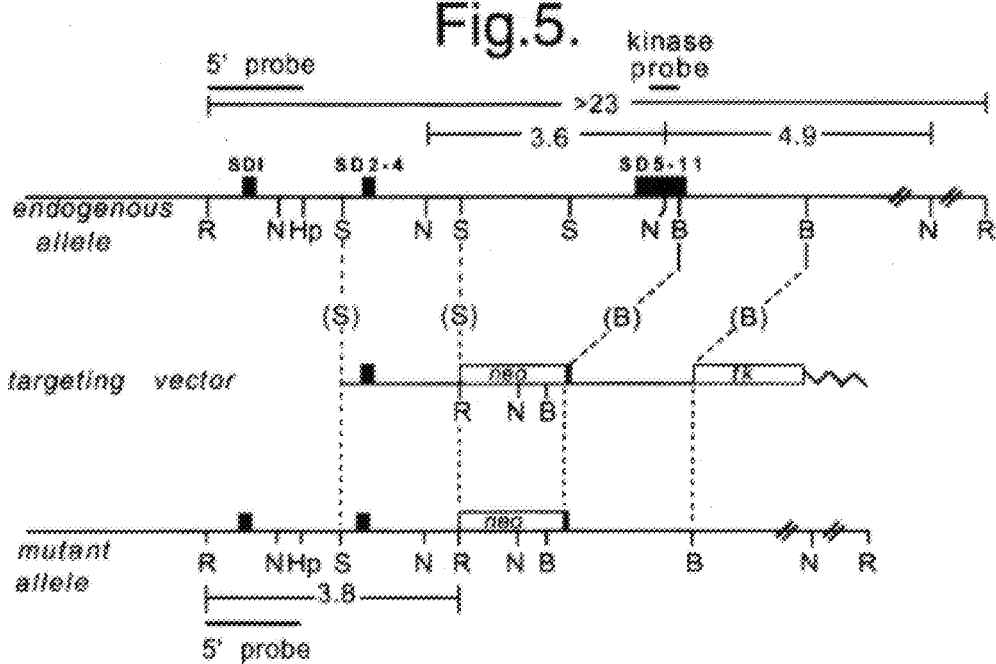
FIG. 5 Schematic representation of genomic DNA encompassing the three kinase domain exons of the mouse MuSK gene, of the targeting vector constructed, and of a mutant locus following successful targeting. The three exons of the MuSK kinase domain are indicated as black boxes, containing the indicated kinase subdomains (SD). The PGK-neo and MC1-tk cassettes are indicated as open boxes. The novel EcoRI (R) and NcoI (N) fragments generated following successful targeting are labeled. The 5' EcoRI/HpaI probe used to detect the endogenous and mutant EcoRI fragments was derived from genomic DNA not included in the targeting construct. B, BamHI; Hp, HpaI; S, SpeI (sites included within parentheses are destroyed in the cloning process).

The tyrosine kinase domain of MuSK is comprised of 11 subdomains that are divided among three coding exons. Subdomain I encoding the ATP-binding domain is located on the first kinase exon, while subdomains 5–11 encoding the catalytic region are located on the third kinase exon (FIG. 5). To disrupt MuSK tyrosine kinase activity, a targeting vector was designed that would delete most of the third kinase exon upon homologous recombination into the endogenous mouse MuSK locus (FIG. 5); this targeting vector contained a total of 3.8 kb of homology with the mouse MuSK gene.

The MuSK gene targeting vector was constructed from mouse genomic DNA fragments isolated from a lambda FIX II phage library prepared with 129 strain mouse genomic DNA (Stratagene). The 1.7 kb SpeI fragment depicted in FIG. 5 was ligated into the compatible ends of a unique XbaI site upstream of the PGK-neo cassette (destroying the SpeI and XbaI sites), while the 2.1 kb BamHI DNA fragment depicted in FIG. 5 was blunt-end ligated into the unique HindIII site between the PGK-neo cassette and MC1-tk expression cassettes (destroying the BamHI and HindIII sites). The targeting vector was linearized by digestion with NotI and then electroporated into E14.1 embryonic stem cells, which were subjected to a double selection protocol (gancyclovir addition resulted in a 5–10 fold enrichment compared with selection in G418 alone) and then used to generate chimeric mice as previously described (Conover et al., 1995; DeChiara et al., 1995).

Successful gene targeting using this construct was predicted to result in the generation of a novel 3.8 kb EcoRI fragment from the targeted allele as detected by a 5' probe, as well as loss of two NcoI fragments hybridizing to a kinase probe (FIG. 5). Southern blot screening for these fragments revealed that successful targeting of the mouse MuSK gene was achieved in four of approximately 400 embryonic stem (ES) cell clones obtained using a double selection scheme intended to enhance for selection of targeted clones; the ES cells were derived from the 129 strain of mice. Male chimeras derived from all four of these targeted clones were bred with C57BL/6 females. Chimeras from two of the targeted clones transmitted the mutant allele to the F1 generation. The resulting F1 progeny heterozygous for the MuSK mutation were viable and appeared normal and fertile.

EXAMPLE 7

MuSK GENE DISRUPTION RESULTS IN PERINATAL LETHALITY

Figure 6:
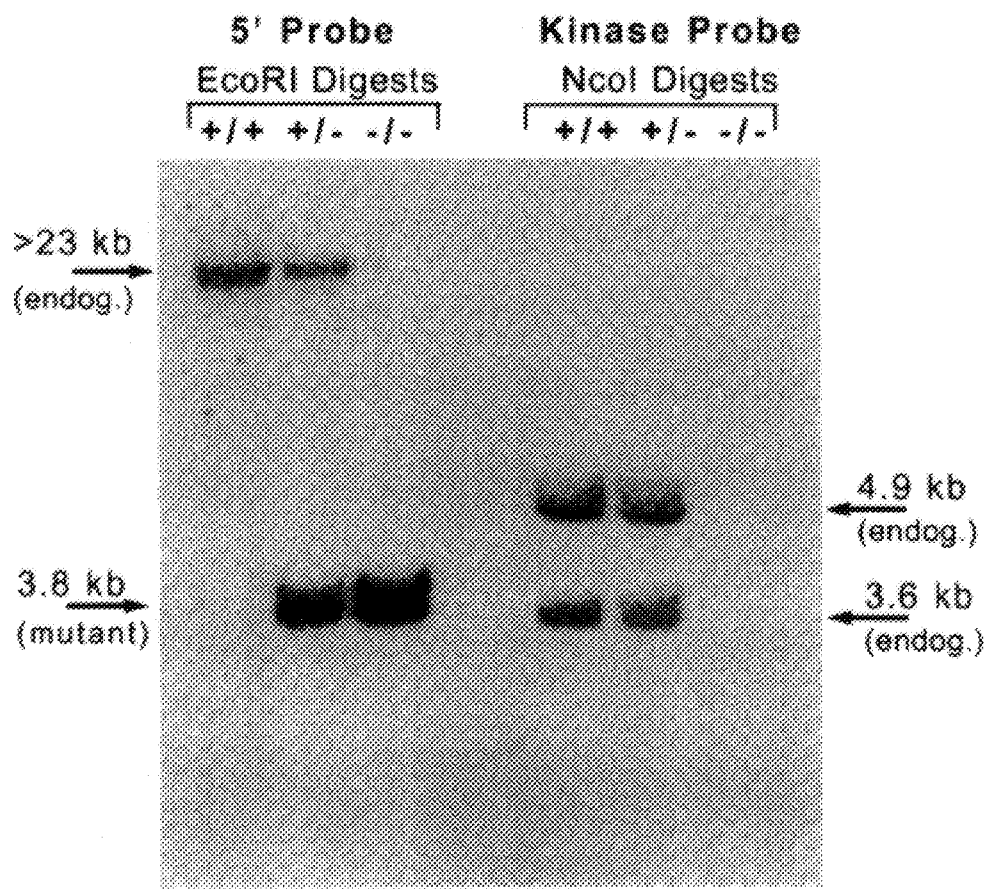
FIG. 6 MuSK Knockout Mice—Southern blot of tail DNA from wild-type, heterozygous and homozygous F2 progeny showing the endogenous and mutant EcoRI fragments detected by the 5' RI/HpaI probe, as well as the endogenous NcoI fragments detected by the kinase region probe, which are absent in the homozygous mutant.

The heterozygous F1 progeny were interbred to generate mice homozygous for the MuSK gene disruption (designated MuSK-/- mice). Among the F2 litters derived from these crosses were newborn mice that died perinatally. Genotype analysis of tail DNA mice revealed that the dead pups were homozygous for the mutant MuSK allele (FIG. 6); significantly, not a single mouse homozygous for the mutation survived the perinatal period (37 homozygotes were noted among the first 138 pups that were genotyped, corresponding to a 26.8% frequency of homozygotes).

To determine the phenotype of the MuSK-/- newborns immediately at birth, applicants were careful to observe the births of several litters derived from heterozygote crosses. Though normal in their gross anatomy and body weight, the MuSK-/- pups differed in several striking ways from their littermate controls. First, they showed no spontaneous movement and did not respond to a mild tail or leg pinch. Only a strong tail pinch was able to elicit a weak uncoordinated movement. By contrast, littermate controls showed extensive movement and responded vigorously to a mild tail pinch. Second, the MuSK-/- pups were cyanotic at birth and appeared not to breathe, although their hearts continued to beat for a short time after birth. To determine whether the MuSK-/- pups had ever taken a breath, applicants examined the lungs histologically. Lung alveoli are collapsed in utero, and expand with the first breath of life; even if respiration is then terminated, the alveoli remain expanded.

Figure 7A:
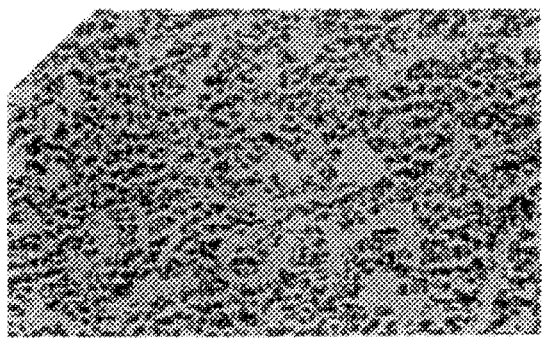
FIGS. 7A–7D Post-mortem histological analysis of lung demonstrating that the alveoli air sacs in the MuSK$^{-/-}$ newborn are not expanded (FIG. 7A) as they are in the lung of the control littermate (FIG. 7B), indicating that mutant pups do not take a single breath. Post-mortem histological analysis of hindlimb musculature reveals that MuSK$^{-/-}$ mice (FIG. 7C) possess grossly normal muscle architecture similar to that of control mice (FIG. 7D).
Figure 7B:
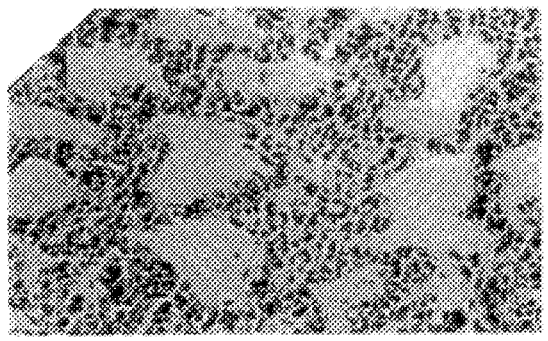

Histological examination (FIG. 7A) revealed that the alveoli of MuSK-/- pups were not expanded, indicating that the pups had never taken a breath. In contrast, the lungs of the littermate controls displayed expanded alveoli (FIG. 7B).

EXAMPLE 8

NORMAL SKELETAL MUSCLE IN MuSK-/- MICE

Because MuSK is localized to synaptic sites in skeletal muscle (Valenzuela, D., et al., 1995, Neuron 15: 573–584) and because MuSK-/- mutant mice are immobile at birth and die shortly thereafter, applicants reasoned that neuromuscular synapse formation might be aberrant in MuSK-/- mutants. Applicants first examined the diaphragm muscle because its simple organization and thin structure allows synaptic sites to be visualized in whole-mount preparations. The diaphragm muscle is innervated by the phrenic nerve, which normally enters near the center of the diaphragm muscle. The main intramuscular nerve is oriented perpendicular to the long axis of the muscle fibers and extends through the central region of the muscle.

For whole-mount diaphragm preparations newborn mice were fixed in 1% paraformaldehyde in phosphate-buffered saline (PBS) at 4° C. for several hours and then rinsed briefly in PBS. Diaphragm muscles were dissected out, washed twice for 10 minutes in PBS, incubated in 0.1M glycine in PBS for 15 minutes, rinsed for 5 minutes in PBS, and permeabilized with 0.5% Triton X-100 in PBS (PBT) for 5 minutes. The muscles were then incubated with rabbit antibodies to synaptophysin (kindly provided by Dr. R. Jahn, Yale University Medical School), which were diluted 1/1000 in PBT with 2% BSA, overnight at 4° C., subsequently rinsed for 5 minutes in PBT, washed three times for one hour in PBT and then incubated simultaneously with flourescein-conjugated sheep anti-rabbit IgG (Boehringer Mannheim) and tetramethlyrhodamine-conjugated α-bungarotoxin (α-BGT) (Molecular Probes, Oregon) overnight at 4° C. The tissues were then washed three times for 1 hour with PBT, rinsed once with PBS for 5 minutes, fixed in 100% methanol at −20° C. and mounted in 90% glycerol, 0.1M Tris, pH 7.5 with 1 mg/ml p-phenylenediamine. The whole-mounts were viewed with epiflourescence and filters that were selective for rhodamine or flourescein, and images were recorded either on film or on a CCD camera (Princeton Instruments).

Figure 7C:
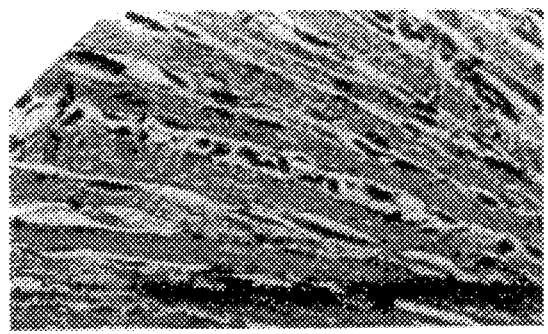
Figure 7D:
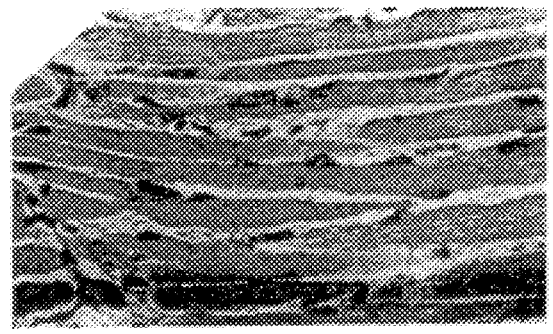

The arrangement and gross structure of the muscle fibers (compare FIG. 7C and 7D), as well as of the main intramuscular nerve, appeared to be unaltered in MuSK-/- mutant mice. Thus, although the onset of MuSK expression occurs at about embryonic day 11 in developing mouse somites (within the presumptive myotome), MuSK does not appear to be essential for the generation, proliferation and fusion of myoblasts, or for the growth of motor axons from spinal cord to muscle.

EXAMPLE 9

AGRIN FAILS TO INDUCE AChR CLUSTERING IN MYOTUBES LACKING MuSK

The localization of MuSK to the NMJ inspired us to ask whether MuSK is required for responsivity to agrin. To test this, applicants first isolated myoblasts from newborn MuSK-/- mice or from control pups, attempted to differentiate them into myotubes in culture, and then assayed for their responsiveness to agrin.

Primary myoblast cultures were established from hind limb musculature of newborn MuSK-/- or littermate control pups. This tissue was treated sequentially with collagenase and trypsin, then plated onto plastic tissue culture dishes. After 1 hour, non-adherent cells (principally myoblasts) were removed and plated onto chamber slides coated with poly-D-lysine and fibronectin. Myoblast cultures were maintained in Dulbecco's Modified Eagle's Medium (DMEM) containing 25% fetal calf serum, 10% horse serum, and 50 μg/ml gentamycin. To induce myotube formation, cultures were switched to a medium consisting of DMEM containing 5% horse serum, L-glutamine and gentamycin to which 20 μM cytosine arabinoside was added after 24 hr. After an additional 2–3 days, contractile myotubes had formed abundantly in cultures from both MuSK-/- and control pups. C2C12 cells were maintained and caused to differentiate in a serum-poor medium as previously described (Ferns, M., et al., 1993, Neuron 11: 491–502).

For agrin-mediated AChR clustering assays on primary myotubes, cultures on chamber slides were treated overnight with c-agrin4,8 at 0.01–100 nM; for evaluating MuSK-Fc as an inhibitor of clustering, differentiated C2C12 cells, on chamber slides coated with fibronectin and poly-D-lysine, were pretreated with MuSK-Fc or a control receptor-body for 1 hr at 37° C. before addition of approximately 10 nM agrin4,8 for overnight incubation. Following overnight treatments with agrin, the cells were next incubated in rhodamine-conjugated α-bungarotoxin to label AChRs, then fixed and mounted for fluorescence microscopy. To quantify the extent of AChR clustering, randomly selected myotubes were viewed under fluorescein optics, then switched to rhodamine optics and the number of AChR clusters within a reticule grid aligned along the long axis of the myotube were counted. AChRs on the surface of cultured primary myotubes were quantitated by incubating live cultures with 25 mCi 125I-α-BGT for 1 hr at room temperature, washing, and then lysing the cells in 0.1N NaOH. The protein concentration in aliquots of each extract was determined using a BCA protein assay kit (Pierce),while the remainder of the extract was counted in a gamma counter.

Myoblasts from both the control and MuSK−/− mice were able to fuse and form long, twitching myotubes in culture. Together with the observation that skeletal muscle appears rather normal in MuSK−/− mice, these findings indicate that MuSK is not critical for early muscle development and myoblast fusion. On the other hand, MuSK appeared to be absolutely required for AChR clustering in response to agrin. After stimulation with the most active form of c-agrin, containing both the four and eight amino acid insertions (c-agrin$_{4,8}$), AChR clusters were evident only in the myotubes from control mice (FIG. 8A). While clusters were induced in normal myotubes with as little as 1 nM c-agrin$_{4,8}$, no clustering was observed in MuSK−/− myotubes even after increasing the concentration of c-agrin$_{4,8}$ to as high as 100 nM (FIG. 8B). Lack of detectable clustering was not due to the absence of AChRs, since myotubes from MuSK−/− mice expressed similar numbers of AChR on their surface as did myotubes from control mice (FIG. 8C). Thus MuSK appeared to be absolutely required for AChR clustering in response to agrin.

EXAMPLE 10

AGRIN INDUCES PROMINENT AND RAPID TYROSINE PHOSPHORYLATION OF MuSK

The inability of agrin to induce AChR clustering in myotubes from MuSK−/− mice demonstrates that MuSK is required for agrin responsiveness, and is consistent with the possibility that MuSK serves as the functional agrin receptor. However, since clustering occurs over a period of hours, these results are also consistent with the possibility that MuSK acts much further downstream in the agrin signaling pathway. To begin to distinguish between these possibilities, applicants took advantage of the fact that RTKs become rapidly autophosphorylated on tyrosine upon challenge with their cognate ligand. Applicants decided to assay four of the known forms of soluble agrin—which exhibit differing AChR clustering activities (Ruegg, M. A. et al., 1992, Neuron 8: 691–699; Ferns, M., et al., 1992, Neuron 8: 1079–1086; Ferns, M., et al., 1993, Neuron 11: 491–502; Hoch, W. et al., 1994, EMBO J. 13: 2814–2821)—for their ability to induce phosphorylation of the MuSK receptor.

The ability of various agrins and growth factors to induce MuSK or ErbB3 tyrosine phosphorylation, for the indicated times and at the indicated concentrations, was evaluated in primary rat myoblasts and in either untransfected C2C12 myoblasts, or in C2C12 myoblasts stably transfected with a chick MuSK-expressing plasmid. The cells were challenged at confluence in an undifferentiated state, or approximately 4–5 days after being induced to differentiate into myotubes in serum-poor media. After challenge, the cells were lysed, the extracts subjected to immunoprecipitation with receptor-specific antibodies, and then immunoblotted with either receptor-specific or phosphotyrosine-specific antibodies, using methods previously described (Stitt, T., et al., 1995, Cell 80: 661–670). Polyclonal antibodies for MuSK were generated as follows: for rat MuSK, rabbits were immunized with a peptide corresponding to the carboxy-terminal 20 amino acids of the rat MuSK protein (Valenzuela, D., et al., 1995, Neuron 15: 573–584; the nomenclature for this antibody is: 41101K); for chick MuSK, rabbits were immunized with a peptide corresponding to the first 19 amino acids of the chick MuSK cytoplasmic domain (Peptide: TLPSELLL-DRLHPNPMYQ (SEQ. ID. NO. 16); the nomenclature for this antibody is 52307K). The specificity of the antibodies was determined on Cos-cell expressed MuSK proteins, by both immune-precipitation and Western, comparing untransfected Cos cell lysates to lysates from rat and chicken-MuSK transfected Cos cells. 41101K immune precipitates and Westerns rodent MuSK, but does not recognize chicken MuSK. 52307 immune precipitates and Westerns chicken MuSK. Antibodies to ErbB3 were obtained from Santa Cruz Biotechnology, Inc.

Cultures of confluent C2C12 cells, either undifferentiated or differentiated in serum-poor media for four to five days as described above, were transferred to 4° C. and incubated for 90 minutes with either MuSK-Fc or TrkB-Fc (at 5 mg/ml), each in the presence of the indicated mock or agrin-containing conditioned media (with 100 nM agrin). Agrin levels were determined by Western analysis of the conditioned media with a rat agrin antibody (131, from StressGen, Inc.), using a purified agrin control of known concentration. Following these incubations, the cells were washed four times with PBS containing calcium and magnesium, and then incubated for an additional hour with radio-iodinated goat anti-human IgG (NEN/Dupont; 1 mCi/ml in PBS) to detect surface-bound receptor-Fc. After four additional washes, cells were solubilized in 0.1N NaOH, and bound radioactivity was determined. The assay is similar to that described elsewhere (Davis, S., et al., 1994, Science 266: 816–819).

Transient transfections using either previously described agrin constructs (Ferns, M., et al., 1993, Neuron 11: 491–502) or empty vector controls, or stable transfections of a chick MuSK-expression construct, were performed as described (Glass, D., et al., 1991, Cell 66: 405–413; Ip, N. Y., et al., 1992, PNAS (USA) 89: 3060–3064). Agrin concentrations in conditioned media derived from transient transfections were estimated by immunoblot comparisons with purified agrin of known concentration.

Figure 9A:
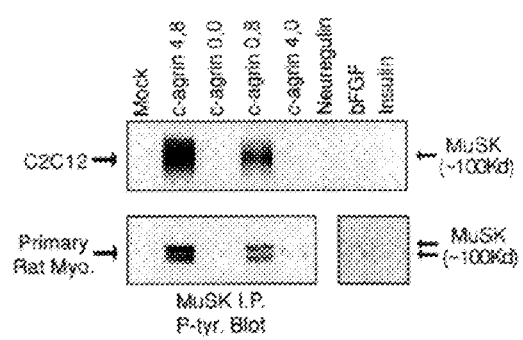
FIGS. 9A–9D c-agrin$_{4,8}$ and c-agrin$_{0,8}$ specifically induce rapid tyrosine phosphorylation of MuSK receptors. C2C12 and primary rat myoblasts were differentiated into myotubes and stimulated with conditioned media from COS cells transfected with a plasmid control (Mock) or plasmids encoding the various forms of soluble agrin, with conditioned media containing neuregulin, or with purified bFGF or insulin, as labelled. Stimulations were for ten minutes using 10 nM concentrations of the various factors, except as indicated in FIGS. 9C and 9D. Following factor challenges, the cells were lysed and subjected to immunoprecipitations (I.P.) for either the MuSK or ErbB3 receptors as indicated, then immunoblotted for phosphotyrosine levels. Only agrins containing the eight amino acid insert at the Z position, but not other factors, could induce MuSK phosphorylation (FIG. 9A). Agrin could not induce phosphorylation of another muscle receptor, ErbB3 (FIG. 9B). MuSK phosphorylation occurred at low agrin concentrations (FIG. 9C) and very rapidly in response to agrin (FIG. 9D).

Phosphorylation was assessed on the endogenous MuSK receptor that is highly expressed in myotube cultures, obtained by differentiating either the C2C12 mouse myoblast cell line (Valenzuela, D., et al., 1995, Neuron 15: 573–584) or primary rat myoblasts. Strikingly, soluble agrins containing the eight amino acid insert at position Z (c-agrin$_{4,8}$ and c-agrin$_{0,8}$), which are the forms capable of inducing AChR clustering, were also the forms that induced prominent tyrosine phosphorylation of MuSK (FIG. 9A). The agrin most active in clustering (c-agrin$_{4,8}$) was also most active in inducing MuSK phosphorylation (FIG. 9A). In contrast, the soluble agrins lacking the eight amino acid insert (c-agrin$_{4,0}$ and c-agrin$_{0,0}$), which cannot induce AChR clustering, also could not induce MuSK phosphorylation (FIG. 9A).

Figure 9B:

The specificity of action of agrin was further explored by comparing its activity to growth factors known to have receptors on muscle. Of the several such factors tested, including insulin, fibroblast growth factor (FGF) and ARIA/ neuregulin, only agrin could induce phosphorylation of MuSK (FIG. 9A); since FGF also induces AChR clustering on myotubes (Peng, H. B., et al., 1991, Neuron 6: 237–246), these results also indicate that MuSK phosphorylation is specific to agrin responses and not just to agents capable of inducing clustering. Furthermore, while such factors could be shown to induce phosphorylation of their own RTKs on myotubes (e.g., neuregulin induces phosphorylation of its cognate RTK, erbB3), agrin could only activate MuSK and not other RTKs (FIG. 9B).

Figure 9C:
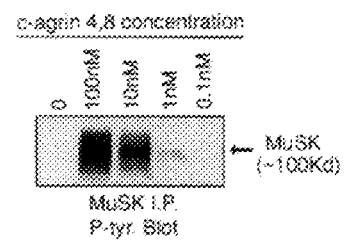
Figure 9D:
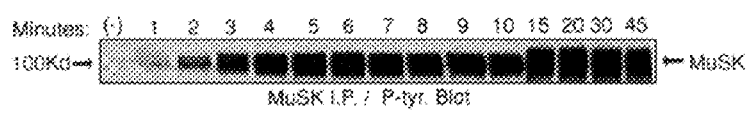

The activation of a RTK by its cognate ligand typically tends to occur rapidly, and applicants could demonstrate that agrin induces tyrosine phosphorylation of MuSK with kinetics similar to those seen for well-characterized RTK/ligand systems (e.g. Kaplan, D. R., et al., 1991, Nature 350: 158–160); induction was detectable by one minute, peaked within the first five minutes, and remained elevated for over an hour (FIG. 9D). The tyrosine phosphorylation of MuSK also occurred using agrin at concentrations similar to those noted for other ligands that act on RTKs (Ip, N. Y., et al., 1993, Neuron 10: 137–149), with phosphorylation detectable using 1 nM agrin (FIG. 9C).

The requirement of MuSK for agrin responsiveness, the ability of agrin to induce rapid and prominent MuSK phosphorylation, the specificity of agrin for MuSK as compared to other factors tested, and the precise correlation of agrin forms active in AChR clustering assays and in MuSK phosphorylation assays, together continue to support the notion that MuSK serves as the functional agrin receptor.

EXAMPLE 11

AGRIN DOES NOT DIRECTLY BIND TO AN ISOLATED MuSK ECTODOMAIN

If MuSK is indeed the functional agrin receptor, applicants would expect to be able to demonstrate binding of agrin to MuSK. In an attempt to demonstrate such binding, applicants first constructed an expression construct encoding a fusion protein between the ectodomain of rat MuSK and the Fc portion of human immunoglobulin G1 (designated MuSK-Fc), and then produced and purified the fusion protein. Similar receptor-Fc fusions have previously been used to characterize binding between RTKs and their ligands (Davis, S., et al., 1994, Science 266: 816–819; Stitt, T., et al., 1995, Cell 80: 661–670).

Baculovirus expression vectors encoding MuSK-Fc, TrkB-Fc, and Ret-Fc produced fusion proteins in which the ectodomains of rat TrkB, rat Ret, or rat MuSK, respectively, were linked to a spacer with the sequence Gly-Pro-Gly, followed by the hinge, CH2, and CH3 regions of human IgG1, beginning with the residues Glu-Pro-Lys, as described (Davis, S., et al., 1994, Science 266: 816–819). Baculovirus infections into *Spodoptera frugiperda* SF-21AE insect cells were performed by standard methods (Stitt, T., et al., 1995, Cell 80: 661–670). The soluble Fc-containing proteins were purified by protein A-Sepharose (Pharmacia) chromatography.

The binding of agrin to immobilized MuSK-Fc as compared to a monoclonal antibody specific for agrin was evaluated by use of BIAcore biosensor technology (Pharmacia Biosensor), using approaches previously described (Stitt, T., et al., 1995, Cell 80: 661–670). Heparin and CaCl2 were supplied by Sigma Chemical Co. (St. Louis, Mo.) and used without further purification. The agrin-specific monoclonal antibody (clone AGR131 generated to rat agrin) was purchased from StressGen Biotechnologies Corp. (Victoria, BC, Canada).

Figure 10A:
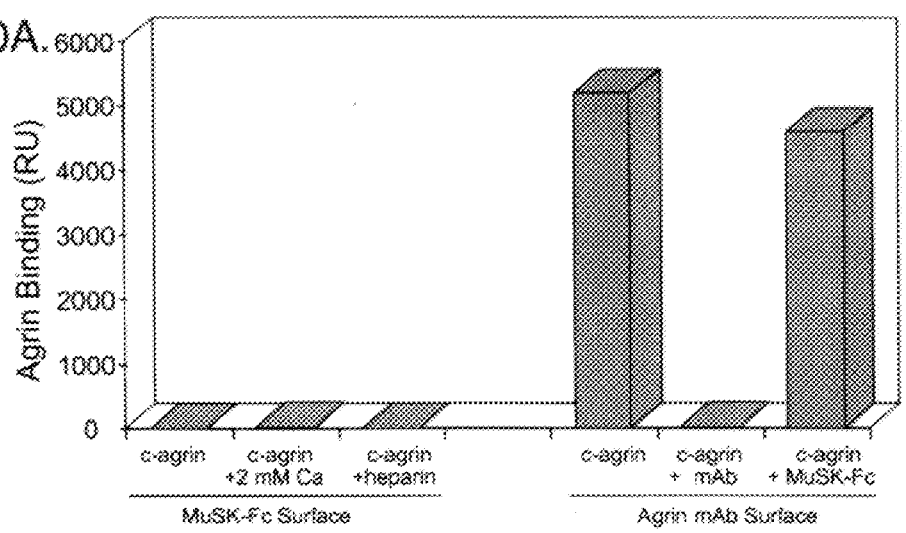
FIGS. 10A & 10B Agrin can not detectably bind to the isolated ectodomain of MuSK. Agrin was assayed for its binding to immobilized MuSK-Fc or to an immoblized agrin-specific monoclonal antibody (mAb), each coupled to a BIAcore sensorchip surface (FIG. 10A); bindings to the MuSK-Fc surface were also done in the presence 2 mM Ca$^{++}$ or heparin (0.01 mg/ml), as indicated, while bindings to the antibody surface were also competed with excess soluble monoclonal antibody or MuSK-Fc (each at 25 μg/ml), as indicated. Reciprocally, binding of soluble MuSK-Fc or monoclonal antibody to immobilized agrin was assayed by first binding conditioned media transfected with a plasmid control (Mock) or a plasmid encoding c-agrin4,8 (cAg$_{4,8}$) to nitrocellulose, followed by detection using either the soluble MuSK-Fc or the agrin-specific monoclonal antibody, as indicated (FIG. 10B); TrkB-Fc detection of nitrocellulose-immobilized BDNF served as an additional control.

In a first approach, applicants used MuSK-Fc together with BIAcore biosensor technology. The BIAcore technology allows for the direct and quantitative measure of binding of soluble ligands to receptors coupled onto a sensor chip. Recombinant MuSK-Fc was covalently coupled to a surface on the BIAcore sensor chip, and as a control, a monoclonal antibody specific for rat agrin was also coupled to a separate surface on the sensor chip; media containing c-agrin$_{4,8}$ was then passed over the two surfaces. While robust binding of the agrin to the antibody surface was easily detected, no binding of the agrin to the MuSK surface could be seen (FIG. 10A). Furthermore, while binding to the antibody surface was specifically competable by excess soluble antibody added to the agrin-containing media, the binding was not competable by excess soluble MuSK-Fc (FIG. 10A). Since agrin activity requires calcium (Bowe and Fallon, 1995, Ann. Rev. Neurosci. 18: 443–462), and because some heparin-binding factors require heparin to bind to their receptors (Goldfarb, M., 1990, Cell Growth & Differentiation 1: 439–445), applicants also attempted binding in the presence of calcium or heparin; in neither case was binding to the MuSK surface observed (FIG. 10A).

Figure 10B:
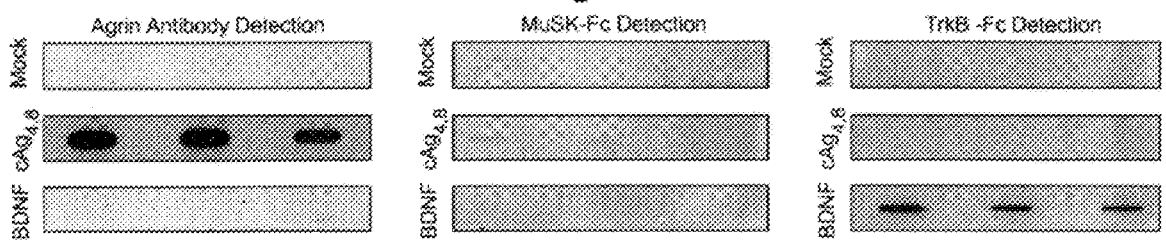

Next, applicants tried to demonstrate binding of MuSK and agrin by attempting to use MuSK-Fc to detect agrin immobilized onto nitrocellulose. In contrast to our control experiments, in which immobilized brain-derived neurotrophic factor (BDNF) was easily detected by an Fc fusion of its cognate receptor (TrkB-Fc), and in which immobilized agrin was easily detected by the agrin-specific monoclonal antibody, immobilized agrin could not be detected by MuSK-Fc (FIG. 10B).

The negative binding results described above demonstrate that the isolated MuSK receptor is not sufficient to bind agrin. Thus, despite the plethora of functional data indicating that agrin acts via MuSK, MuSK may not directly serve as a receptor for agrin. Alternatively, MuSK may require additional components or modifications which are required for it to bind and respond to agrin.

EXAMPLE 12

AGRIN ACTIVATES MuSK IN A CELL-CONTEXT-DEPENDENT FASHION: REQUIREMENT FOR A MYOTUBE-SPECIFIC ACCESSORY COMPONENT

Based on the results described above, applicants considered the possibility that the agrin-MuSK interaction requires additional components. To further explore this possibility, applicants determined the cell-context dependency for agrin activation of MuSK, reasoning that if an accessory component was required, it might be specifically expressed only on cells normally responding to agrin. Thus applicants ectopically expressed full-length cDNAs encoding rat, human and chicken MuSK in fibroblasts, and assayed for whether these MuSK receptors could be inducibly phosphorylated by agrin. When expressed in fibroblasts, none of the three species of MuSK could be phosphorylated in response to agrin. While this supported the possibility that MuSK requires an accesssory myotube-specific component to respond to agrin, it was also possible that our cDNAs encoded MuSK variants that could not respond to agrin. This was a potentially worrisome possibility since there are multiple differently spliced versions of the MuSK transcript (Valenzuela, D., et al., 1995, Neuron 15: 573–584), applicants did not know which of the forms were normally agrin-responsive, and our cDNAs only accounted for a subset of the variant forms. Thus applicants decided to express our cDNAs in myoblasts to verify that they could mediate responses to agrin when expressed in the right context. For this purpose applicants chose to express the chicken MuSK in the mouse C2C12 myoblast cell line, since the chicken MuSK could easily be distinguished from the endogenous mouse MuSK based on size and by using particular antibodies. When expressed in undifferentiated myoblasts, the chicken MuSK did not undergo phosphorylation in response to any isoforms of agrin (FIG. 11, see lanes indicated "Undif", upper panel), just as it did not undergo phosphorylation in fibroblasts; undifferentiated C2C12 cells do not express appreciable amounts of endogenous MuSK (FIG. 11, lanes indicated "Undif", lower panel and also (Valenzuela, D., et al., 1995, Neuron 15: 573–584), so applicants could not compare activation of the endogenous mouse MuSK in myoblasts. Upon differentiation into myotubes, the introduced chicken MuSK was as effectively activated by agrin as was the endogenous mouse MuSK (FIG. 11, lanes indicated "Diff", upper panel); both introduced and endogenous MuSK had identical profiles of responsivity to the various forms of agrins, with activations mediated only by forms having the eight amino acid insert at the Z position. Thus our cDNAs encode MuSK proteins that are perfectly competent to undergo agrin-induced phosphorylation, but they can only be activated by agrin in the context of a differentiated myotube, consistent with the notion that agrin activation of MuSK requires a myotube-specific accessory component that is not expressed in fibroblasts or undifferentiated myoblasts.

EXAMPLE 13

A RECEPTOR COMPLEX CAN BE DEMONSTRATED BETWEEN AGRIN, MuSK AND A MYOTUBE-SPECIFIC ACCESSORY COMPONENT

Figure 12:
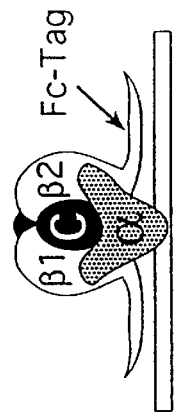
FIGS. 12A–12C. Relevant models for the agrin/MuSK receptor complex.
Figure 12:
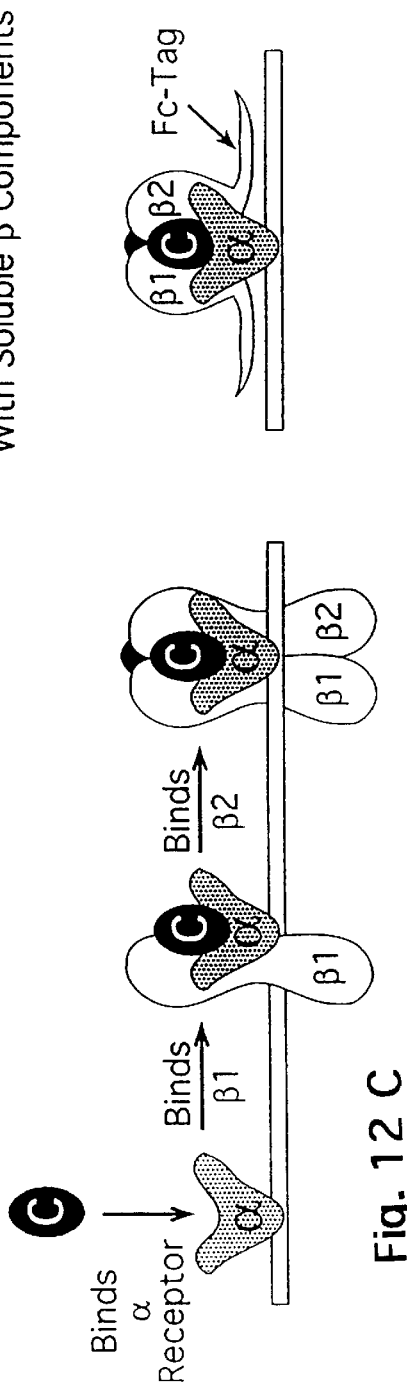
Figure 12:
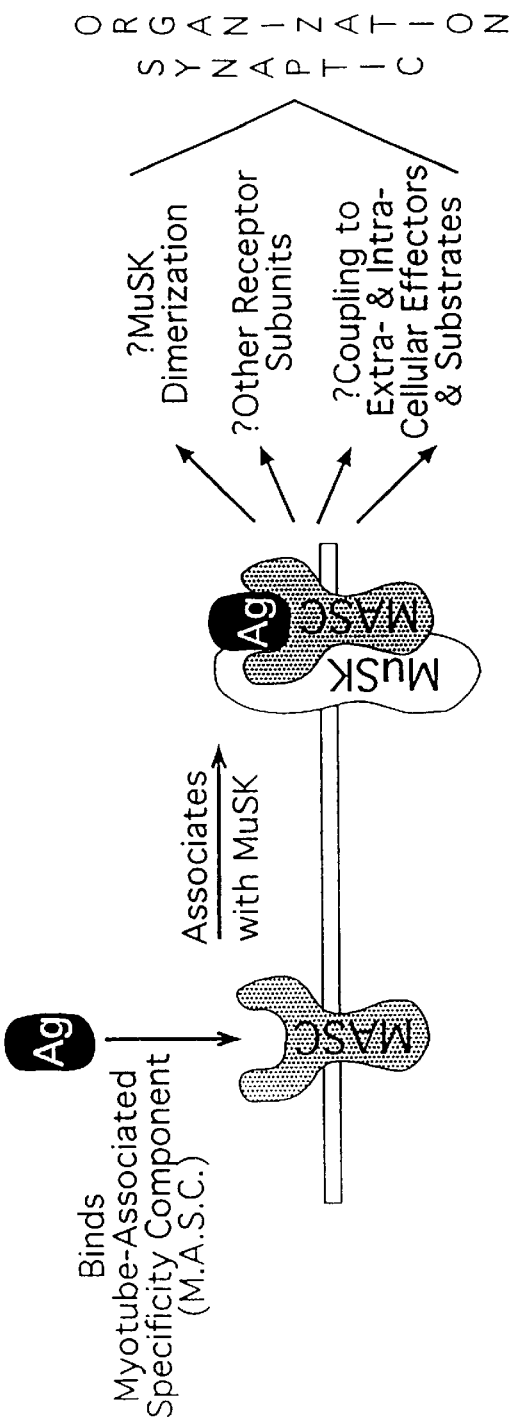

Altogether, the above data indicate that agrin requires MuSK to mediate clustering and that agrin activates MuSK very rapidly, but that agrin does not directly bind to a purified MuSK ectodomain and can only activate MuSK in the context of a myotube. These findings are consistent with the possibility that MuSK is a requisite part of an agrin receptor complex, but that although MuSK provides a key signaling function for this complex, it requires another component(s) to bind to agrin. Similar types of receptor complexes have been described for other ligands. Perhaps some of the best characterized examples include the receptor complexes for ciliary neurotrophic factor (CNTF) and its cytokine relatives (Davis, S., et al., 1993, Science 260: 1805–1808; Stahl and Yancopoulos, 1993, Cell 74: 587–590). In order to interact with its two signal transducing "b" receptor components, gp130 and LIFRb, CNTF must first bind to its "a" receptor component, known as CNTFRa. CNTFRa serves no signaling role, and is in fact linked to the surface via a glycosylphosphatidylinositol linkage and thus has no cytoplasmic domain. The receptor complex for CNTF is built in step-wise fashion: CNTF first binds to CNTFRa; this initial complex can then bind to and recruit a single "b" component; finally, a complete complex forms that involves "b" component dimerization, which is required for signal initiation (FIG. 12A). In the final complex, CNTF seems to make contacts with all three receptor components. Interestingly, receptor complexes for CNTF can be built in solution using just the soluble ectodomains of the various components. Furthermore, if just one of the receptor components is linked to the surface, a receptor complex can be built around it using soluble versions of the other components, but only in a CNTF-dependent fashion (FIG. 12B).

If agrin binds to MuSK in a receptor complex, applicants reasoned that they might be able to manipulate this complex in much the same way the CNTF receptor complex can be manipulated. To explore the possibility that myotubes specifically express an accessory component(s) required for agrin to bind MuSK (FIG. 12C), applicants decided to test whether applicants could specifically build a receptor complex on the surface of myotubes, but not on other cells, using agrin together with a soluble version of the MuSK receptor to complex to the putative accessory component(s) on the surface of myotubes. Confirming this possibility, applicants found that the binding of soluble MuSK-Fc to the surface of cells can be increased using agrin, but only on the surface of differentiated myotubes and not on the surface of fibroblasts or myoblasts (FIG. 13A). These data demonstrate that complexes can form between agrin and MuSK, but only in the presence of a myotube-specific component(s) (as suggested in FIG. 12C). Interestingly, although forms of c-agrin containing the eight amino acid insert at the Z position are best able to promote agrin-dependent MuSK complex formation, forms of c-agrin without this insert can also form these complexes. The ability of all the soluble forms to promote complex formation, including those lacking the eight amino acid insert for activity, may be related to previous findings that matrix-bound forms of agrins lacking the Z insert can activate clustering (Ferns, M., et al., 1992, Neuron 8: 1079–1086). Thus although soluble agrins lacking inserts at the Z position do not seem capable of signaling, they may be able to form partial complexes, while matrix-associated forms of these same agrins can proceed to form complete signaling-competent complexes. Interestingly, ligands for the EPH family of RTKs provide an example of ligands that bind but do not activate their receptors when presented in soluble form, but which can act as potent activators when bound to the cell surface (Davis, S., et al., 1994, Science 266: 816–819); deliberate clustering of the soluble ligands can allow them to activate as well, suggesting that the role of surface-attachment is to allow for ligand-clustering (Davis, S., et al., 1994, Science 266: 816–819).

In the absence of added agrin, the MuSK-Fc exhibited much higher binding to myotube surfaces than did several control receptor-Fc fusion proteins (FIG. 13A, data shown for TrkB-Fc); the MuSK-Fc, however, displayed similar agrin-independent binding to both myoblast and fibroblasts as did control receptor-Fc proteins (FIG. 13A). Specific binding of MuSK-Fc to myotube surfaces, in the absence of exogenously provided agrin, may indicate that MuSK has an affinity for its myotube-specific accessory component in the absence of ligand. Alternatively, since myotubes make muscle forms of agrin (lacking the eight amino acid insert at the Z position), the specific binding of MuSK-Fc to myotubes in the absence of added agrin could be explained by the formation of a complex between the added MuSK-Fc and endogenously expressed muscle agrin along with the accessory component; adding additional exogenous soluble agrin may simply allow for even more MuSK to be recruited into complexes with the myotube-specific accessory component. Although both myoblasts and myotubes make endogenous agrin, myoblasts seemingly cannot form complexes with added MuSK-Fc since they do not express the required accessory component.

To confirm that MuSK directly interacts with agrin as part of its receptor complex, applicants next demonstrated that radiolabelled agrin could be cross-linked to MuSK receptors on the surface of myotubes.

Flg-tagged human agrin protein corresponding to the COOH-terminal 50 kD of human agrin 4,8 was expressed in Cos cells and purified by affinity and size-exclusion chromatography to >95% purity. Twenty µg were iodinated by a modification of the lactoperoxidase method described previously (DiStefano, P., et al, 1992, Neuron 8: 983–993). Incorporation of 125I was greater than 80%; 125I-h-agrin 4,8-flg was separated from free 125I on a 1×3 cm Sephadex G-25 column prior to use in cross-linking assays. Specific activity was ~4000 cpm/fmol (~2400 Ci/mmol). Biological activity of 125I-h-agrin 4,8-flg was monitored by tyrosine phosphorylation of MuSK in C2C12 myotubes and was found to be indistinguishable from its unlabeled counterpart. For cross-linking studies, 10 cm plates of differentiated C2C12 myotubes were incubated in 1 nM of [125I]-agrin$_{4,8}$ in 1.5 ml of PBS containing 1% BSA and 1 mg/ml glucose in the presence or absence of 150-fold excess unlabeled agrin$_{4,8}$ for 75 min at 4° C. The cross-linking agent DSS (disuccinimidyl suberate) was added to a final concentration of 0.2 mM and the plates were incubated at room temperature for 30 min, washed 3 times with 50 mM Tris/150 mM NaCl pH 7.5, lysed, and subjected to immunoprecipitation with MuSK-specific antibodies. For peptide competition, peptide antigen was included in the immunoprecipitation at a final concentration of 20 µg/ml. The samples were then electrophoresed and the fixed and dried gels were exposed for autoradiography.

Immunoprecipitations using a MuSK-specific antibody, from lysates of myotubes chemically cross-linked to radiolabelled recombinant human agrin contained complexes corresponding in size to agrin/MuSK complexes (FIG. 13B). These agrin/MuSK complexes were not seen in the presence of excess unlabelled agrin, or if a peptide was used to block MuSK precipitation (FIG. 13B). Additional radiolabelled species that immunoprecipitated with the MuSK antibody correspond to forms of agrin that are associated with, but not cross-linked to, MuSK, presumably due to the low efficiency of cross-linking (FIG. 13B); low levels of additional agrin complexes, perhaps involving MASC, could also be detected in these immunoprecipitations.

Finally, if our findings that soluble MuSK could form complexes with its requisite myotube-specific accessory component are correct, then this soluble receptor should also act as an inhibitor of agrin-mediated responses by sequestering the accessory component and preventing it from interacting with the endogenously-expressed, signaling-competent MuSK. Indeed, addition of increasing amounts of MuSK-Fc did inhibit agrin-mediated clustering of AChRs (FIG. 13C) as well as agrin-induced MuSK phosphorylatio in a dose-dependent manner, while control receptor-Fc proteins had no inhibitory effect.

EXAMPLE 14

CLONING OF HUMAN AGRIN cDNA

Probes corresponding to human agrin were prepared by PCR based on partial sequences of human agrin available from the Genbank database. Two pairs of PCR primers were synthesized based on human agrin cDNA sequences obtained from Genbank. The sequences of the oligonucleotide primers were as follows:
Primer pair 18:
h-agrin 18-5': 5'-GACGACCTCTTCCGGAATTC-3' (SEQ. ID. NO. 17)
h-agrin 18-3': 5'-GTGCACATCCACAATGGC-3' (SEQ. ID. NO. 20)
Primer pair 35:
h-agrin 35-5': 5'-GAGCAGAGGGAAGGTTCCCTG-3' (SEQ. ID. NO. 19)
h-agrin 35-3': 5'-TCATTGTCCCAGCTGCGTGG-3' (SEQ. ID. NO. 20)

The oligonucleotide primers were used for PCR amplification of two segments of DNA of approximately 100 nts (primer pair 18) and 85 nts (primer pair 35) using 300 ngs of human genomic DNA as a template. The PCR amplification was carried out as recommended by the manufacturer (Perkin-Elmer) under the following conditions: 35 cycles at 94° C. for 60 sec, 55° C. for 50 sec and 72° C. for 30 sec. The PCR fragments obtained were purified from an agarose gel and re-amplified for 30 cycles using the same PCR conditions described above.

After amplification, the PCR reactions were electrophoresed in agarose gels, the agarose containing the DNA bands of 100 and 85 nts respectively was excised, purified by QiaEx II (Qiagen), and then cloned into plasmid pCR-script using Stratagene's pCR-Script cloning kit, followed by bacterial transformation and plating onto agar-ampicillin plates as recommended by the manufacturer. Bacterial colonies containing the 100 and 85 nt inserts were identified by PCR using the primers described above. The PCR fragments obtained were radiolabeled for use as probes using a standard PCR reaction (Perkin-Elmer) on 20 ng of DNA template, except that 5 nmoles each of dATP, dGTP and dTTP and 0.2 mCurie of alpha $^{32}$P-dCTP (Du Pont 3000 Ci/mmol) were added to the reaction mixture and then subjected to 7 cycles of PCR. Unincorporated label was separated from the probes on a G50 NICK column (Pharmacia). These probes were used to screen a human fetal brain cDNA library (Stratagene Cat# 936206) using standard library screening procedures (Sambrook, Fritsch and Maniatis, Molecular Cloning, a Laboratory Manual, (1989) Second Edition, Cold Spring Harbor Laboratory Press). One and a half million phage plaques were plated in XL-1 Blue bacteria as recommended by Stratagene, and transferred to nitrocellulose filters in duplicate as previously described (Id.). The filters were processed and each filter replica was used for hybridization with one of the above probes as previously described (Id.). Plaques hybridizing to both probes were isolated and purified and a plasmid containing the cDNA insert was excised from the lambda clone according to Stratagene's recommended procedure (EXASSIST/SOLR System). The pBluescript plasmid containing the human Agrin insert was purified and the insert was then sequenced using an automated sequencing kit (Applied Biosystems).

As a result of this screen, one clone (pBL-hAgrin1) was obtained which contains a nucleotide sequence encoding an amino acid sequence of human agrin. The first amino acid encoded by the cloned nucleotide sequence corresponds approximately to amino acid 424 of rat agrin (See FIGS. 14A–14C). The nucleotide sequence of the clone ends downstream of the stop codon. Clone pBL-hAgrin1 contains a 4 amino acid insert starting at the position which corresponds to position 1643 of FIGS. 14A–14C (SEQ. ID. NO. 30), a point which was previously described for the rat as position "Y" (Stone, D. M. and Nikolics, K., J. Neurosci. 15: 6767–6778 (1995)). The sequence of the 4 amino acid insert both in clone pBL-hAgrin1and in the rat is KSRK (SEQ. ID. NO. 21).

A second clone was obtained from this screen. This second clone (pBL-hAgrin23) also contains a nucleotide sequence encoding an amino acid sequence of human agrin. The first amino acid encoded by the cloned nucleotide sequence corresponds approximately to amino acid 1552 of the rat agrin (See FIGS. 14A–14C (SEQ. ID. NO. 30)). The nucleotide sequence of the clone ends downstream of the stop codon. Clone pBL-hAgrin23 contains an 8 amino acid insert starting at a position which corresponds to position 1780 of FIGS. 14A–14C (SEQ. ID. NO. 30) a point which was previously described for the rat as position "Z" (Stone, D. M. and Nikolics, K., J. Neurosci. 15: 6767–6778 (1995)). The sequence of the eight amino acid insert both in clone pBL-hAgrin23 and in the rat is ELANEIPV (SEQ. ID. NO. 22). As previously discussed, it has been reported that the 8 amino acid insert plays an important role in regulating the AChR clustering activity of different agrin forms. Therefore, by inserting a nucleotide sequence encoding the eight amino acid sequence ELANEIPV (SEQ. ID. NO. 22) into clone pBL-hAgrin1 at the position corresponding to position Z of rat agrin, a human 4-8 agrin clone may be obtained. The addition of the 8 amino acid insert at position Z should confer a high level of biological activity to the human 4-8 clone.

Clone pBL-hAgrin23 also contains the 4 amino acid "Y" insert as described above for clone pBL-hAgrin1. However, clone pBL-hAgrin23 contains 17 extra amino acids at the same "Y" position, such that the sequence of the "Y" insert in clone pBL-hAgrin23 is KSRKVLSASHPLTVSGASTPR (SEQ. ID. NO. 23). Therefore, in addition to the (4-0) and (4-8) human agrin splice variants described above, human clones corresponding to splice variants containing (Y–Z) inserts of (17-0), (17-8), (21-0), and (21-8) are indicated by these results and are within the scope of the present invention.

EXAMPLE 15

EXPRESSION OF HUMAN AGRIN

Construction of human agrin expression vector

A human agrin Sfi I-Aat II fragment containing the 4 amino acid insert at the position corresponding to the Y-site described for rat agrin (see FIGS. 14A–14C (SEQ. ID. NO. 30)) was excised from clone pBL h agrin-1. A human agrin Aat II-Not I fragment containing the 8 amino acid insert at the position corresponding to the Z-site described for rat agrin (see FIGS. 14A–14C (SEQ. ID. No. 30)) was excised from clone pBL h agrin-23. A Xho I-Sfi I fragment was then generated via PCR that contained a preprotrypsin signal peptide, the 8 amino acid flg peptide (from the flag tagging system, IBI/Kodak, Rochester, N.Y.) and the human agrin sequence corresponding to the sequence of amino acids from position 1480 to the Sfi I site located at amino acids 1563–1566 of rat agrin (see FIGS. 14A–14C). The three fragments were then ligated into a Xho I-Not I digested pMT21 expression vector to form the human agrin 4-8 expression vector pMT21-agrin 4-8. The sequence of human agrin 4-8 that was encoded in the expression vector is shown in FIGS. 15A–15B (SEQ. ID. NOS. 31, and 32). Expression vectors for the human clones corresponding to splice variants containing (Y–Z) inserts of (0-8) and (4-0) were also constructed.

Expression of human agrin (4-8) in E. coli

The gene for human agrin 4-8 was PCR amplified from pMT21-agrin 4-8 with the primer pair AG5' (5'-GAGAGAG GTTTAAACATGAGCCCCTGCCAGCCCAACCCCTG-3' (SEQ. ID. NO. 24)) and AG3' (5'-CTCTGCGGCCGC TTATCATGGGGTGGGGCAGGGCCGCAG-3' (SEQ. ID. NO. 25)). The PCR product was digested with the restriction enzymes Pme I and Not I and cloned into the Pme I and Not I sites of the vector pRG501, a pMB1 replicon that confers kanamycin resistance and is designed to express cloned genes from the phage T7 promoter. One isolate was characterized and named pRG531. The 1315 base pair Nco I-Nae I fragment internal to agrin in pRG531 was then replaced with the corresponding fragment from pMT21-agrin 4-8. The resulting plasmid, pRG451, was transformed into the expression strain RFJ209 [IN(rrnD-rrn/E)1 lacI$^Q$ lacZpL8 fhuAD322-405 rpoS$_{(MC4100)}$ ara::(lacUV5-T7 gene 1)8]. Cultures of RFJ209/pRG541 induced with IPTG express human agrin to about 5% of total cellular protein and fractionates with soluble protein upon cell disruption. The crude soluble protein fraction containing human agrin 4-8, as well as human agrin 4-8 purified by Q-Sepharose chromatography was determined to be active in phosphorylation of MuSK receptor.

Expression of human agrin (4-8) in Pichia pastoris

The 50 kD active fragment of human agrin 4-8 was cloned by PCR using a primer containing a portion of the S. cerevisiae α mating factor pre-pro secretion signal and the 5' end of the region encoding the 50 kD agrin fragment (GTATCTCTCGAGAAAAGAGAGGCTGAAGCT AGCCCCTGCCAGCCCAACC) (SEQ. ID. NO. 26), and a primer containing sequences from the region 3' of the agrin coding region and a NotI site (AATAGTGCG GCCGCCAACACTCAGGCAAGAAAATCATATC) (SEQ. ID. NO. 27). After PCR the fragment was digested with XhoI, which recognizes sequences in the 5' primer, and NotI, and was cloned into pPIC9 (Invitrogen) digested with XhoI and NotI. The resulting clone was digested with NotI and partially digested with NcoI to remove most of the PCRed agrin sequences. This region was replaced by a NotI-NcoI fragment of agrin from pRG541. PCRed regions were sequenced and shown to be wild-type. This clone, pRG543 was digested with SalI and transformed into Pichia pastoris by electroporation. Transformants were selected for a His+ Mut+ phenotype. Induction of the AOX1 promoter driving the expression of hAgrin was done by growing the cells in buffered glycerol-complex medium containing 0.5% glycerol, pH=6.0, for 24 hrs until the glycerol was exhausted, at which point methanol was added to a final concentration of 0.5%. The culture was centrifuged and the supernatant was dialyzed against PBS. The concentration of hAgrin was approximately 10 ug/ml and was determined to be active in phosphorylation of MuSK receptor.

Production of Human Agrin 4,8 from Baculovirus Infected Insect Cells

Virus Production

The flg-tagged gene for human agrin 4-8 was engineered into a baculovirus expression plasmid and recombined with viral DNA to generate recombinant baculovirus, amplified and harvested using methods previously described (O'Reilly, D. R., L. K. Miller, and V. A. Luckow, Baculovirus Expression Vectors- A Laboratory Manual 1992, New York: W. H. Freeman). SF21 insect cells (Spodoptera frugiperda) obtained from Invitrogen were adapted and expanded at 27° C. in Gibco SF900 II serum-free medium. Uninfected cells were grown to a density of 1×10$^6$ cells/mL. Cell density was determined by counting viable cells using a hemacytometer. The virus stock for FLAG-agrin was added to the bioreactor at a low multiplicity 0.01–0.1 PFU/cell to begin the infection. The infection process was allowed to continue for 3–4 days allowing maximum virus replication without incurring substantial cell lysis. The cell suspension was aseptically aliquoted into sterile centrifuge bottles and the cells removed by centrifugation (1600 RPM, 30 min). The cell-free supernatant was collected in sterile bottles and stored at 4° C. in the absence of light until further use.

The virus titer was determined by plaque assay as described by O'Reilly, Miller and Luckow. The method is carried out in 60 mm tissue-culture dishes which are seeded with 1.5×10⁶ cells. Serial dilutions of the virus stock are added to the attached cells and the mixture incubated with rocking to allow the virus to adsorb to individual cells. An agar overlay is added and plates incubated for 5 days at 27° C. Viable cells were stained with neutral red revealing circular plaques which were counted to give the virus titer expressed in plaque forming unit per milliliter (PFU/mL).

Infection of Cells for Protein Production

Uninfected SF21 cells were grown in a 60L ABEC bioreactor containing 40L of Gibco SF900 II medium with gentamicin sulfate (25 mg/L) and amphotericin B (1 mg/L). Temperature was controlled at 27° C. and the dissolved oxygen level was maintained at 50% of saturation by controlling the flowrate of oxygen in the inlet gas stream. When a density of 2×10⁶ cells/mL was reached, the cells were concentrated within the bioreactor to 20L, using a low shear steam sterilizable pump and a tangential flow filtration device with Millipore Prostak 0.45 micron membranes. After concentration, fresh sterile growth medium was slowly added to the bioreactor while the filtration system continued to remove the spent growth medium by diafiltration. After two volume exchanges an additional 20L of fresh medium was added to the bioreactor to resuspend the cells to the original volume of 40L.

The amount of virus stock required was calculated based on the cell density, virus titer and the desired multiplicity of infection (MOI). Multiplicity ratios between 1 and 10 pfu/cell have been effectively used. The virus stock was added aseptically to the bioreactor and the infection was allowed to proceed for three to four days.

Recovery and Chromatographic Purification

At the conclusion of the infection phase of the bioreactor process the cells were concentrated in the bioreactor using a 30 ft² Millipore Prostak filter (0.45 micron) pore size. The cell-free permeate passing through the filter was collected in a clean process vessel. The protein was diafiltered into a low conductivity buffer (20 mM citrate, pH 5.5) using Millipore Pellicon ultrafiltration membrane cassettes totaling 20 ft² with a nominal 10 kiloDalton cutoff. The protein in the retentate was loaded onto a cation exchange column (Pharmacia SP Sepharose FF) equilibrated with 20 mM citrate buffer, pH 5.5. After loading the protein was washed first with 20 mM citrate, 200 mM sodium chloride, pH 5.5 then with 20 mM Bicine, pH 8.0 to remove contaminating proteins. The protein was eluted with a 0–750 mM sodium chloride linear gradient over 7.5 column volumes. The eluted agrin was buffer exchanged into 20 mM Tris, pH 8.5 buffer to remove salt for subsequent binding to an anion exchange column.

The agrin was then bound to a Pharmacia Q Sepharose FF column equilibrated with 20 mM Tris, pH 8.5. After loading the column was washed with the same buffer to remove contaminating proteins and the protein eluted with a 0–250 mM sodium chloride gradient. The fractions containing agrin were pooled and concentrated and dialyzed into PBS containing calcium and magnesium.

Expression of human agrin (4-8) in COS-7 cells

Lipofectamine reagent (GIBCO-BRL, Inc.) and recommended protocols were used to transfect COS-7 cells with the human agrin cDNA clone pMT21-agrin 4-8 containing a nucleotide sequence encoding the eight amino acid sequence ELANEIPV at the position corresponding to position Z of rat agrin. COS media containing secreted ligand was harvested after three days and concentrated 20-fold by diafiltration (DIAFLO ultrafiltration membranes, Amicon, Inc.). The quantity of active human agrin present in the media was determined and expressed as the amount (in resonance units, R.U.) of MuSK receptor specific binding activity measured by a BIAcore binding assay.

DEPOSIT OF MICROORGANISMS

A clone designated pBluescript SK-containing dmk was deposited with the American Type Culture Collection, 12301 Parklawn Drive, Rockville, Md. 20852 on Jul. 13, 1993 under ATCC Accession No. 75498. Recombinant *Autographa californica* baculovirus encoding the rat Dmk RB (i.e., rat MuSK-IgG1 receptorbody) was designated "vDmk receptorbody" and deposited with the American Type Culture Collection, 12301 Parklawn Drive, Rockville, Md. 20852 on May 16, 1995 under ATCC Accession No. VR-2507. The cDNA clone pBL-hAgrin1 was deposited with the American Type Culture Collection, 12301 Parklawn Drive, Rockville, Md. 20852 on Dec. 12, 1995 under ATCC Accession No. 97378.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. An isolated nucleic acid molecule comprising a nucleotide sequence encoding a polypeptide having the MuSK-activating activity of human agrin, wherein the nucleotide sequence is selected from the group consisting of:
   (a) the nucleotide sequence encoding the polypeptide having the MuSK-activating activity of human agrin contained in the vector designated as pBL-hAgrin 1 (ATCC Accession No. 97378); and
   (b) a nucleotide sequence that, as a result of the degeneracy of the genetic code, differs from the nucleotide sequence of (a) and which encodes a polypeptide having the MuSK-activating activity of human agrin.

2. An isolated nucleic acid molecule comprising a nucleotide sequence encoding a polypeptide having the MuSK-activating activity of human agrin, wherein the nucleotide sequence is selected from the group consisting of:
   (a) the nucleotide sequence encoding the polypeptide having the MuSK-activating activity of human agrin as set forth in FIGS. 15A–15B (SEQ. ID. NO. 31); and
   (b) a nucleotide sequence that, as a result of the degeneracy of the genetic code, differs from the nucleotide sequence of (a) and which encodes a polypeptide having the MuSK-activating activity of human agrin.

3. An isolated nucleic acid molecule of claim 2, wherein the nucleotide sequence of (a) is lacking the nucleotides encoding the amino acid sequence KSRK at position Y as set forth in FIGS. 15A–15B.

4. An isolated nucleic acid molecule of claim 2, wherein the nucleotide sequence of (a) is lacking the nucleotides encoding the amino acid sequence ELANEIPV at position Z as set forth in FIGS. 15A–15B.

5. An isolated polypeptide encoded by the nucleic acid molecule of claim 1.

6. An isolated polypeptide encoded by the nucleic acid molecule of claim 2.

7. An isolated polypeptide encoded by the nucleic acid molecule of claim 3.

8. An isolated polypeptide encoded by the nucleic acid molecule of claim 4.

9. A vector which comprises the isolated nucleic acid molecule of claim 1, 2, 3 or 4.

10. An expression vector comprising a nucleic acid molecule of claim 1, 2, 3 or 4 wherein the nucleic acid molecule is operatively linked to an expression control sequence.

11. A host-vector system for the production of a polypeptide having the MuSK-activating activity of human agrin which comprises the vector of claim 10, in a suitable host cell.

12. The host-vector system of claim 11, wherein the suitable host cell is a bacterial cell.

13. The host-vector system of claim 12, wherein the bacterial cell is *E. coli*.

14. The host-vector system of claim 11, wherein the suitable host cell is a yeast cell.

15. The host-vector system of claim 14, wherein the yeast cell is *Pichia pastoris*.

16. The host-vector system of claim 11, wherein the suitable host cell is an insect cell.

17. The host-vector system of claim 16, wherein the insect cell is *Spodoptera frugiperda*.

18. The host-vector system of claim 11, wherein the suitable host cell is a mammalian cell.

19. The host-vector system of claim 18, wherein the mammalian cell is a COS cell.

20. The host-vector system of claim 18, wherein the mammalian cell is a CHO cell.

21. A method of producing a polypeptide having the MuSK-activating activity of human agrin which comprises growing cells of the host-vector system of claim 11, under conditions permitting production of the polypeptide and recovering the polypeptide so produced.

* * * * *

SEQUENCE LISTING ( 1 ) GENERAL INFORMATION:

( i i i ) NUMBER OF SEQUENCES: 32

( 2 ) INFORMATION FOR SEQ ID NO:1:

( i ) SEQUENCE CHARACTERISTICS:
        ( A ) LENGTH: 868 amino acids
        ( B ) TYPE: amino acid
        ( C ) STRANDEDNESS:
        ( D ) TOPOLOGY: unknown ( i i ) MOLECULE TYPE: protein ( x i ) SEQUENCE DESCRIPTION: SEQ ID NO:1:

```
Met  Arg  Glu  Leu  Val  Asn  Ile  Pro  Leu  Leu  Gln  Met  Leu  Thr  Leu  Val
  1             5                        10                        15
```

```
Ala Phe Ser Gly Thr Glu Lys Leu Pro Lys Ala Pro Val Ile Thr Thr
             20                  25                  30

Pro Leu Glu Thr Val Asp Ala Leu Val Glu Val Ala Thr Phe Met
             35                  40                  45

Cys Ala Val Glu Ser Tyr Pro Gln Pro Glu Ile Ser Trp Thr Arg Asn
 50                      55                  60

Lys Ile Leu Ile Lys Leu Phe Asp Thr Arg Tyr Ser Ile Arg Glu Asn
 65                  70                  75                  80

Gly Gln Leu Leu Thr Ile Leu Ser Val Glu Asp Ser Asp Asp Gly Ile
                 85                  90                  95

Tyr Cys Cys Thr Ala Asn Asn Gly Val Gly Gly Ala Val Glu Ser Cys
             100                 105                 110

Gly Ala Leu Gln Val Lys Met Lys Pro Lys Ile Thr Arg Pro Pro Ile
             115                 120                 125

Asn Val Lys Ile Ile Glu Gly Leu Lys Ala Val Leu Pro Cys Thr Thr
 130                     135                 140

Met Gly Asn Pro Lys Pro Ser Val Ser Trp Ile Lys Gly Asp Ser Ala
 145                 150                 155                 160

Leu Arg Glu Asn Ser Arg Ile Ala Val Leu Glu Ser Gly Ser Leu Arg
                 165                 170                 175

Ile His Asn Val Gln Lys Glu Asp Ala Gly Gln Tyr Arg Cys Val Ala
             180                 185                 190

Lys Asn Ser Leu Gly Thr Ala Tyr Ser Lys Leu Val Lys Leu Glu Val
         195                 200                 205

Glu Val Phe Ala Arg Ile Leu Arg Ala Pro Glu Ser His Asn Val Thr
     210                 215                 220

Phe Gly Ser Phe Val Thr Leu Arg Cys Thr Ala Ile Gly Met Pro Val
 225                 230                 235                 240

Pro Thr Ile Ser Trp Ile Glu Asn Gly Asn Ala Val Ser Ser Gly Ser
             245                 250                 255

Ile Gln Glu Asn Val Lys Asp Arg Val Ile Asp Ser Arg Leu Gln Leu
         260                 265                 270

Phe Ile Thr Lys Pro Gly Leu Tyr Thr Cys Ile Ala Thr Asn Lys His
     275                 280                 285

Gly Glu Lys Phe Ser Thr Ala Lys Ala Ala Ala Thr Val Ser Ile Ala
 290                 295                 300

Glu Trp Ser Lys Ser Gln Lys Glu Ser Lys Gly Tyr Cys Ala Gln Tyr
 305                 310                 315                 320

Arg Gly Glu Val Cys Asp Ala Val Leu Val Lys Asp Ser Leu Val Phe
             325                 330                 335

Phe Asn Thr Ser Tyr Pro Asp Pro Glu Glu Ala Gln Glu Leu Leu Ile
             340                 345                 350

His Thr Ala Trp Asn Glu Leu Lys Ala Val Ser Pro Leu Cys Arg Pro
             355                 360                 365

Ala Ala Glu Ala Leu Leu Cys Asn His Leu Phe Gln Glu Cys Ser Pro
             370                 375                 380

Gly Val Leu Pro Thr Pro Met Pro Ile Cys Arg Glu Tyr Cys Leu Ala
 385                 390                 395                 400

Val Lys Glu Leu Phe Cys Ala Lys Glu Trp Leu Ala Met Glu Gly Lys
                 405                 410                 415

Thr His Arg Gly Leu Tyr Arg Ser Gly Met His Phe Leu Pro Val Pro
             420                 425                 430

Glu Cys Ser Lys Leu Pro Ser Met His Gln Asp Pro Thr Ala Cys Thr
```

|     |     |     | 435 |     |     |     | 440 |     |     |     | 445 |     |     |     |
|-----|-----|-----|-----|-----|-----|-----|-----|-----|-----|-----|-----|-----|-----|-----|
| Arg | Leu 450 | Pro | Tyr | Leu | Asp | Tyr 455 | Lys | Lys | Glu | Asn | Ile 460 | Thr | Thr | Phe | Pro |
| Ser 465 | Ile | Thr | Ser | Ser | Lys 470 | Pro | Ser | Val | Asp | Ile 475 | Pro | Asn | Leu | Pro | Ala 480 |
| Ser | Thr | Ser | Ser | Phe 485 | Ala | Val | Ser | Pro | Ala 490 | Tyr | Ser | Met | Thr | Val 495 | Ile |
| Ile | Ser | Ile | Met 500 | Ser | Cys | Phe | Ala | Val 505 | Phe | Ala | Leu | Leu | Thr 510 | Ile | Thr |
| Thr | Leu | Tyr 515 | Cys | Cys | Arg | Arg | Arg 520 | Arg | Glu | Trp | Lys | Asn 525 | Lys | Lys | Arg |
| Glu | Ser 530 | Ala | Ala | Val | Thr | Leu 535 | Thr | Thr | Leu | Pro | Ser 540 | Glu | Leu | Leu | Leu |
| Asp 545 | Arg | Leu | His | Pro | Asn 550 | Pro | Met | Tyr | Gln | Arg 555 | Met | Pro | Leu | Leu | Leu 560 |
| Asn | Pro | Lys | Leu | Leu 565 | Ser | Leu | Glu | Tyr | Pro 570 | Arg | Asn | Asn | Ile | Glu 575 | Tyr |
| Val | Arg | Asp | Ile 580 | Gly | Glu | Gly | Ala | Phe 585 | Gly | Arg | Val | Phe | Gln 590 | Ala | Arg |
| Ala | Pro | Gly 595 | Leu | Leu | Pro | Tyr | Glu 600 | Pro | Phe | Thr | Met | Val 605 | Ala | Val | Lys |
| Met | Leu 610 | Lys | Glu | Glu | Ala | Ser 615 | Ala | Asp | Met | Gln | Ala 620 | Asp | Phe | Gln | Arg |
| Glu 625 | Ala | Ala | Leu | Met | Ala 630 | Glu | Phe | Asp | Asn | Pro 635 | Asn | Ile | Val | Lys | Leu 640 |
| Leu | Gly | Val | Cys | Ala 645 | Val | Gly | Lys | Pro | Met 650 | Cys | Leu | Leu | Phe | Glu 655 | Tyr |
| Met | Ala | Tyr | Gly 660 | Asp | Leu | Asn | Glu | Phe 665 | Leu | Arg | Ser | Met | Ser 670 | Pro | His |
| Thr | Val | Cys 675 | Ser | Leu | Ser | His | Ser 680 | Asp | Leu | Ser | Thr | Arg 685 | Ala | Arg | Val |
| Ser | Ser 690 | Pro | Gly | Pro | Pro | Pro 695 | Leu | Ser | Cys | Ala | Glu 700 | Gln | Leu | Cys | Ile |
| Ala 705 | Arg | Gln | Val | Ala | Ala 710 | Gly | Met | Ala | Tyr | Leu 715 | Ser | Glu | Arg | Lys | Phe 720 |
| Val | His | Arg | Asp | Leu 725 | Ala | Thr | Arg | Asn | Cys 730 | Leu | Val | Gly | Glu | Asn 735 | Met |
| Val | Val | Lys | Ile 740 | Ala | Asp | Phe | Gly | Leu 745 | Ser | Arg | Asn | Ile | Tyr 750 | Ser | Ala |
| Asp | Tyr | Tyr 755 | Lys | Ala | Asp | Gly | Asn 760 | Asp | Ala | Ile | Pro | Ile 765 | Arg | Trp | Met |
| Pro | Pro 770 | Glu | Ser | Ile | Phe | Tyr 775 | Asn | Arg | Tyr | Thr | Thr 780 | Glu | Ser | Asp | Val |
| Trp 785 | Ala | Tyr | Gly | Val | Val 790 | Leu | Trp | Glu | Ile | Phe 795 | Ser | Tyr | Gly | Leu | Gln 800 |
| Pro | Tyr | Tyr | Gly | Met 805 | Ala | His | Glu | Glu | Val 810 | Ile | Tyr | Tyr | Val | Arg 815 | Asp |
| Gly | Asn | Ile | Leu 820 | Ala | Cys | Pro | Glu | Asn 825 | Cys | Pro | Leu | Glu | Leu 830 | Tyr | Asn |
| Leu | Met | Arg 835 | Leu | Cys | Trp | Ser | Lys 840 | Leu | Pro | Ala | Asp | Arg 845 | Pro | Ser | Phe |
| Cys | Ser 850 | Ile | His | Arg | Ile | Leu 855 | Gln | Arg | Met | Cys | Glu 860 | Arg | Ala | Glu | Gly |

Thr Val Gly Val
865

( 2 ) INFORMATION FOR SEQ ID NO:2:

( i ) SEQUENCE CHARACTERISTICS:
        ( A ) LENGTH: 2869 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:2:

```
GAATTCGGCA CGAGCAAACA GTCATTAGTG GACGACTCTA TTGTAATAAA CTGTGCTTTA      60
AAATGTAAAC CAGGGAGCGT TTTTTTTCCT CACATTGTCC AGAAGCAACC TTTCTTCCTG     120
AGCCTGGATT AATCATGAGA GAGCTCGTCA ACATTCCACT GTTACAGATG CTCACCCTGG     180
TTGCCTTCAG CGGGACCGAG AAACTTCCAA AAGCCCCTGT CATCACCACG CCTCTTGAAA     240
CTGTAGATGC CTTAGTTGAA GAAGTGGCGA CTTTCATGTG CGCCGTGGAA TCCTACCCTC     300
AGCCTGAAAT TTCTTGGACC AGAAATAAAA TTCTCATCAA GCTGTTTGAC ACCCGCTACA     360
GCATCCGAGA GAACGGTCAG CTCCTCACCA TCCTGAGTGT GGAGGACAGT GATGATGGCA     420
TCTACTGCTG CACAGCCAAC AATGGAGTGG GAGGAGCGGT GGAAAGTTGT GGCGCCCTGC     480
AAGTGAAGAT GAAGCCTAAA ATAACTCGTC CTCCCATCAA TGTAAAAATA ATTGAGGGAT     540
TGAAAGCAGT CCTACCGTGC ACTACGATGG GTAACCCCAA GCCATCCGTG TCCTGGATTA     600
AGGGGGACAG TGCTCTCAGG GAAAATTCCA GGATTGCAGT TCTTGAATCT GGGAGTTTAA     660
GGATCCATAA TGTGCAAAAG GAAGACGCAG GACAGTACCG ATGTGTGGCA AAAAACAGCC     720
TGGGCACAGC TTACTCCAAA CTGGTGAAGC TGGAAGTGGA GGTTTTTGCA AGAATCCTGC     780
GTGCTCCTGA ATCCACAAT GTCACCTTTG GTTCCTTTGT AACCCTACGC TGCACAGCAA     840
TAGGCATGCC TGTCCCCACC ATCAGCTGGA TTGAAAACGG AAATGCTGTT TCTTCAGGTT     900
CCATTCAAGA GAATGTGAAA GACCGAGTGA TTGACTCAAG ACTCCAGCTC TTTATCACAA     960
AGCCAGGACT CTACACATGC ATAGCTACCA ATAAGCATGG AGAGAAATTC AGTACCGCAA    1020
AGGCTGCAGC CACTGTCAGT ATAGCAGAAT GGAGCAAATC ACAGAAAGAA AGCAAAGGCT    1080
ACTGTGCCCA GTACAGAGGG GAGGTGTGTG ATGCCGTCCT GGTGAAAGAC TCTCTTGTCT    1140
TCTTCAACAC CTCCTATCCC GACCCTGAGG AGGCCCAAGA GCTGCTGATC CACACTGCGT    1200
GGAATGAACT CAAGGCTGTG AGCCCACTCT GCCGACCAGC TGCCGAGGCT CTGCTGTGTA    1260
ATCACCTCTT CCAGGAGTGC AGCCCTGGAG TGCTACCTAC TCCTATGCCC ATTTGCAGAG    1320
AGTACTGCTT GGCAGTAAAG GAGCTCTTCT GTGCAAAGGA ATGGCTGGCA ATGGAAGGGA    1380
AGACCCACCG CGGACTCTAC AGATCCGGGA TGCATTTCCT CCCGGTCCCG GAGTGCAGCA    1440
AGCTTCCCAG CATGCACCAG GACCCCACAG CCTGCACAAG ACTGCCGTAT TTAGATTATA    1500
AAAAGAAAA CATAACAACA TTCCCGTCCA TAACGTCCTC CAAGCCGAGC GTGGACATTC    1560
CAAACCTGCC TGCCTCCACG TCTTCCTTCG CCGTCTCGCC TGCGTACTCC ATGACTGTCA    1620
TCATCTCCAT CATGTCCTGC TTTGCGGTGT TTGCTCTCCT CACCATCACT ACTCTCTATT    1680
GCTGCCGAAG GAGGAGAGAG TGGAAAAATA AGAAAAGAGA GTCGGCAGCG TGACCCTCA    1740
CCACATTGCC TTCCGAGCTC CTGCTGGACA GGCTGCATCC CAACCCCATG TACCAGAGGA    1800
TGCCACTCCT TCTGAATCCC AAGTTGCTCA GCCTGGAGTA TCCGAGGAAT AACATCGAGT    1860
ATGTCAGAGA CATCGGAGAG GGAGCGTTTG GAAGGGTCTT TCAAGCGAGG GCCCCAGGCT    1920
```

|            |            |            |            |            |            |      |
|------------|------------|------------|------------|------------|------------|------|
| TGCTTCCTTA | TGAACCCTTC | ACTATGGTGG | CTGTGAAGAT | GCTGAAGGAG | GAGGCCTCCG | 1980 |
| CAGATATGCA | GGCAGACTTT | CAGAGGGAGG | CAGCCCTCAT | GGCGGAGTTT | GACAACCCCA | 2040 |
| ACATTGTGAA | GCTCTTAGGT | GTGTGTGCTG | TTGGGAAGCC | AATGTGCCTG | CTCTTTGAAT | 2100 |
| ATATGGCCTA | TGGTGACCTC | AATGAGTTCC | TCCGAAGCAT | GTCCCCTCAC | ACTGTGTGCA | 2160 |
| GCCTCAGCCA | CAGTGACCTG | TCCACGAGGG | CTCGGGTGTC | CAGCCCTGGT | CCTCCACCCC | 2220 |
| TGTCTTGTGC | GGAACAGCTC | TGTATTGCCA | GGCAAGTGGC | AGCTGGCATG | GCCTACCTGT | 2280 |
| CGGAGCGCAA | GTTTGTCCAT | CGGGACTTAG | CTACCAGGAA | CTGCCTGGTT | GGAGAGAACA | 2340 |
| TGGTGGTGAA | AATTGCAGAC | TTTGGCCTCT | CTAGGAACAT | CTACTCCGCA | GACTACTACA | 2400 |
| AAGCTGATGG | AAACGATGCT | ATACCTATCC | GCTGGATGCC | ACCCGAGTCT | ATCTTCTACA | 2460 |
| ACCGCTACAC | CACGGAGTCA | GATGTGTGGG | CTTATGGCGT | GGTCCTCTGG | GAGATCTTCT | 2520 |
| CCTATGGACT | GCAGCCCTAC | TATGGAATGG | CCCATGAGGA | GGTCATTTAC | TATGTGAGAG | 2580 |
| ATGGTAACAT | CCTTGCCTGC | CCTGAGAACT | GTCCCTTGGA | ACTGTACAAC | CTTATGCGCC | 2640 |
| TATGTTGGAG | CAAGCTGCCT | GCAGACAGAC | CCAGCTTCTG | CAGTATCCAC | CGGATCCTGC | 2700 |
| AGCGCATGTG | CGAGAGAGCA | GAGGGAACGG | TAGGCGTCTA | AGGTTGACCA | TGCTCAAACA | 2760 |
| ACACCCAGGA | GGATCTTTTC | AGACTGCGAG | CTGGAGGGAT | CCTAAAGCAG | AGGGCGNATA | 2820 |
| AGNNCAGATA | GGAAGAGTTT | ATCTCAGGCA | GCACGTNCAG | TTGGTTGTT  |            | 2869 |

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

Asp Val Trp Ala Tyr Gly
1             5

( 2 ) INFORMATION FOR SEQ ID NO:4:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

GAATTCGAGC TCCCRWANGC CCANACRTC          29

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

Asp Leu Ala Thr Arg Asn
1             5

( 2 ) INFORMATION FOR SEQ ID NO:6:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

TCTTGACTCG AGAYYTNGCN ACNMGNAA                    28

( 2 ) INFORMATION FOR SEQ ID NO:7:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:7:

Asp Leu Ala Ala Arg Asn
 1              5

( 2 ) INFORMATION FOR SEQ ID NO:8:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

TCTTGACTCG AGAYYTNGCN GCNMGNAA                    28

( 2 ) INFORMATION FOR SEQ ID NO:9:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:9:

Asp Val Trp Ser Leu Gly
 1              5

( 2 ) INFORMATION FOR SEQ ID NO:10:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

GAATTCGAGC TCCCRTANSW CCANACRTC                    29

( 2 ) INFORMATION FOR SEQ ID NO:11:

( i ) SEQUENCE CHARACTERISTICS:

(A) LENGTH: 6 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:11:

Asp Val Trp Ser Phe Gly
1               5

(2) INFORMATION FOR SEQ ID NO:12:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:12:

GAATTCGAGC TCCCRAANSW CCANACRTC        29

(2) INFORMATION FOR SEQ ID NO:13:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:13:

Asp Val Trp Ser Tyr Gly
1               5

(2) INFORMATION FOR SEQ ID NO:14:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:14:

GAATTCGAGC TCCCNARNSW CCANACRTC        29

(2) INFORMATION FOR SEQ ID NO:15:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:15:

GAATTCGAGC TCCCRTANSW CCANACRTC        29

(2) INFORMATION FOR SEQ ID NO:16:

(i) SEQUENCE CHARACTERISTICS:
(A) LENGTH: 18 amino acids
(B) TYPE: amino acid
(C) STRANDEDNESS: single (D) TOPOLOGY: linear (ii) MOLECULE TYPE: protein (ix) FEATURE:
    (A) NAME/KEY: Other
    (B) LOCATION: 1...18
    (D) OTHER INFORMATION: Nomenclature for this antibody is 52307K.

(xi) SEQUENCE DESCRIPTION: SEQ ID NO:16:

Thr Leu Pro Ser Glu Leu Leu Leu Asp Arg Leu His Pro Asn Pro Met
1               5                   10                  15
Tyr Gln (2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: h-agrin 18-5'
        (B) LOCATION: 1...20
        (D) OTHER INFORMATION: Oligonucleotide primer (xi) SEQUENCE DESCRIPTION: SEQ ID NO:17:

GACGACCTCT TCCGGAATTC                                                  20

(2) INFORMATION FOR SEQ ID NO:18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: h-agrin 18-3'
        (B) LOCATION: 1...18
        (D) OTHER INFORMATION: Oligonucleotide primer (xi) SEQUENCE DESCRIPTION: SEQ ID NO:18:

GTGCACATCC ACAATGGC                                                    18

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: h-agrin 35-5'
        (B) LOCATION: 1...21
        (D) OTHER INFORMATION: Oligonucleotide primer (xi) SEQUENCE DESCRIPTION: SEQ ID NO:19:

GAGCAGAGGG AAGGTTCCCT G                                           21

(2) INFORMATION FOR SEQ ID NO:20:

( i ) SEQUENCE CHARACTERISTICS:
   ( A ) LENGTH: 20 base pairs
   ( B ) TYPE: nucleic acid
   ( C ) STRANDEDNESS: single
   ( D ) TOPOLOGY: linear ( i i ) MOLECULE TYPE: DNA ( i x ) FEATURE:
   ( A ) NAME/KEY: h-agrin 35-3'
   ( B ) LOCATION: 1...20
   ( D ) OTHER INFORMATION: Oligonucleotide primer ( x i ) SEQUENCE DESCRIPTION: SEQ ID NO:20:

TCATTGTCCC AGCTGCGTGG    20

( 2 ) INFORMATION FOR SEQ ID NO:21:

( i ) SEQUENCE CHARACTERISTICS:
      ( A ) LENGTH: 4 amino acids
      ( B ) TYPE: amino acid
      ( C ) STRANDEDNESS: single
      ( D ) TOPOLOGY: linear ( i i ) MOLECULE TYPE: protein ( i x ) FEATURE:
      ( A ) NAME/KEY: Other
      ( B ) LOCATION: 1...4
      ( D ) OTHER INFORMATION: Amino acid insert both in
            clone pBL- hAgrin1 and the rat.

( x i ) SEQUENCE DESCRIPTION: SEQ ID NO:21:

Lys Ser Arg Lys
 1

( 2 ) INFORMATION FOR SEQ ID NO:22:

( i ) SEQUENCE CHARACTERISTICS:
      ( A ) LENGTH: 8 amino acids
      ( B ) TYPE: amino acid
      ( C ) STRANDEDNESS: single
      ( D ) TOPOLOGY: linear ( i i ) MOLECULE TYPE: protein ( i x ) FEATURE:
      ( A ) NAME/KEY: Other
      ( B ) LOCATION: 1...8
      ( D ) OTHER INFORMATION: Amino acid insert in clone
            pBL-hAgrin 23 and in the rat.

( x i ) SEQUENCE DESCRIPTION: SEQ ID NO:22:

Glu Leu Ala Asn Glu Ile Pro Val
 1               5

( 2 ) INFORMATION FOR SEQ ID NO:23:

( i ) SEQUENCE CHARACTERISTICS:
      ( A ) LENGTH: 21 amino acids
      ( B ) TYPE: amino acid
      ( C ) STRANDEDNESS: single
      ( D ) TOPOLOGY: linear ( i i ) MOLECULE TYPE: protein ( i x ) FEATURE:
      ( A ) NAME/KEY: Other
      ( B ) LOCATION: 1...21
      ( D ) OTHER INFORMATION: "Y"insert in clone pBL-h
            Agrin23.

( x i ) SEQUENCE DESCRIPTION: SEQ ID NO:23:

| Lys | Ser | Arg | Lys | Val | Leu | Ser | Ala | Ser | His | Pro | Leu | Thr | Val | Ser | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ala | Ser | Thr | Pro | Arg |
|-----|-----|-----|-----|-----|
|     | 20  |     |     |     |

( 2 ) INFORMATION FOR SEQ ID NO:24:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: AG5'
        ( B ) LOCATION: 1...41
        ( D ) OTHER INFORMATION:

( x i ) SEQUENCE DESCRIPTION: SEQ ID NO:24:

```
GAGAGAGGTT   TAAACATGAG   CCCCTGCCAG   CCCAACCCCT  G                         41
```

( 2 ) INFORMATION FOR SEQ ID NO:25:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: AG3'
        ( B ) LOCATION: 1...39
        ( C ) OTHER INFORMATION:

( x i ) SEQUENCE DESCRIPTION: SEQ ID NO:25:

```
CTCTGCGGCC   GCTTATCATG   GGGTGGGGCA   GGGCCGCAG                             39
```

( 2 ) INFORMATION FOR SEQ ID NO:26:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: Primer
        ( B ) LOCATION: 1...49
        ( D ) OTHER INFORMATION:

( x i ) SEQUENCE DESCRIPTION: SEQ ID NO:26:

```
GTATCTCTCG   AGAAAAGAGA   GGCTGAAGCT   AGCCCCTGCC   AGCCCAACC              49
```

( 2 ) INFORMATION FOR SEQ ID NO:27:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: Primer
        ( B ) LOCATION: 1...40

( D ) OTHER INFORMATION:

( x i ) SEQUENCE DESCRIPTION: SEQ ID NO:27:

AATAGTGCGG CCGCCAACAC TCAGGCAAGA AAATCATATC                          40

( 2 ) INFORMATION FOR SEQ ID NO:28:

( i ) SEQUENCE CHARACTERISTICS:
        ( A ) LENGTH: 2610 base pairs
        ( B ) TYPE: nucleic acid
        ( C ) STRANDEDNESS: unknown
        ( D ) TOPOLOGY: unknown ( i i ) MOLECULE TYPE: DNA ( i x ) FEATURE:
        ( A ) NAME/KEY: Human MuSK
        ( B ) LOCATION: 1...2610
        ( C ) OTHER INFORMATION:

( x i ) SEQUENCE DESCRIPTION: SEQ ID NO:28:

ATGAGAGAGC TCGTCAACAT TCCACTGGTA CATATTCTTA CTCTGGTTGC CTTCAGCGGA    60
ACTGAGAAAC TTCCAAAAGC TCCTGTCATC ACCACTCCTC TTGAAACAGT GGATGCCTTA   120
GTTGAAGAAG TGGCTACTTT CATGTGTGCA GTGGAATCCT ACCCCCAGCC TGAGATTTCC   180
TGGACTAGAA ATAAAATTCT CATTAAACTC TTTGACACCC GGTACAGCAT CCGGGAGAAT   240
GGGCAGCTCC TCACCATCCT GAGTGTGGAA GACAGTGATG ATGGCATTTA CTGCTGCACG   300
GCCAACAATG TGTGGGAGG AGCTGTGGAG AGTTGTGGAG CCCTGCAAGT GAAGATGAAA    360
CCTAAAATAA CTCGCCCTCC CATAAATGTG AAAATAATAG AGGGATTAAA AGCAGTCCTA   420
CCATGTACTA CAATGGGTAA TCCCAAACCA TCAGTGTCTT GGATAAAGGG AGACAGCCCT   480
CTCAGGGAAA ATTCCCGAAT TGCAGTTCTT GAATCTGGGA GCTTGAGGAT TCATAACGTA   540
CAAAAGGAAG ATGCAGGACA GTATCGATGT GTGGCAAAAA ACAGCCTCGG ACAGCATAT    600
TCCAAAGTGG TGAAGCTGGA AGTTGAGGTT TTTGCCAGGA TCCTGCGGGC TCCTGAATCC   660
CACAATGTCA CCTTTGGCTC CTTTGTGACC CTGCACTGTA CAGCAACAGG CATTCCTGTC   720
CCCACCATCA CCTGGATTGA AAACGGAAAT GCTGTTTCTT CTGGGTCCAT TCAAGAGAGT   780
GTGAAAGACC GAGTGATTGA CTCAAGACTG CAGCTGTTTA TCACCAAGCC AGGACTCTAC   840
ACATGCATAG CTACCAATAA GCATGGGGAG AAGTTCAGTA CTGCCAAGGC TGCAGCCACC   900
ATCAGCATAG CAGAATGGAG TAAACCACAG AAAGATAACA AAGGCTACTG CGCCCAGTAC   960
AGAGGGGAGG TGTGTAATGC AGTCCTGGCA AAAGATGCTC TTGTTTTCT CAACACCTCC   1020
TATGCGGACC CTGAGGAGGC CCAAGAGCTA CTGGTCCACA CGGCCTGGAA TGAACTGAAA  1080
GTAGTGAGCC CAGTCTGCCG GCCAGCTGCT GAGGCTTTGT TGTGTAACCA CATCTTCCAG  1140
GAGTGCAGTC CTGGAGTAGT GCCTACTCCT ATTCCCATTT GCAGAGAGTA CTGCTTGGCA  1200
GTAAAGGAGC TCTTCTGCGC AAAAGAATGG CTGGTAATGG AAGAGAAGAC CCACAGAGGA  1260
CTCTACAGAT CCGAGATGCA TTTGCTGTCC GTGCCAGAAT GCAGCAAGCT TCCCAGCATG  1320
CATTGGGACC CCACGGCCTG TGCCAGACTG CCACATCTAG ATTATAACAA AGAAAACCTA  1380
AAAACATTCC CACCAATGAC GTCCTCAAAG CCAAGTGTGG ACATTCCAAA TCTGCCTTCC  1440
TCCTCCTCTT CTTCCTTCTC TGTCTCACCT ACATACTCCA TGACTGTAAT AATCTCCATC  1500
ATGTCCAGCT TTGCAATATT TGTGCTTCTT ACCATAACTA CTCTCTATTG CTGCCGAAGA  1560
AGAAAACAAT GGAAAAATAA GAAAAGAGAA TCAGCAGCAG TAACCCTCAC CACACTGCCT  1620
TCTGAGCTCT TACTAGATAG ACTTCATCCC AACCCCATGT ACCAGAGGAT GCCGCTCCTT  1680

-continued

```
CTGAACCCCA AATTGCTCAG CCTGGAGTAT CCAAGGAATA ACATTGAATA TGTGAGAGAC    1740
ATCGGAGAGG GAGCGTTTGG AAGGGTGTTT CAAGCAAGGG CACCAGGCTT ACTTCCCTAT    1800
GAACCTTTCA CTATGGTGGC AGTAAAGATG CTCAAAGAAG AAGCCTCGGC AGATATGCAA    1860
GCGGACTTTC AGAGGGAGGC AGCCCTCATG GCAGAATTTG ACAACCCTAA CATTGTGAAG    1920
CTATTAGGAG TGTGTGCTGT CGGGAAGCCA ATGTGCCTGC TCTTTGAATA CATGGCCTAT    1980
GGTGACCTCA ATGAGTTCCT CCGCAGCATG TCCCCTCACA CCGTGTGCAG CCTCAGTCAC    2040
AGTGACTTGT CTATGAGGGC TCAGGTCTCC AGCCCTGGGC CCCCACCCCT CTCCTGTGCT    2100
GAGCAGCTTT GCATTGCCAG GCAGGTGGCA GCTGGCATGG CTTACCTCTC AGAACGTAAG    2160
TTTGTTCACC GAGATTTAGC CACCAGGAAC TGCCTGGTGG GCGAGAACAT GGTGGTGAAA    2220
ATTGCCGACT TTGGCCTCTC CAGGAACATC TACTCAGCAG ACTACTACAA AGCTAATGAA    2280
AACGACGCTA TCCCTATCCG TTGGATGCCA CCAGAGTCCA TTTTTTATAA CCGCTACACT    2340
ACAGAGTCTG ATGTGTGGGC CTATGGCGTG GTCCTCTGGG AGATCTTCTC CTATGGCCTG    2400
CAGCCCTACT ATGGGATGGC CCATGAGGAG GTCATTTACT ACGTGCGAGA TGGCAACATC    2460
CTCTCCTGCC CTGAGAACTG CCCCGTGGAG CTGTACAATC TCATGCGTCT ATGTTGGAGC    2520
AAGCTGCCTG CAGACAGACC CAGTTTCACC AGTATTCACC GAATTCTGGA ACGCATGTGT    2580
GAGAGGGCAG AGGGAACTGT GAGTGTCTAA                                    2610
```

( 2 ) INFORMATION FOR SEQ ID NO:29:

( i ) SEQUENCE CHARACTERISTICS:
        ( A ) LENGTH: 869 amino acids
        ( B ) TYPE: amino acid
        ( C ) STRANDEDNESS:
        ( D ) TOPOLOGY: unknown ( i i ) MOLECULE TYPE: protein ( x i ) SEQUENCE DESCRIPTION: SEQ ID NO:29:

```
Met Arg Glu Leu Val Asn Ile Pro Leu Val His Ile Leu Thr Leu Val
 1               5                  10                  15

Ala Phe Ser Gly Thr Glu Lys Leu Pro Lys Ala Pro Val Ile Thr Thr
            20                  25                  30

Pro Leu Glu Thr Val Asp Ala Leu Val Glu Glu Val Ala Thr Phe Met
        35                  40                  45

Cys Ala Val Glu Ser Tyr Pro Gln Pro Glu Ile Ser Trp Thr Arg Asn
    50                  55                  60

Lys Ile Leu Ile Lys Leu Phe Asp Thr Arg Tyr Ser Ile Arg Glu Asn
65                  70                  75                  80

Gly Gln Leu Leu Thr Ile Leu Ser Val Glu Asp Ser Asp Asp Gly Ile
                85                  90                  95

Tyr Cys Cys Thr Ala Asn Asn Gly Val Gly Gly Ala Val Glu Ser Cys
            100                 105                 110

Gly Ala Leu Gln Val Lys Met Lys Pro Lys Ile Thr Arg Pro Pro Ile
        115                 120                 125

Asn Val Lys Ile Ile Glu Gly Leu Lys Ala Val Leu Pro Cys Thr Thr
    130                 135                 140

Met Gly Asn Pro Lys Pro Ser Val Ser Trp Ile Lys Gly Asp Ser Pro
145                 150                 155                 160

Leu Arg Glu Asn Ser Arg Ile Ala Val Leu Glu Ser Gly Ser Leu Arg
                165                 170                 175

Ile His Asn Val Gln Lys Glu Asp Ala Gly Gln Tyr Arg Cys Val Ala
            180                 185                 190
```

-continued

```
Lys  Asn  Ser  Leu  Gly  Thr  Ala  Tyr  Ser  Lys  Val  Val  Lys  Leu  Glu  Val
          195                 200                 205

Glu  Val  Phe  Ala  Arg  Ile  Leu  Arg  Ala  Pro  Glu  Ser  His  Asn  Val  Thr
     210                 215                 220

Phe  Gly  Ser  Phe  Val  Thr  Leu  His  Cys  Thr  Ala  Thr  Gly  Ile  Pro  Val
225                      230                 235                           240

Pro  Thr  Ile  Thr  Trp  Ile  Glu  Asn  Gly  Asn  Ala  Val  Ser  Ser  Gly  Ser
               245                      250                      255

Ile  Gln  Glu  Ser  Val  Lys  Asp  Arg  Val  Ile  Asp  Ser  Arg  Leu  Gln  Leu
               260                 265                      270

Phe  Ile  Thr  Lys  Pro  Gly  Leu  Tyr  Thr  Cys  Ile  Ala  Thr  Asn  Lys  His
          275                 280                      285

Gly  Glu  Lys  Phe  Ser  Thr  Ala  Lys  Ala  Ala  Ala  Thr  Ile  Ser  Ile  Ala
     290                 295                      300

Glu  Trp  Ser  Lys  Pro  Gln  Lys  Asp  Asn  Lys  Gly  Tyr  Cys  Ala  Gln  Tyr
305                      310                 315                           320

Arg  Gly  Glu  Val  Cys  Asn  Ala  Val  Leu  Ala  Lys  Asp  Ala  Leu  Val  Phe
                    325                 330                      335

Leu  Asn  Thr  Ser  Tyr  Ala  Asp  Pro  Glu  Glu  Ala  Gln  Glu  Leu  Leu  Val
               340                 345                      350

His  Thr  Ala  Trp  Asn  Glu  Leu  Lys  Val  Val  Ser  Pro  Val  Cys  Arg  Pro
          355                      360                 365

Ala  Ala  Glu  Ala  Leu  Leu  Cys  Asn  His  Ile  Phe  Gln  Glu  Cys  Ser  Pro
370                           375                 380

Gly  Val  Val  Pro  Thr  Pro  Ile  Pro  Ile  Cys  Arg  Glu  Tyr  Cys  Leu  Ala
385                      390                      395                      400

Val  Lys  Glu  Leu  Phe  Cys  Ala  Lys  Glu  Trp  Leu  Val  Met  Glu  Glu  Lys
               405                      410                           415

Thr  His  Arg  Gly  Leu  Tyr  Arg  Ser  Glu  Met  His  Leu  Leu  Ser  Val  Pro
               420                 425                      430

Glu  Cys  Ser  Lys  Leu  Pro  Ser  Met  His  Trp  Asp  Pro  Thr  Ala  Cys  Ala
          435                      440                 445

Arg  Leu  Pro  His  Leu  Asp  Tyr  Asn  Lys  Glu  Asn  Leu  Lys  Thr  Phe  Pro
     450                 455                      460

Pro  Met  Thr  Ser  Ser  Lys  Pro  Ser  Val  Asp  Ile  Pro  Asn  Leu  Pro  Ser
465                      470                 475                           480

Ser  Ser  Ser  Ser  Ser  Phe  Ser  Val  Ser  Pro  Thr  Tyr  Ser  Met  Thr  Val
                    485                 490                      495

Ile  Ile  Ser  Ile  Met  Ser  Ser  Phe  Ala  Ile  Phe  Val  Leu  Leu  Thr  Ile
               500                 505                      510

Thr  Thr  Leu  Tyr  Cys  Cys  Arg  Arg  Arg  Lys  Gln  Trp  Lys  Asn  Lys  Lys
          515                      520                 525

Arg  Glu  Ser  Ala  Ala  Val  Thr  Leu  Thr  Thr  Leu  Pro  Ser  Glu  Leu  Leu
     530                      535                      540

Leu  Asp  Arg  Leu  His  Pro  Asn  Pro  Met  Tyr  Gln  Arg  Met  Pro  Leu  Leu
545                      550                      555                      560

Leu  Asn  Pro  Lys  Leu  Leu  Ser  Leu  Glu  Tyr  Pro  Arg  Asn  Asn  Ile  Glu
               565                      570                      575

Tyr  Val  Arg  Asp  Ile  Gly  Glu  Gly  Ala  Phe  Gly  Arg  Val  Phe  Gln  Ala
               580                      585                      590

Arg  Ala  Pro  Gly  Leu  Leu  Pro  Tyr  Glu  Pro  Phe  Thr  Met  Val  Ala  Val
          595                      600                      605

Lys  Met  Leu  Lys  Glu  Glu  Ala  Ser  Ala  Asp  Met  Gln  Ala  Asp  Phe  Gln
```

|   |   |   | 610 |   |   |   | 615 |   |   |   | 620 |   |   |   |
|---|---|---|---|---|---|---|---|---|---|---|---|---|---|---|
| Arg 625 | Glu | Ala | Ala | Leu | Met 630 | Ala | Glu | Phe | Asp | Asn 635 | Pro | Asn | Ile | Val | Lys 640 |
| Leu | Leu | Gly | Val | Cys 645 | Ala | Val | Gly | Lys | Pro 650 | Met | Cys | Leu | Leu | Phe 655 | Glu |
| Tyr | Met | Ala | Tyr 660 | Gly | Asp | Leu | Asn | Glu 665 | Phe | Leu | Arg | Ser | Met 670 | Ser | Pro |
| His | Thr | Val 675 | Cys | Ser | Leu | Ser | His 680 | Ser | Asp | Leu | Ser | Met 685 | Arg | Ala | Gln |
| Val | Ser | Ser 690 | Pro | Gly | Pro | Pro 695 | Pro | Leu | Ser | Cys | Ala 700 | Glu | Gln | Leu | Cys |
| Ile | Ala | Arg | Gln | Val | Ala 710 | Ala | Gly | Met | Ala | Tyr 715 | Leu | Ser | Glu | Arg | Lys 720 |
| Phe | Val | His | Arg | Asp 725 | Leu | Ala | Thr | Arg | Asn 730 | Cys | Leu | Val | Gly | Glu 735 | Asn |
| Met | Val | Val | Lys 740 | Ile | Ala | Asp | Phe | Gly 745 | Leu | Ser | Arg | Asn | Ile 750 | Tyr | Ser |
| Ala | Asp | Tyr 755 | Tyr | Lys | Ala | Asn | Glu 760 | Asn | Asp | Ala | Ile | Pro 765 | Ile | Arg | Trp |
| Met | Pro 770 | Pro | Glu | Ser | Ile | Phe 775 | Tyr | Asn | Arg | Tyr | Thr 780 | Thr | Glu | Ser | Asp |
| Val 785 | Trp | Ala | Tyr | Gly | Val 790 | Val | Leu | Trp | Glu | Ile 795 | Phe | Ser | Tyr | Gly | Leu 800 |
| Gln | Pro | Tyr | Tyr | Gly 805 | Met | Ala | His | Glu | Glu 810 | Val | Ile | Tyr | Tyr | Val 815 | Arg |
| Asp | Gly | Asn | Ile 820 | Leu | Ser | Cys | Pro | Glu 825 | Asn | Cys | Pro | Val | Glu 830 | Leu | Tyr |
| Asn | Leu | Met 835 | Arg | Leu | Cys | Trp | Ser 840 | Lys | Leu | Pro | Ala | Asp 845 | Arg | Pro | Ser |
| Phe | Thr 850 | Ser | Ile | His | Arg | Ile 855 | Leu | Glu | Arg | Met | Cys 860 | Glu | Arg | Ala | Glu |
| Gly 865 | Thr | Val | Ser | Val |   |   |   |   |   |   |   |   |   |   |   |

( 2 ) INFORMATION FOR SEQ ID NO:30:

( i ) SEQUENCE CHARACTERISTICS:
        ( A ) LENGTH: 1940 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Rat Agrin
        ( B ) LOCATION: 1...1940
        ( D ) OTHER INFORMATION:

( x i ) SEQUENCE DESCRIPTION: SEQ ID NO:30:

| Met 1 | Pro | Pro | Leu | Pro 5 | Leu | Glu | His | Arg | Pro 10 | Arg | Gln | Glu | Pro | Gly 15 | Ala |
| Ser | Met | Leu | Val 20 | Arg | Tyr | Phe | Met | Ile 25 | Pro | Cys | Asn | Ile | Cys 30 | Leu | Ile |
| Leu | Leu | Ala 35 | Thr | Ser | Thr | Leu | Gly 40 | Phe | Ala | Val | Leu | Leu 45 | Phe | Leu | Ser |
| Asn | Tyr 50 | Lys | Pro | Gly | Ile | His 55 | Phe | Thr | Pro | Ala | Pro 60 | Pro | Thr | Pro | Pro |

| | | | | | | | | | | | | | | | |
|---|---|---|---|---|---|---|---|---|---|---|---|---|---|---|---|
|Asp|Val|Cys|Arg|Gly|Met|Leu|Cys|Gly|Phe|Gly|Ala|Val|Cys|Glu|Pro|
|65| | | |70| | | |75| | | |80| | | |
|Ser|Val|Glu|Asp|Pro|Gly|Arg|Ala|Ser|Cys|Val|Cys|Lys|Lys|Asn|Ala|
| | | | |85| | | |90| | | |95| | | |
|Cys|Pro|Ala|Thr|Val|Ala|Pro|Val|Cys|Gly|Ser|Asp|Ala|Ser|Thr|Tyr|
| | | |100| | | |105| | | |110| | | | |
|Ser|Asn|Glu|Cys|Glu|Leu|Gln|Arg|Ala|Gln|Cys|Asn|Gln|Gln|Arg|Arg|
| | |115| | | |120| | | |125| | | | | |
|Ile|Arg|Leu|Leu|Arg|Gln|Gly|Pro|Cys|Gly|Ser|Arg|Asp|Pro|Cys|Ala|
| |130| | | |135| | | |140| | | | | | |
|Asn|Val|Thr|Cys|Ser|Phe|Gly|Ser|Thr|Cys|Val|Pro|Ser|Ala|Asp|Gly|
|145| | | |150| | | |155| | | |160| | | | |
|Gln|Thr|Ala|Ser|Cys|Leu|Cys|Pro|Thr|Cys|Phe|Gly|Ala|Pro|Asp|
| | | |165| | | |170| | | |175| | | | |
|Gly|Thr|Val|Cys|Gly|Ser|Asp|Gly|Val|Asp|Tyr|Pro|Ser|Glu|Cys|Gln|
| | |180| | | |185| | | |190| | | | | |
|Leu|Leu|Ser|His|Ala|Cys|Ala|Ser|Gln|Glu|His|Ile|Phe|Lys|Lys|Phe|
| |195| | | |200| | | |205| | | | | | |
|Asn|Gly|Pro|Cys|Asp|Pro|Cys|Gln|Gly|Ser|Met|Ser|Asp|Leu|Asn|His|
| |210| | | |215| | | |220| | | | | | |
|Ile|Cys|Arg|Val|Asn|Pro|Arg|Thr|Arg|His|Pro|Glu|Met|Leu|Leu|Arg|
|225| | | |230| | | |235| | | |240| | | | |
|Pro|Glu|Asn|Cys|Pro|Ala|Gln|His|Thr|Pro|Ile|Cys|Gly|Asp|Asp|Gly|
| | | |245| | | |250| | | |255| | | | |
|Val|Thr|Tyr|Glu|Asn|Asp|Cys|Val|Met|Ser|Arg|Ile|Gly|Ala|Thr|Arg|
| | |260| | | |265| | | |270| | | | | |
|Gly|Leu|Leu|Leu|Gln|Lys|Val|Arg|Ser|Gly|Gln|Cys|Gln|Thr|Arg|Asp|
| |275| | | |280| | | |285| | | | | | |
|Gln|Cys|Pro|Glu|Thr|Cys|Gln|Phe|Asn|Ser|Val|Cys|Leu|Ser|Arg|Arg|
|290| | | |295| | | |300| | | | | | | |
|Gly|Arg|Pro|His|Cys|Ser|Cys|Asp|Arg|Val|Thr|Cys|Asp|Gly|Ser|Tyr|
|305| | | |310| | | |315| | | |320| | | | |
|Arg|Pro|Val|Cys|Ala|Gln|Asp|Gly|His|Thr|Tyr|Asn|Asn|Asp|Cys|Trp|
| | | |325| | | |330| | | |335| | | | |
|Arg|Gln|Gln|Ala|Glu|Cys|Arg|Gln|Arg|Ala|Ile|Pro|Pro|Lys|His|
| | |340| | | |345| | | |350| | | | | |
|Gln|Gly|Pro|Cys|Asp|Gln|Thr|Pro|Ser|Pro|Cys|His|Gly|Val|Gln|Cys|
| |355| | | |360| | | |365| | | | | | |
|Ala|Phe|Gly|Ala|Val|Cys|Thr|Val|Lys|Asn|Gly|Lys|Ala|Glu|Cys|Glu|
| |370| | | |375| | | |380| | | | | | |
|Cys|Gln|Arg|Val|Cys|Ser|Gly|Ile|Tyr|Asp|Pro|Val|Cys|Gly|Ser|Asp|
|385| | | |390| | | |395| | | | | | |400|
|Gly|Val|Thr|Tyr|Gly|Ser|Val|Cys|Glu|Leu|Glu|Ser|Met|Ala|Cys|Thr|
| | | |405| | | |410| | | |415| | | | |
|Leu|Gly|Arg|Glu|Ile|Gln|Val|Ala|Arg|Arg|Gly|Pro|Cys|Asp|Pro|Cys|
| | |420| | | |425| | | |430| | | | | |
|Gly|Gln|Cys|Arg|Phe|Gly|Ser|Leu|Cys|Glu|Val|Glu|Thr|Gly|Arg|Cys|
| |435| | | |440| | | |445| | | | | | |
|Val|Cys|Pro|Ser|Glu|Cys|Val|Glu|Ser|Ala|Gln|Pro|Val|Cys|Gly|Ser|
| |450| | | |455| | | |460| | | | | | |
|Asp|Gly|His|Thr|Tyr|Ala|Ser|Glu|Cys|Glu|Leu|His|Val|His|Ala|Cys|
|465| | | |470| | | |475| | | |480| | | | |
|Thr|His|Gln|Ile|Ser|Leu|Tyr|Val|Ala|Ser|Ala|Gly|His|Cys|Gln|Thr|
| | | |485| | | |490| | | |495| | | | |

```
Cys Gly Glu Lys Val Cys Thr Phe Gly Ala Val Cys Ser Ala Gly Gln
            500             505             510
Cys Val Cys Pro Arg Cys Glu His Pro Pro Gly Pro Val Cys Gly
        515             520             525
Ser Asp Gly Val Thr Tyr Leu Ser Ala Cys Glu Leu Arg Glu Ala Ala
530             535             540
Cys Gln Gln Gln Val Gln Ile Glu Glu Ala His Ala Gly Pro Cys Glu
545             550             555             560
Pro Ala Glu Cys Gly Ser Gly Gly Ser Gly Ser Gly Glu Asp Asp Glu
                565             570             575
Cys Glu Gln Glu Leu Cys Arg Gln Arg Gly Gly Ile Trp Asp Glu Asp
            580             585             590
Ser Glu Asp Gly Pro Cys Val Cys Asp Phe Ser Cys Gln Ser Val Pro
        595             600             605
Arg Ser Pro Val Cys Gly Ser Asp Gly Val Thr Tyr Gly Thr Glu Cys
    610             615             620
Asp Leu Lys Lys Ala Arg Cys Glu Ser Gln Gln Glu Leu Tyr Val Ala
625             630             635             640
Ala Gln Gly Ala Cys Arg Gly Pro Thr Leu Ala Pro Leu Leu Pro Val
                645             650             655
Ala Phe Pro His Cys Ala Gln Thr Pro Tyr Gly Cys Cys Gln Asp Asn
            660             665             670
Phe Thr Ala Ala Gln Gly Val Gly Leu Ala Gly Cys Pro Ser Thr Cys
        675             680             685
His Cys Asn Pro His Gly Ser Tyr Ser Gly Thr Cys Asp Pro Ala Thr
    690             695             700
Gly Gln Cys Ser Cys Arg Pro Gly Val Gly Gly Leu Arg Cys Asp Arg
705             710             715             720
Cys Glu Pro Gly Phe Trp Asn Phe Arg Gly Ile Val Thr Asp Gly His
                725             730             735
Ser Gly Cys Thr Pro Cys Ser Cys Asp Pro Arg Gly Ala Val Arg Asp
            740             745             750
Asp Cys Glu Gln Met Thr Gly Leu Cys Ser Cys Arg Pro Gly Val Ala
        755             760             765
Gly Pro Lys Cys Gly Gln Cys Pro Asp Gly Gln Val Leu Gly His Leu
770             775             780
Gly Cys Glu Ala Asp Pro Met Thr Pro Val Thr Cys Val Glu Ile His
785             790             795             800
Cys Glu Phe Gly Ala Ser Cys Val Glu Lys Ala Gly Phe Ala Gln Cys
                805             810             815
Ile Cys Pro Thr Leu Thr Cys Pro Glu Ala Asn Ser Thr Lys Val Cys
            820             825             830
Gly Ser Asp Gly Val Thr Tyr Gly Asn Glu Cys Gln Leu Lys Ala Ile
        835             840             845
Ala Cys Arg Gln Arg Leu Asp Ile Ser Thr Gln Ser Leu Gly Pro Cys
    850             855             860
Gln Glu Ser Val Thr Pro Gly Ala Ser Pro Thr Ser Ala Ser Met Thr
865             870             875             880
Thr Pro Arg His Ile Leu Ser Lys Thr Leu Pro Phe Pro His Asn Ser
                885             890             895
Leu Pro Leu Ser Pro Gly Ser Thr Thr His Asp Trp Pro Thr Pro Leu
            900             905             910
Pro Ile Ser Pro His Thr Thr Val Ser Ile Pro Arg Ser Thr Ala Trp
```

-continued

|     |     |     | 915 |     |     |     |     | 920 |     |     |     |     | 925 |     |
| --- | --- | --- | --- | --- | --- | --- | --- | --- | --- | --- | --- | --- | --- | --- |
| Pro | Val | Leu | Thr | Val | Pro | Pro | Thr | Ala | Ala | Ala | Ser | Asp | Val | Thr | Ser |
|     |     | 930 |     |     |     | 935 |     |     |     |     | 940 |     |     |     |
| Leu | Ala | Thr | Ser | Ile | Phe | Ser | Glu | Ser | Gly | Ser | Ala | Asn | Gly | Ser | Gly |
| 945 |     |     |     |     | 950 |     |     |     |     | 955 |     |     |     |     | 960 |
| Asp | Glu | Glu | Leu | Ser | Gly | Asp | Glu | Ala | Ser | Gly | Gly | Gly | Ser | Gly |
|     |     |     |     | 965 |     |     |     |     | 970 |     |     |     |     | 975 |
| Gly | Leu | Glu | Pro | Pro | Val | Gly | Ser | Ile | Val | Val | Thr | His | Gly | Pro | Pro |
|     |     |     |     | 980 |     |     |     |     | 985 |     |     |     |     | 990 |
| Ile | Glu | Arg | Ala | Ser | Cys | Tyr | Asn | Ser | Pro | Leu | Gly | Cys | Cys | Ser | Asp |
|     |     |     | 995 |     |     |     | 1000 |     |     |     |     | 1005 |     |     |
| Gly | Lys | Thr | Pro | Ser | Leu | Asp | Ser | Glu | Gly | Ser | Asn | Cys | Pro | Ala | Thr |
|     |     |     | 1010 |     |     |     | 1015 |     |     |     |     | 1020 |     |     |     |
| Lys | Ala | Phe | Gln | Gly | Val | Leu | Glu | Leu | Glu | Gly | Val | Glu | Gly | Gln | Glu |
| 1025 |     |     |     |     | 1030 |     |     |     |     | 1035 |     |     |     |     | 1040 |
| Leu | Phe | Tyr | Thr | Pro | Glu | Met | Ala | Asp | Pro | Lys | Ser | Glu | Leu | Phe | Gly |
|     |     |     |     | 1045 |     |     |     |     | 1050 |     |     |     |     | 1055 |
| Glu | Thr | Ala | Arg | Ser | Ile | Glu | Ser | Thr | Leu | Asp | Asp | Leu | Phe | Arg | Asn |
|     |     |     |     | 1060 |     |     |     |     | 1065 |     |     |     |     | 1070 |
| Ser | Asp | Val | Lys | Lys | Asp | Phe | Trp | Ser | Val | Arg | Leu | Arg | Glu | Leu | Gly |
|     |     |     |     | 1075 |     |     |     |     | 1080 |     |     |     |     | 1085 |
| Pro | Gly | Lys | Leu | Val | Arg | Ala | Ile | Val | Asp | Val | His | Phe | Asp | Pro | Thr |
|     |     |     | 1090 |     |     |     |     | 1095 |     |     |     |     | 1100 |     |
| Thr | Ala | Phe | Gln | Ala | Ser | Asp | Val | Gly | Gln | Ala | Leu | Leu | Arg | Gln | Ile |
| 1105 |     |     |     |     | 1110 |     |     |     |     | 1115 |     |     |     |     | 1120 |
| Gln | Val | Ser | Arg | Pro | Trp | Ala | Leu | Ala | Val | Arg | Arg | Pro | Leu | Gln | Glu |
|     |     |     |     | 1125 |     |     |     |     | 1130 |     |     |     |     | 1135 |
| His | Val | Arg | Phe | Leu | Asp | Phe | Asp | Trp | Phe | Pro | Thr | Phe | Phe | Thr | Gly |
|     |     |     |     | 1140 |     |     |     |     | 1145 |     |     |     |     | 1150 |
| Ala | Ala | Thr | Gly | Thr | Thr | Ala | Ala | Met | Ala | Thr | Ala | Arg | Ala | Thr | Thr |
|     |     |     |     | 1155 |     |     |     |     | 1160 |     |     |     |     | 1165 |
| Val | Ser | Arg | Leu | Pro | Ala | Ser | Ser | Val | Thr | Pro | Arg | Val | Tyr | Pro | Ser |
|     |     |     | 1170 |     |     |     |     | 1175 |     |     |     |     | 1180 |     |
| His | Thr | Ser | Arg | Pro | Val | Gly | Arg | Thr | Thr | Ala | Pro | Pro | Thr | Thr | Arg |
| 1185 |     |     |     |     | 1190 |     |     |     |     | 1195 |     |     |     |     | 1200 |
| Arg | Pro | Pro | Thr | Thr | Ala | Thr | Asn | Met | Asp | Arg | Pro | Arg | Thr | Pro | Gly |
|     |     |     |     | 1205 |     |     |     |     | 1210 |     |     |     |     | 1215 |
| His | Gln | Gln | Pro | Ser | Lys | Ser | Cys | Asp | Ser | Gln | Pro | Cys | Leu | His | Gly |
|     |     |     |     | 1220 |     |     |     |     | 1225 |     |     |     |     | 1230 |
| Gly | Thr | Cys | Gln | Asp | Gln | Asp | Ser | Gly | Lys | Gly | Phe | Thr | Cys | Ser | Cys |
|     |     |     | 1235 |     |     |     |     | 1240 |     |     |     |     | 1245 |     |
| Thr | Ala | Gly | Arg | Gly | Gly | Ser | Val | Cys | Glu | Lys | Val | Gln | Pro | Pro | Ser |
|     |     |     | 1250 |     |     |     |     | 1255 |     |     |     |     | 1260 |     |
| Met | Pro | Ala | Phe | Lys | Gly | His | Ser | Phe | Leu | Ala | Phe | Pro | Thr | Leu | Arg |
| 1265 |     |     |     |     | 1270 |     |     |     |     | 1275 |     |     |     |     | 1280 |
| Ala | Tyr | His | Thr | Leu | Arg | Leu | Ala | Leu | Glu | Phe | Arg | Ala | Leu | Glu | Thr |
|     |     |     |     | 1285 |     |     |     |     | 1290 |     |     |     |     | 1295 |
| Glu | Gly | Leu | Leu | Leu | Tyr | Asn | Gly | Asn | Ala | Arg | Gly | Lys | Asp | Phe | Leu |
|     |     |     |     | 1300 |     |     |     |     | 1305 |     |     |     |     | 1310 |
| Ala | Leu | Ala | Leu | Leu | Asp | Gly | Arg | Val | Gln | Phe | Arg | Phe | Asp | Thr | Gly |
|     |     |     |     | 1315 |     |     |     |     | 1320 |     |     |     |     | 1325 |
| Ser | Gly | Pro | Ala | Val | Leu | Thr | Ser | Leu | Val | Pro | Val | Glu | Pro | Gly | Arg |
|     |     |     |     | 1330 |     |     |     |     | 1335 |     |     |     |     | 1340 |

```
Trp His Arg Leu Glu Leu Ser Arg His Trp Arg Gln Gly Thr Leu Ser
1345                1350                1355                1360

Val Asp Gly Glu Thr Pro Val Val Gly Glu Ser Pro Ser Gly Thr Asp
            1365                1370                1375

Gly Leu Asn Leu Asp Thr Asn Leu Tyr Val Gly Gly Ile Pro Glu Glu
        1380                1385                1390

Gln Val Ala Met Val Leu Asp Arg Thr Ser Val Gly Val Gly Leu Lys
    1395                1400                1405

Gly Cys Ile Arg Met Leu Asp Ile Asn Asn Gln Leu Glu Leu Ser
1410                1415                1420

Asp Trp Gln Arg Ala Ala Val Gln Ser Ser Gly Val Gly Glu Cys Gly
1425                1430                1435                1440

Asp His Pro Cys Leu Pro Asn Pro Cys His Gly Gly Ala Leu Cys Gln
                1445                1450                1455

Ala Leu Glu Ala Gly Met Phe Leu Cys Gln Cys Pro Pro Gly Arg Phe
1460                1465                1470

Gly Pro Thr Cys Ala Asp Glu Lys Ser Pro Cys Gln Pro Asn Pro Cys
            1475                1480                1485

His Gly Ala Ala Pro Cys Arg Val Leu Ser Ser Gly Gly Ala Lys Cys
        1490                1495                1500

Glu Cys Pro Leu Gly Arg Ser Gly Thr Phe Cys Gln Thr Val Leu Glu
1505                1510                1515                1520

Thr Ala Gly Ser Arg Pro Phe Leu Ala Asp Phe Asn Gly Phe Ser Tyr
                1525                1530                1535

Leu Glu Leu Lys Gly Leu His Thr Phe Glu Arg Asp Leu Gly Glu Lys
            1540                1545                1550

Met Ala Leu Glu Met Val Phe Leu Ala Arg Gly Pro Ser Gly Leu Leu
        1555                1560                1565

Leu Tyr Asn Gly Gln Lys Thr Asp Gly Lys Gly Asp Phe Val Ser Leu
    1570                1575                1580

Ala Leu His Asn Arg His Leu Glu Phe Cys Tyr Asp Leu Gly Lys Gly
1585                1590                1595                1600

Ala Ala Val Ile Arg Ser Lys Glu Pro Ile Ala Leu Gly Thr Trp Val
                1605                1610                1615

Arg Val Phe Leu Glu Arg Asn Gly Arg Lys Gly Ala Leu Gln Val Gly
            1620                1625                1630

Asp Gly Pro Arg Val Leu Gly Glu Ser Pro Lys Ser Arg Lys Val Pro
        1635                1640                1645

His Thr Met Leu Asn Leu Lys Glu Pro Leu Tyr Ile Gly Gly Ala Pro
    1650                1655                1660

Asp Phe Ser Lys Leu Ala Arg Gly Ala Ala Val Ser Ser Gly Phe Ser
1665                1670                1675                1680

Gly Val Ile Gln Leu Val Ser Leu Arg Gly His Gln Leu Leu Thr Gln
                1685                1690                1695

Glu His Val Leu Arg Ala Val Asp Val Ser Pro Phe Ala Asp His Pro
            1700                1705                1710

Cys Thr Gln Ala Leu Gly Asn Pro Cys Leu Asn Gly Gly Ser Cys Val
        1715                1720                1725

Pro Arg Glu Ala Thr Tyr Glu Cys Leu Cys Pro Gly Gly Phe Ser Gly
    1730                1735                1740

Leu His Cys Glu Lys Gly Leu Val Glu Lys Ser Val Gly Asp Leu Glu
1745                1750                1755                1760

Thr Leu Ala Phe Asp Gly Arg Thr Tyr Ile Glu Tyr Leu Asn Ala Val
                1765                1770                1775
```

```
Ile  Glu  Ser  Glu  Lys  Ala  Leu  Gln  Ser  Asn  His  Phe  Glu  Leu  Ser  Leu
               1780                    1785                    1790

Arg  Thr  Glu  Ala  Thr  Gln  Gly  Leu  Val  Leu  Trp  Ile  Gly  Lys  Ala  Ala
               1795                    1800                    1805

Glu  Arg  Ala  Asp  Tyr  Met  Ala  Leu  Ala  Ile  Val  Asp  Gly  His  Leu  Gln
               1810                    1815                    1820

Leu  Ser  Tyr  Asp  Leu  Gly  Ser  Gln  Pro  Val  Val  Leu  Arg  Ser  Thr  Val
1825                    1830                    1835                         1840

Lys  Val  Asn  Thr  Asn  Arg  Trp  Leu  Arg  Ile  Arg  Ala  His  Arg  Glu  His
                    1845                    1850                    1855

Arg  Glu  Gly  Ser  Leu  Gln  Val  Gly  Asn  Glu  Ala  Pro  Val  Thr  Gly  Ser
               1860                    1865                    1870

Ser  Pro  Leu  Gly  Ala  Thr  Gln  Leu  Asp  Thr  Asp  Gly  Ala  Leu  Trp  Leu
               1875                    1880                    1885

Gly  Gly  Leu  Gln  Lys  Leu  Pro  Val  Gly  Gln  Ala  Leu  Pro  Lys  Ala  Tyr
               1890                    1895                    1900

Gly  Thr  Gly  Phe  Val  Gly  Cys  Leu  Arg  Asp  Val  Val  Val  Gly  His  Arg
1905                    1910                    1915                         1920

Gln  Leu  His  Leu  Leu  Glu  Asp  Ala  Val  Thr  Lys  Pro  Glu  Leu  Arg  Pro
                    1925                    1930                    1935

Cys  Pro  Thr  Pro
               1940
```

(2) INFORMATION FOR SEQ ID NO:31:

(i) SEQUENCE CHARACTERISTICS:
        (A) LENGTH: 1479 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Coding Sequence
        (B) LOCATION: 1...1476
        (D) OTHER INFORMATION:
        (A) NAME/KEY: Human Agrin
        (B) LOCATION: 1...1479
        (D) OTHER INFORMATION:

(xi) SEQUENCE DESCRIPTION: SEQ ID NO:31:

```
ATG  TCT  GCA  CTT  CTG  ATC  CTA  GCT  CTT  GTT  GGA  GCT  GCA  GTT  GCT  GAC        48
Met  Ser  Ala  Leu  Leu  Ile  Leu  Ala  Leu  Val  Gly  Ala  Ala  Val  Ala  Asp
1                   5                        10                      15

TAC  AAA  GAC  GAT  GAC  GAC  AAG  AAG  AGC  CCC  TGC  CAG  CCC  AAC  CCC  TGC        96
Tyr  Lys  Asp  Asp  Asp  Asp  Lys  Lys  Ser  Pro  Cys  Gln  Pro  Asn  Pro  Cys
               20                       25                      30

CAT  GGG  GCG  GCG  CCC  TGC  CGT  GTG  CTG  CCC  GAG  GGT  GGT  GCT  CAG  TGC       144
His  Gly  Ala  Ala  Pro  Cys  Arg  Val  Leu  Pro  Glu  Gly  Gly  Ala  Gln  Cys
               35                       40                      45

GAG  TGC  CCC  CTG  GGG  CGT  GAG  GGC  ACC  TTC  TGC  CAG  ACA  GCC  TCG  GGG       192
Glu  Cys  Pro  Leu  Gly  Arg  Glu  Gly  Thr  Phe  Cys  Gln  Thr  Ala  Ser  Gly
     50                       55                      60

CAG  GAC  GGC  TCT  GGG  CCC  TTC  CTG  GCT  GAC  TTC  AAC  GGC  TTC  TCC  CAC       240
Gln  Asp  Gly  Ser  Gly  Pro  Phe  Leu  Ala  Asp  Phe  Asn  Gly  Phe  Ser  His
65                       70                      75                      80

CTG  GAG  CTG  AGA  GGC  CTG  CAC  ACC  TTT  GCA  CGG  GAC  CTG  GGG  GAG  AAG       288
Leu  Glu  Leu  Arg  Gly  Leu  His  Thr  Phe  Ala  Arg  Asp  Leu  Gly  Glu  Lys
                    85                       90                      95

ATG  GCG  CTG  GAG  GTC  GTG  TTC  CTG  GCA  CGA  GGC  CCC  AGC  GGC  CTC  CTG       336
```

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
| Met | Ala | Leu | Glu | Val | Val | Phe | Leu | Ala | Arg | Gly | Pro | Ser | Gly | Leu | Leu |     |
|     |     |     | 100 |     |     |     | 105 |     |     |     |     | 110 |     |     |     |     |
| CTC | TAC | AAC | GGG | CAG | AAG | ACG | GAC | GGC | AAG | GGG | GAC | TTC | GTG | TCG | CTG | 384 |
| Leu | Tyr | Asn | Gly | Gln | Lys | Thr | Asp | Gly | Lys | Gly | Asp | Phe | Val | Ser | Leu |     |
|     |     | 115 |     |     |     | 120 |     |     |     |     | 125 |     |     |     |     |     |
| GCA | CTG | CGG | GAC | CGC | CGC | CTG | GAG | TTC | CGC | TAC | GAC | CTG | GGC | AAG | GGG | 432 |
| Ala | Leu | Arg | Asp | Arg | Arg | Leu | Glu | Phe | Arg | Tyr | Asp | Leu | Gly | Lys | Gly |     |
|     | 130 |     |     |     |     | 135 |     |     |     |     | 140 |     |     |     |     |     |
| GCA | GCG | GTC | ATC | AGG | AGC | AGG | GAG | CCA | GTC | ACC | CTG | GGA | GCC | TGG | ACC | 480 |
| Ala | Ala | Val | Ile | Arg | Ser | Arg | Glu | Pro | Val | Thr | Leu | Gly | Ala | Trp | Thr |     |
| 145 |     |     |     |     | 150 |     |     |     |     | 155 |     |     |     |     | 160 |     |
| AGG | GTC | TCA | CTG | GAG | CGA | AAC | GGC | CGC | AAG | GGT | GCC | CTG | CGT | GTG | GGC | 528 |
| Arg | Val | Ser | Leu | Glu | Arg | Asn | Gly | Arg | Lys | Gly | Ala | Leu | Arg | Val | Gly |     |
|     |     |     |     | 165 |     |     |     |     | 170 |     |     |     |     | 175 |     |     |
| GAC | GGC | CCC | CGT | GTG | TTG | GGG | GAG | TCC | CCG | AAA | TCC | CGC | AAG | GTT | CCG | 576 |
| Asp | Gly | Pro | Arg | Val | Leu | Gly | Glu | Ser | Pro | Lys | Ser | Arg | Lys | Val | Pro |     |
|     |     |     | 180 |     |     |     |     | 185 |     |     |     |     | 190 |     |     |     |
| CAC | ACC | GTC | CTC | AAC | CTG | AAG | GAG | CCG | CTC | TAC | GTA | GGG | GGC | GCT | CCC | 624 |
| His | Thr | Val | Leu | Asn | Leu | Lys | Glu | Pro | Leu | Tyr | Val | Gly | Gly | Ala | Pro |     |
|     |     | 195 |     |     |     |     | 200 |     |     |     |     | 205 |     |     |     |     |
| GAC | TTC | AGC | AAG | CTG | GCC | CGT | GCT | GCT | GCC | GTG | TCC | TCT | GGC | TTC | GAC | 672 |
| Asp | Phe | Ser | Lys | Leu | Ala | Arg | Ala | Ala | Ala | Val | Ser | Ser | Gly | Phe | Asp |     |
|     | 210 |     |     |     |     | 215 |     |     |     |     | 220 |     |     |     |     |     |
| GGC | GCC | ATC | CAG | CTG | GTC | TCC | CTC | GGA | GGC | CGC | CAG | CTG | CTG | ACC | CCG | 720 |
| Gly | Ala | Ile | Gln | Leu | Val | Ser | Leu | Gly | Gly | Arg | Gln | Leu | Leu | Thr | Pro |     |
| 225 |     |     |     |     | 230 |     |     |     |     | 235 |     |     |     |     | 240 |     |
| GAG | CAC | GTG | CTG | CGG | CAG | GTG | GAC | GTC | ACG | TCC | TTT | GCA | GGT | CAC | CCC | 768 |
| Glu | His | Val | Leu | Arg | Gln | Val | Asp | Val | Thr | Ser | Phe | Ala | Gly | His | Pro |     |
|     |     |     |     | 245 |     |     |     |     | 250 |     |     |     |     | 255 |     |     |
| TGC | ACC | CGG | GCC | TCA | GGC | CAC | CCC | TGC | CTC | AAT | GGG | GCC | TCC | TGC | GTC | 816 |
| Cys | Thr | Arg | Ala | Ser | Gly | His | Pro | Cys | Leu | Asn | Gly | Ala | Ser | Cys | Val |     |
|     |     |     | 260 |     |     |     |     | 265 |     |     |     |     | 270 |     |     |     |
| CCG | AGG | GAG | GCT | GCC | TAT | GTG | TGC | CTG | TGT | CCC | GGG | GGA | TTC | TCA | GGA | 864 |
| Pro | Arg | Glu | Ala | Ala | Tyr | Val | Cys | Leu | Cys | Pro | Gly | Gly | Phe | Ser | Gly |     |
|     |     | 275 |     |     |     |     | 280 |     |     |     |     | 285 |     |     |     |     |
| CCG | CAC | TGC | GAG | AAG | GGG | CTG | GTG | GAG | AAG | TCA | GCG | GGG | GAC | GTG | GAT | 912 |
| Pro | His | Cys | Glu | Lys | Gly | Leu | Val | Glu | Lys | Ser | Ala | Gly | Asp | Val | Asp |     |
| 290 |     |     |     |     | 295 |     |     |     |     | 300 |     |     |     |     |     |     |
| ACC | TTG | GCC | TTT | GAC | GGG | CGG | ACC | TTT | GTC | GAG | TAC | CTC | AAC | GCT | GTG | 960 |
| Thr | Leu | Ala | Phe | Asp | Gly | Arg | Thr | Phe | Val | Glu | Tyr | Leu | Asn | Ala | Val |     |
| 305 |     |     |     | 310 |     |     |     |     | 315 |     |     |     |     | 320 |     |     |
| ACC | GAG | AGC | GAA | CTG | GCC | AAT | GAG | ATC | CCC | GTC | GAG | AAG | GCA | CTG | CAG | 1008 |
| Thr | Glu | Ser | Glu | Leu | Ala | Asn | Glu | Ile | Pro | Val | Glu | Lys | Ala | Leu | Gln |     |
|     |     |     |     |     | 325 |     |     |     | 330 |     |     |     |     | 335 |     |     |
| AGC | AAC | CAC | TTT | GAA | CTG | AGC | CTG | CGC | ACT | GAG | GCC | ACG | CAG | GGG | CTG | 1056 |
| Ser | Asn | His | Phe | Glu | Leu | Ser | Leu | Arg | Thr | Glu | Ala | Thr | Gln | Gly | Leu |     |
|     |     |     | 340 |     |     |     |     | 345 |     |     |     |     | 350 |     |     |     |
| GTG | CTC | TGG | AGT | GGC | AAG | GCC | ACG | GAG | CGG | GCA | GAC | TAT | GTG | GCA | CTG | 1104 |
| Val | Leu | Trp | Ser | Gly | Lys | Ala | Thr | Glu | Arg | Ala | Asp | Tyr | Val | Ala | Leu |     |
|     |     | 355 |     |     |     |     | 360 |     |     |     |     | 365 |     |     |     |     |
| GCC | ATT | GTG | GAC | GGG | CAC | CTG | CAA | CTG | AGC | TAC | AAC | CTG | GGC | TCC | CAG | 1152 |
| Ala | Ile | Val | Asp | Gly | His | Leu | Gln | Leu | Ser | Tyr | Asn | Leu | Gly | Ser | Gln |     |
|     | 370 |     |     |     |     | 375 |     |     |     |     | 380 |     |     |     |     |     |
| CCC | GTG | GTG | CTG | CGT | TCC | ACC | GTG | CCC | GTC | AAC | ACC | AAC | CGC | TGG | TTG | 1200 |
| Pro | Val | Val | Leu | Arg | Ser | Thr | Val | Pro | Val | Asn | Thr | Asn | Arg | Trp | Leu |     |
| 385 |     |     |     |     | 390 |     |     |     |     | 395 |     |     |     |     | 400 |     |
| CGG | GTC | GTG | GCA | CAT | AGG | GAG | CAG | AGG | GAA | GGT | TCC | CTG | CAG | GTG | GGC | 1248 |
| Arg | Val | Val | Ala | His | Arg | Glu | Gln | Arg | Glu | Gly | Ser | Leu | Gln | Val | Gly |     |
|     |     |     |     | 405 |     |     |     |     | 410 |     |     |     |     | 415 |     |     |
| AAT | GAG | GCC | CCT | GTG | ACC | GGC | TCC | TCC | CCG | CTG | GGC | GCC | ACG | CAG | CTG | 1296 |

|     |     |     |     |     |     |     |     |     |     |     |     |     |     |     |     |
|-----|-----|-----|-----|-----|-----|-----|-----|-----|-----|-----|-----|-----|-----|-----|-----|
| Asn | Glu | Ala | Pro<br>420 | Val | Thr | Gly | Ser | Ser<br>425 | Pro | Leu | Gly | Ala | Thr<br>430 | Gln | Leu |

| GAC | ACT | GAT | GGA | GCC | CTG | TGG | CTT | GGG | GGC | CTG | CCG | GAG | CTG | CCC | GTG | 1344 |
|-----|-----|-----|-----|-----|-----|-----|-----|-----|-----|-----|-----|-----|-----|-----|-----|------|
| Asp | Thr | Asp<br>435 | Gly | Ala | Leu | Trp | Leu<br>440 | Gly | Gly | Leu | Pro | Glu<br>445 | Leu | Pro | Val |  |

| GGC | CCA | GCA | CTG | CCC | AAG | GCC | TAC | GGC | ACA | GGC | TTT | GTG | GGC | TGC | TTG | 1392 |
|-----|-----|-----|-----|-----|-----|-----|-----|-----|-----|-----|-----|-----|-----|-----|-----|------|
| Gly | Pro<br>450 | Ala | Leu | Pro | Lys | Ala<br>455 | Tyr | Gly | Thr | Gly | Phe<br>460 | Val | Gly | Cys | Leu |  |

| CGG | GAC | GTG | GTG | GTG | GGC | CGG | CAC | CCG | CTG | CAC | CTG | CTG | GAG | GAC | GCC | 1440 |
|-----|-----|-----|-----|-----|-----|-----|-----|-----|-----|-----|-----|-----|-----|-----|-----|------|
| Arg<br>465 | Asp | Val | Val | Val | Gly<br>470 | Arg | His | Pro | Leu | His<br>475 | Leu | Leu | Glu | Asp | Ala<br>480 |  |

| GTC | ACC | AAG | CCA | GAG | CTG | CGG | CCC | TGC | CCC | ACC | CCA | TGA |     |     |     | 1479 |
|-----|-----|-----|-----|-----|-----|-----|-----|-----|-----|-----|-----|-----|-----|-----|-----|------|
| Val | Thr | Lys | Pro | Glu<br>485 | Leu | Arg | Pro | Cys | Pro<br>490 | Thr | Pro |  |     |     |     |  |

( 2 ) INFORMATION FOR SEQ ID NO:32:

( i ) SEQUENCE CHARACTERISTICS:
        ( A ) LENGTH: 492 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( i x ) FEATURE:
        ( A ) NAME/KEY: Human Agrin
        ( B ) LOCATION: 1...492
        ( D ) OTHER INFORMATION:

( x i ) SEQUENCE DESCRIPTION: SEQ ID NO:32:

|     |     |     |     |     |     |     |     |     |     |     |     |     |     |     |     |
|-----|-----|-----|-----|-----|-----|-----|-----|-----|-----|-----|-----|-----|-----|-----|-----|
| Met<br>1 | Ser | Ala | Leu | Leu<br>5 | Ile | Leu | Ala | Leu | Val<br>10 | Gly | Ala | Ala | Val | Ala<br>15 | Asp |
| Tyr | Lys | Asp | Asp<br>20 | Asp | Asp | Lys | Lys | Ser<br>25 | Pro | Cys | Gln | Pro | Asn<br>30 | Pro | Cys |
| His | Gly | Ala<br>35 | Ala | Pro | Cys | Arg | Val<br>40 | Leu | Pro | Glu | Gly | Gly<br>45 | Ala | Gln | Cys |
| Glu | Cys<br>50 | Pro | Leu | Gly | Arg | Glu<br>55 | Gly | Thr | Phe | Cys | Gln<br>60 | Thr | Ala | Ser | Gly |
| Gln<br>65 | Asp | Gly | Ser | Gly | Pro<br>70 | Phe | Leu | Ala | Asp | Phe<br>75 | Asn | Gly | Phe | Ser | His<br>80 |
| Leu | Glu | Leu | Arg | Gly<br>85 | Leu | His | Thr | Phe | Ala<br>90 | Arg | Asp | Leu | Gly | Glu<br>95 | Lys |
| Met | Ala | Leu | Glu<br>100 | Val | Val | Phe | Leu | Ala<br>105 | Arg | Gly | Pro | Ser | Gly<br>110 | Leu | Leu |
| Leu | Tyr | Asn | Gly<br>115 | Gln | Lys | Thr | Asp<br>120 | Gly | Lys | Gly | Asp | Phe<br>125 | Val | Ser | Leu |
| Ala | Leu<br>130 | Arg | Asp | Arg | Arg | Leu<br>135 | Glu | Phe | Arg | Tyr | Asp<br>140 | Leu | Gly | Lys | Gly |
| Ala<br>145 | Ala | Val | Ile | Arg | Ser<br>150 | Arg | Glu | Pro | Val | Thr<br>155 | Leu | Gly | Ala | Trp | Thr<br>160 |
| Arg | Val | Ser | Leu | Glu<br>165 | Arg | Asn | Gly | Arg | Lys<br>170 | Gly | Ala | Leu | Arg | Val<br>175 | Gly |
| Asp | Gly | Pro | Arg<br>180 | Val | Leu | Gly | Glu | Ser<br>185 | Pro | Lys | Ser | Arg | Lys<br>190 | Val | Pro |
| His | Thr | Val<br>195 | Leu | Asn | Leu | Lys | Glu<br>200 | Pro | Leu | Tyr | Val | Gly<br>205 | Gly | Ala | Pro |
| Asp | Phe<br>210 | Ser | Lys | Leu | Ala | Arg<br>215 | Ala | Ala | Ala | Val | Ser<br>220 | Ser | Gly | Phe | Asp |

```
Gly Ala Ile Gln Leu Val Ser Leu Gly Gly Arg Gln Leu Leu Thr Pro
225             230                 235                     240

Glu His Val Leu Arg Gln Val Asp Val Thr Ser Phe Ala Gly His Pro
                245                 250                 255

Cys Thr Arg Ala Ser Gly His Pro Cys Leu Asn Gly Ala Ser Cys Val
            260             265                 270

Pro Arg Glu Ala Ala Tyr Val Cys Leu Cys Pro Gly Gly Phe Ser Gly
        275             280                 285

Pro His Cys Glu Lys Gly Leu Val Glu Lys Ser Ala Gly Asp Val Asp
    290             295             300

Thr Leu Ala Phe Asp Gly Arg Thr Phe Val Glu Tyr Leu Asn Ala Val
305             310             315                     320

Thr Glu Ser Glu Leu Ala Asn Glu Ile Pro Val Glu Lys Ala Leu Gln
                325             330                 335

Ser Asn His Phe Glu Leu Ser Leu Arg Thr Glu Ala Thr Gln Gly Leu
            340             345             350

Val Leu Trp Ser Gly Lys Ala Thr Glu Arg Ala Asp Tyr Val Ala Leu
        355             360             365

Ala Ile Val Asp Gly His Leu Gln Leu Ser Tyr Asn Leu Gly Ser Gln
    370             375             380

Pro Val Val Leu Arg Ser Thr Val Pro Val Asn Thr Asn Arg Trp Leu
385             390             395                     400

Arg Val Val Ala His Arg Glu Gln Arg Glu Gly Ser Leu Gln Val Gly
            405             410                 415

Asn Glu Ala Pro Val Thr Gly Ser Ser Pro Leu Gly Ala Thr Gln Leu
            420             425             430

Asp Thr Asp Gly Ala Leu Trp Leu Gly Gly Leu Pro Glu Leu Pro Val
        435             440             445

Gly Pro Ala Leu Pro Lys Ala Tyr Gly Thr Gly Phe Val Gly Cys Leu
    450             455             460

Arg Asp Val Val Val Gly Arg His Pro Leu His Leu Leu Glu Asp Ala
465             470             475                     480

Val Thr Lys Pro Glu Leu Arg Pro Cys Pro Thr Pro
            485             490
```